US012806430B2

(12) United States Patent
Bardy et al.

(10) Patent No.: US 12,806,430 B2
(45) Date of Patent: Nov. 24, 2026

(54) DEFIBRILLATOR WITH A RELEASABLE WIRE ASSEMBLY

(71) Applicant: Bardy Technologies, Inc., Vashon, WA (US)

(72) Inventors: Cameron M.D. Bardy, Sammamish, WA (US); Joshua Djon Green, Seattle, WA (US); Jason Felix, Vashon Island, WA (US); Gust H. Bardy, Carnation, WA (US)

(73) Assignee: Bardy Technologies, Inc., Bellevue, WA (US)

( * ) Notice: Subject to any disclaimer, the term of this patent is extended or adjusted under 35 U.S.C. 154(b) by 0 days.

(21) Appl. No.: 18/982,957

(22) Filed: Dec. 16, 2024

(65) Prior Publication Data

US 2025/0114625 A1 Apr. 10, 2025

Related U.S. Application Data

(63) Continuation-in-part of application No. 18/486,992, filed on Oct. 13, 2023, now Pat. No. 12,220,592, which is a continuation-in-part of application No. 18/156,318, filed on Jan. 18, 2023, now Pat. No. 11,794,026.

(51) Int. Cl.
*A61N 1/39* (2006.01)
*A61N 1/04* (2006.01)

(52) U.S. Cl.
CPC ......... *A61N 1/3968* (2013.01); *A61N 1/0472* (2013.01)

(58) Field of Classification Search
CPC ............................ A61N 1/3968; A61N 1/0472
See application file for complete search history.

(56) References Cited

U.S. PATENT DOCUMENTS

| | | | |
|---|---|---|---|
| 4,808,152 A | 2/1989 | Sibalis | |
| 5,040,534 A | 8/1991 | Mann et al. | |
| 5,314,502 A | 5/1994 | McNichols et al. | |
| 5,466,244 A * | 11/1995 | Morgan | A61N 1/046 607/152 |
| 5,562,607 A | 10/1996 | Gyory | |
| 5,645,571 A | 7/1997 | Olson et al. | |
| 5,658,319 A | 8/1997 | Kroll | |

(Continued)

FOREIGN PATENT DOCUMENTS

| | | |
|---|---|---|
| DE | 102017116138 | 1/2019 |
| WO | 2022165179 | 8/2022 |

*Primary Examiner* — Eric D. Bertram
(74) *Attorney, Agent, or Firm* — Krista A. Wittman

(57) ABSTRACT

A defibrillator with a releasable wire assembly is provided. Four walls are each affixed on one side of a bottom surface. A dividing layer is affixed to each of the four walls creating an electrode enclosure configured to hold a pair of pads and a circuit enclosure configured to hold circuitry. Access to the circuitry is restricted by the bottom surface and dividing layer. A pair of wires are each connected on one end to one of the pads in the electrode enclosure and connected on another end to the circuitry in the circuit enclosure. A spool is placed within the electrode enclosure and includes a barrel with two center pieces through which the pair of wires is secured. The wires are wound around an outer surface of the center pieces of the spool, in the electrode enclosure, and are unwound when the pads are removed from the electrode enclosure.

20 Claims, 33 Drawing Sheets

(56) References Cited

U.S. PATENT DOCUMENTS 5,697,955 A 12/1997 Stolte
5,797,969 A 8/1998 Olson et al.
5,868,794 A 2/1999 Barkley
5,876,424 A 3/1999 O'phelan
5,957,956 A * 9/1999 Kroll ...................... A61N 1/375 607/5
6,083,246 A 7/2000 Stendahl et al.
6,173,203 B1 1/2001 Barkley
6,208,896 B1 3/2001 Mulhauser
6,377,848 B1 4/2002 Garde et al.
6,384,588 B1 5/2002 Mulhauser
6,441,513 B1 8/2002 Mulhauser
6,556,864 B1 4/2003 Picardo
6,662,056 B2 * 12/2003 Picardo ................ A61N 1/0472 607/142
7,072,712 B2 * 7/2006 Kroll ................... H01M 50/247 607/36
7,848,804 B1 12/2010 Kroll
9,168,386 B2 * 10/2015 Schwibner .............. G06F 21/31
9,889,311 B2 * 2/2018 Horseman ............ A61N 1/3925
10,238,881 B2 3/2019 Axness
10,449,380 B2 * 10/2019 Andrews ................ A61N 1/395
10,668,296 B2 * 6/2020 Meir .................... A61N 1/3993
10,799,709 B2 * 10/2020 Teber ................... A61N 1/3968
11,547,863 B1 * 1/2023 Shaker ................. A61N 1/3904
11,633,613 B1 * 4/2023 Shaker ................. A61N 1/3904 607/5
11,794,025 B1 * 10/2023 Shaker ................. A61N 1/0492
11,911,627 B1 * 2/2024 Shaker ................. A61N 1/3968
2002/0133197 A1 9/2002 Snyder et al.
2003/0028219 A1 2/2003 Powers et al.
2003/0080712 A1 * 5/2003 Tamura ................ A61N 1/3975 320/103
2003/0120311 A1 6/2003 Hansen
2003/0181950 A1 9/2003 Powers
2004/0002736 A1 1/2004 Waltman
2004/0068301 A1 4/2004 Waltman et al.
2004/0133242 A1 7/2004 Chapman
2004/0143297 A1 * 7/2004 Ramsey, III ......... A61N 1/3975 607/5
2004/0243184 A1 12/2004 Johnson et al.
2006/0111748 A1 5/2006 Bucher
2006/0178865 A1 * 8/2006 Edwards .............. A61N 1/3993 704/1
2006/0286861 A1 * 12/2006 Avevor .................. A61B 5/303 439/501
2007/0055308 A1 3/2007 Haller et al.
2008/0287589 A1 11/2008 Ounaies et al.
2009/0157132 A1 6/2009 Linder
2010/0022904 A1 1/2010 Centen
2010/0114236 A1 5/2010 Jiang et al.
2010/0168821 A1 7/2010 Johnson et al.
2011/0046688 A1 * 2/2011 Schwibner .............. G06F 21/31 607/5
2011/0202101 A1 * 8/2011 Tan ...................... G09B 19/003 607/7
2012/0059436 A1 3/2012 Fontaine et al.
2013/0053911 A1 2/2013 Hareland
2013/0066390 A1 3/2013 Schwibner et al.
2013/0228485 A1 9/2013 Roach et al.
2014/0317914 A1 * 10/2014 Shaker ................... A61N 1/046 29/825
2014/0324111 A1 * 10/2014 Wu ...................... A61N 1/3968 607/7
2016/0250492 A1 9/2016 King et al.
2016/0271408 A1 9/2016 Newton et al.
2016/0321957 A1 11/2016 Petruzziello
2016/0328529 A1 11/2016 Kaib et al.
2017/0157415 A1 * 6/2017 Horseman ............ H04B 1/3888
2017/0157416 A1 6/2017 Medema et al.
2017/0246466 A1 8/2017 Murphy et al.
2018/0140859 A1 * 5/2018 Meir .................... A61N 1/3993
2018/0161587 A1 6/2018 Beyer
2018/0207435 A1 7/2018 Yetter
2018/0280708 A1 * 10/2018 Escalona ................. H02J 50/10
2018/0318592 A1 * 11/2018 Smith .................... A45C 11/00
2018/0339162 A1 11/2018 Taylor et al.
2019/0044362 A1 * 2/2019 Beyer ................. H02J 7/00714
2019/0117989 A1 * 4/2019 Andrews ................... H02J 7/00
2019/0356492 A1 * 11/2019 Picco .................... H04L 67/125
2020/0038649 A1 2/2020 Manicka
2020/0094044 A1 3/2020 Andrews
2020/0254246 A1 8/2020 Zorman
2021/0093877 A1 * 4/2021 Beyer ............... H02J 7/007182
2021/0257849 A1 8/2021 Keil
2021/0275131 A1 9/2021 Siedenburg et al.
2021/0379393 A1 12/2021 Butler
2023/0041857 A1 * 2/2023 Prutchi ................ A61N 1/3956
2023/0084585 A1 3/2023 Sohn et al.
2023/0089192 A1 * 3/2023 Bennett ................ A61N 1/0484 607/142
2023/0310873 A1 * 10/2023 Shaker ................... A61N 1/046 607/5
2025/0114623 A1 * 4/2025 Bardy .................. A61N 1/3968
2025/0114626 A1 * 4/2025 Bardy .................. A61N 1/3968
2025/0186793 A1 * 6/2025 Bardy .................. A61N 1/3904

* cited by examiner

70

100

110

120

130

150

190

360

DEFIBRILLATOR WITH A RELEASABLE WIRE ASSEMBLY

CROSS-REFERENCE TO RELATED APPLICATIONS

This non-provisional patent application is a continuation-in-part of U.S. Pat. No. 12,220,592, issued Feb. 11, 2025, which is a continuation-in-part of U.S. Pat. No. 11,794,026, issued Oct. 24, 2023, the priority dates of which are claimed and the disclosure of which is incorporated by reference.

FIELD

This invention relates in general, to device cases and in particular, to a pocketable defibrillator housing that is designed to facilitate rapid deployment of defibrillator pads together with a secure wire assembly for the pads. Pad housing and connections to the power source are critical to the speed of deployment of a defibrillator shock, the most important factor in saving a life from cardiac arrest where seconds make the difference between death and survival.

BACKGROUND

Sudden cardiac arrest (SCA) is a significant cause of mortality throughout the world and remains a major public health concern causing about 300,000 to 450,000 deaths each year in the United States alone, despite the broad scale teaching of cardiopulmonary resuscitation (CPR) and the implementation of public access automated external defibrillators (AED) in hospitals, ambulances, and other public locations, like airports and stadiums. More than 9 of 10 SCA victims of SCA die, even in locales with advanced medic response systems. In most locations globally, the death rate approaches 100%.

SCA occurs when the heart suddenly and unexpectedly stops pumping blood, most commonly caused by a chaotic cardiac rhythm disorder known as ventricular fibrillation (VF). VF is a lethal heart rhythm abnormality that causes the ventricles of the heart to quiver, resulting in ineffective contraction of the ventricles and a failure to pump blood. Accordingly, blood pressure plummets and blood delivery to the brain and all bodily organs essential ceases and yielding loss of consciousness in 5-10 seconds.

SCA from VF constitutes the most time-critical emergency in medicine and is universally lethal within 10-20 minutes without prompt medical attention, specifically the delivery of a high-voltage, high-energy shock across the chest via a defibrillator, the only method known to stop VF. Preferably such a shock is delivered within 5 minutes of the onset of VF upon rapid deployment of easily accessible defibrillation pads.

Because victims of VF collapse within 5-10 seconds, lose consciousness, and become unresponsive, only someone that is physically near the victim has a meaningful chance at preventing death. The chance of survival rapidly decreases 7-10% per minute from onset of VF and, after 10 minutes, resuscitation rarely succeeds, even with CPR, and even if an AED is used, as the heart and brain will have suffered irreversible injuries. Consequently, ensuring that people have immediate access to an AED is both absolutely essential to saving lives from cardiac arrest, where every minute counts, and critically dependent upon a design that allows personal pocketability, such that the AED is compact enough to be carried everywhere with an individual, including in a pocket.

AEDs made publicly available, however, have not meaningfully addressed the problem of SCA in part because they are not designed to be easily wearable, like a cell phone that is carried by nearly every individual today. By various accounts, there are approximately 3.2 to 4.5 million AEDs currently deployed in public places in the United States, yet an estimated more than 30 million AEDs are needed to provide sufficient coverage to meaningfully improve cardiac arrest survival rate nationally. Moreover, despite this disparity between the number of devices versus the estimated need, increasing the number of public access AEDs by an order of magnitude would be neither practical in terms of cost or execution nor would such an increase truly address the problem that SCAs primarily occur in places other than where public access AEDs are found and, even so, rarely are readily available, given their bulk, even if such devices were present in the home. More than 70% of VF cases occur in or near the home or during routine activities of daily living, like yard-work and gardening, driving, personal recreation, and so on. These represent locations where public access AEDs are not usually found. Moreover, public access AEDs are rarely deployed or used in such locations where SCAs typically happen and, if they are, their use often comes far too late. Thus, the problem of resuscitating victims from VF is inexorably linked to time and proximity to an AED, which are, in turn, inexorably linked to convenience of use, which is a direct consequence of AED cost, size and weight. Accordingly, to make a positive impact on survivability of SCA requires a different approach to AED deployment. One solution would be to provide an AED that is first and foremost pocket-sized and modest in weight and cost, so that AEDs become practically ubiquitous, similar to a mobile phone.

The high cost and bulk of conventional public access AEDs are mainly due to the design choices of reusability, integrated telemetry and functionality intended to constantly perform and disclose the results of multi-use readiness checks. Typical AEDs perform self-testing constantly, depleting their battery, and causing wear on critical components. These design choices require large and complex circuits and components that will survive constant testing and the stress induced therein. Several AED product recalls have shown this practice to prematurely degrades components, resulting in an AED becoming non-functional when needed. AEDs are typically designed to eliminate failure modes, which, paradoxically, results in large and complex systems that are expensive and prone to failure. For example, conventional public access AED capacitors are often rated for operation at 90° C. and 20,000 back-to-back pulse discharges, conditions that do not remotely resemble the typical use case under any conceivable scenario which is 1-3 shocks in normal environmental conditions. Moreover, reusability requirements mean that the batteries must be able to store enough energy to defibrillate multiple patients, perform simulated use testing, as well as have circuits that are able to sense when the device will not be "rescue ready" in the future.

The above list of historical technical design features, that have not meaningfully improved survival of SCA over the past 30 years are key factors that effectively restrict deployment of public access AEDs to healthcare providers, first responders, and public areas that are legally required to have an AED, all of which make existing AEDs relatively unavailable and of no use for the majority of VF emergencies that occur at or near the home away from public access AEDs. Moreover, public access AEDs are packaged in large carrying cases weighing several pounds that are too bulky to be convenient for ubiquitous use by the public. Despite their design intent of simplicity for use, rescuers are often in a state of confusion, even panic. Today's AEDs are geared toward the SCA-informed user, rather than the stressed, often terrified rescuer. As a consequence, a very intuitive, ultra-simple deployment strategy is critical. Finally, AEDs typically cost between $1000 to $2200, which is too expensive for the average person to buy or to serve as a personal safety tool to accompany activities of daily living.

Therefore, a need remains for providing a lightweight pocket-sized AED simply designed for single use by naïve and frightened rescuers. Preferably, the AED, including housing, is both secure, durable, yet immediately deployable by a rescuer in the most dire of life and death circumstances.

SUMMARY

A compact lightweight AED promotes widespread use and helps ensure availability when needed. The electrical components of the AED, as well as the housing or case of the AED, should be sized to fit within a pocket for ease of carrying for continuous availability. The case should accommodate the necessary electrical components of a defibrillator, like a relatively large high-voltage capacitor, while simultaneously allowing rapid defibrillation, shock pad release, and use by an average citizen within a short time, such as one minute of victim collapse, without need for contemplation or further deployment complexities other than application of the shock pads to the right infraclavicular and left inferolateral, anterior thorax beneath the heart. Facilitation of effective use requires that purposeful movement of one or more components of the carrying case triggers charging of the AED for intended ventricular fibrillation detection and shocks promptly upon application, while also guarding against unintended opening of the case.

The AED components that facilitate a pocket size (i.e., a cell phone size) AED must not only have an innovative shock pad housing capable of minimalist dimensions, but house the electronics, while also being capable of immediate and intuitive pad deployment and shocking the victim within one minute by a distressed and excited average citizen rescuer. Such a pocket size defibrillator case must include a circuit enclosure having a bottom surface surrounded by four walls forming a cavity to house an energy storage circuit adapting to electronic component variability, including relatively large components like the capacitor. An electrode enclosure includes a bottom surface surrounded by four walls forming a cavity to house electrode pads and is stacked on top of the circuit enclosure. A cover includes a substantially flat surface positioned over the electrode enclosure and moveable to allow access only to the electrode enclosure. Such an enclosure harbors routes of circuit connection and rescuer activation.

An embodiment provides a defibrillator housing with secure wire arrangement. Four walls are each affixed on one side of a bottom surface. A dividing layer is affixed to each of the four walls creating an electrode enclosure configured to hold a pair of pads each associated with a wire, and a circuit enclosure configured to hold circuitry. Access to the circuitry is restricted by the bottom surface and dividing layer. A plug is positioned in the dividing layer and has at least one pin that extends through the dividing layer to connect with the circuitry in the circuit enclosure. The wires are connected to one end of the plug, opposite the pins, to provide power to the pads.

A further embodiment provides a defibrillator with a feed through wire arrangement. Four walls are each affixed on one side of a bottom surface. A dividing layer includes a void and is affixed to each of the four walls creating an electrode enclosure configured to hold a pair of pads each associated with a wire, and a circuit enclosure configured to hold circuitry. Access to the circuitry is restricted by the bottom surface and dividing layer. A feedthrough connection is formed in the dividing layer and includes two portions perpendicularly affixed. One of the portions extends through the void and connects with the circuitry in the circuit enclosure. The other portion of the feedthrough mechanism is connected to a plug. The plug is connected the wires and has at least one pin positioned opposite the wires, wherein the plug is connected to the feedthrough connection via the pin to provide power to the pads.

A still further embodiment provides a defibrillator with a releasable wire assembly. Four walls are each affixed on one side of a bottom surface. A dividing layer is affixed to each of the four walls creating an electrode enclosure configured to hold a pair of pads and a circuit enclosure configured to hold circuitry. Access to the circuitry is restricted by the bottom surface and dividing layer. A pair of wires are each connected on one end to one of the pads in the electrode enclosure and connected on another end to the circuitry in the circuit enclosure. A spool is placed within the electrode enclosure and includes a barrel with two center pieces through which the pair of wires is secured. The wires are wound around an outer surface of the center pieces of the spool, in the electrode enclosure, and are unwound when the pads are removed from the electrode enclosure.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
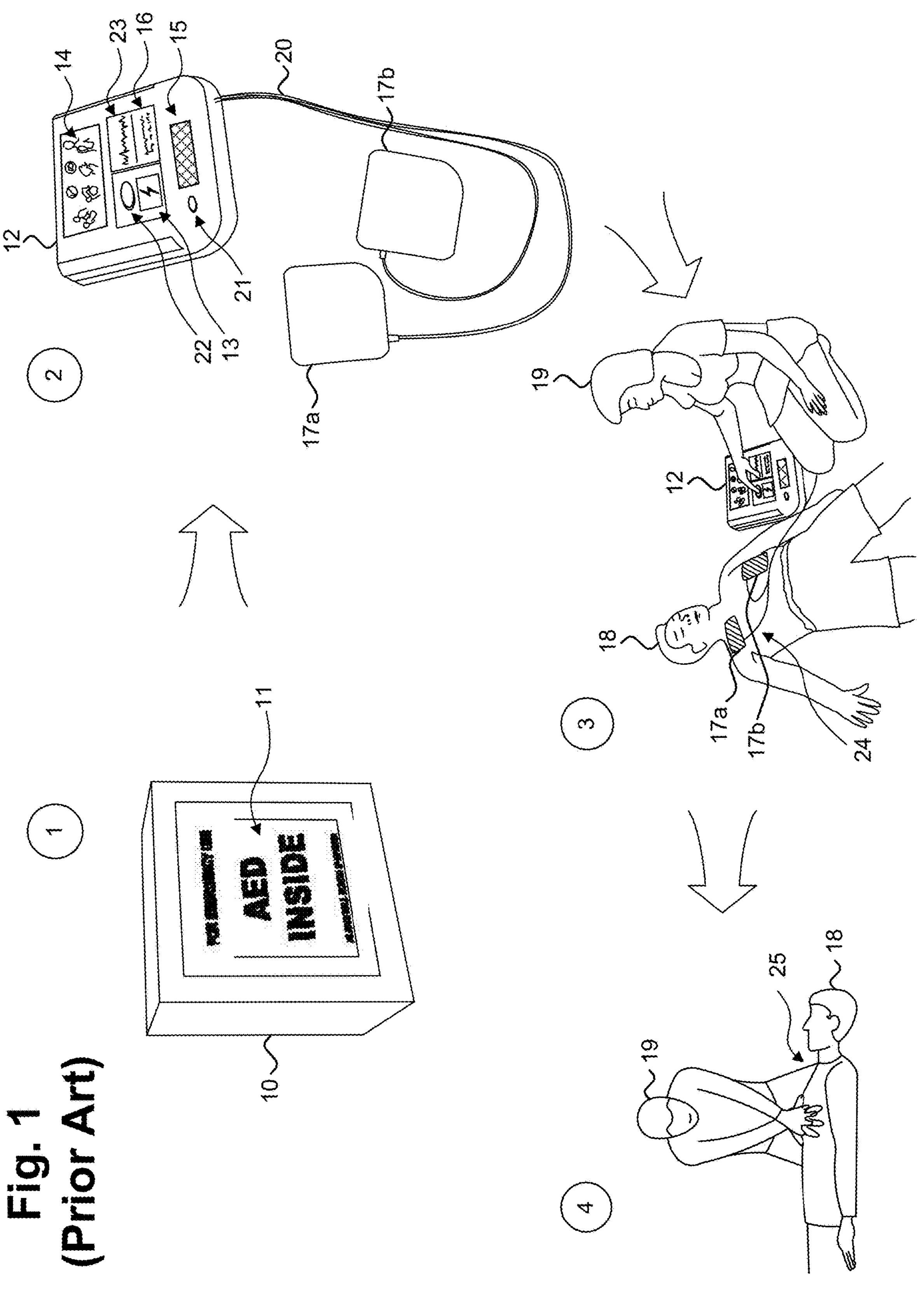
Fig. 1 (Prior Art)
FIG. 1 is a process flow diagram showing, by way of example, a typical prior art use of a public access AED in an SCA situation.

There has been a push to deploy public access AEDs in busy often-frequented places, such as airports, restaurants, casinos, shopping centers, and stadiums. Public access AEDs urge delivery of defibrillation shocks by a bystander in an attempt to restore normal cardiac rhythm. Such use only addresses a modest proportion of SCA victims and are typically deployed by unemotionally involved witnesses, often professional medical personnel that happen upon the victim. FIG. 1 is a process flow diagram showing, by way of example, a typical prior art use of a public access AED 12 in an SCA situation. Public access AEDs are designed for repeated use and harbor a complex array of visual, auditory and manual button-oriented instructions. They require, at minimum, monthly checks and relatively frequent pad and battery replacements. Despite their distribution, there has been little change in the death rates from SCA because most SCA occurs in the home or in average activities of daily living.

In a typical example of a public AED use, a victim 18 has suffered suspected cardiac arrest while in the company of a public rescuer 19. The terms "victim" and "patient" are used interchangeably and refer to the individual that is receiving emergency care for a possible cardiac arrest. Similarly, the terms "rescuer," "bystander" and "user" are used interchangeably and refer to the individual who is actively providing the emergency care through the use of a public access AED.

When SCA is suspected, often when a victim suddenly loses consciousness and collapses, a rescuer 19 must take immediate action to assist the victim 18. After ideally first calling 9-1-1, the rescuer 19 should check the victim 18 for a pulse and, if absent, begin basic life support maneuvers (BLS), which begins by first locating and obtaining a public use AED 12 (step (1)). Note that there are two main categories of AEDs, either of which may be found in use as a public use AED. Some AEDs automatically deliver shocks without rescuer action when pads are applied, following VF detection. Most AEDs, however, are semi-automatic and require the rescuer to manually trigger a shock with a button or device control. The portable AEDs carried by emergency medical services (EMS) personnel are generally designed as semi-automatic AEDs that include physiological monitoring tools for both basic and advanced life support, as well as include advanced CPR feedback and vital signs patient monitoring.

A typical public access AED 12 is located where the general public ordinarily has access kept in some type of protective housing 10, such as a display case, wall cabinet or kiosk. Public access AEDs are designed for long-term reuse and to be available to save multiple victims over their service lifetime. Thus, these devices are physically robust to withstand rough and repeated use, if properly maintained during periodic checks. Such complicating factors that add to unit cost and size, include these maintenance obligations as well as telemetry functionality needed to prevent failures and sustain readiness over time. Further, the public access AED 12 itself is portable and therefore susceptible to being misplaced or stolen; the protective housing 10 helps to keep the public access AED 12 secure and available until needed. Theft can be common in major cities and the AED must remain readily available. Note that, despite being portable, a public access AED kit is bulky and weighs several pounds, which makes carrying a public access-type AED on an everyday basis impractical for nearly all individuals, even though wider AED availability and use could help save more lives. In addition, both the electrodes and batteries of public access AEDs have expiration dates and must be replaced upon their respective expiry every one to three years. Moreover, these traditionally designed AEDs must undergo periodic operational testing that may require that the defibrillation circuit be energized, resulting in a depleted battery charge as well as commonly and prematurely degrading the circuit, which paradoxically contradicts the original design intent of periodic testing.

Returning to the steps of AED use in public, once the rescuer 19 locates and obtains an AED, the rescuer must activate the AED 12, which generally entails pressing an "On" button or other simple-to-use control (step (2)). Conventional public use AEDs 12 are packaged in a large carrying case that contains the AED circuit, including sensing and defibrillation circuit and battery, a pair of shock paddles (not shown) or, more commonly, adhesive dermal electrode pads 17*a-b* connected by a set of leads 20, and support accessories (not shown), such as gloves and a face shield. Note that shock paddles and adhesive electrode pads are both acceptable modes for delivering defibrillation shocks and when used correctly, are equally efficacious. Conventional shock paddles and electrode pads are generally about 8-12 cm in length, rectangular, and intended to conform to the human thoracic anatomy.

As most rescuers will be lay bystanders, albeit often with medical background, public use AEDs generally provide visual and usually verbal instructions 14 on assessing the victim's breathing and placement of its electrode pads 17*a-b* on the victim's chest 24 (step (3)). The AED includes a set of necessary controls, typically an "On" button 21 and, if the AED is semi-automatic, a "Shock" button 22 to manually deliver a defibrillation shock by the rescuer, plus a warning indicator 13 that the AED is charged and ready to deliver a defibrillation shock. To activate the public use AED 12, the rescuer 19 presses the "On" button 21. The visual instructions 14 are typically supplemented with speaker-generated voice prompts 15, display-generated text prompts 16, in some cases, an electrocardiogram (ECG) 23, or some combination of voice prompts, text prompts and an ECG. The American Heart Association (AHA) and European Resuscitation Counsel (ERC) publishes guidelines outlining a recommended sequence of visual and voice prompts to help rescuers in proper use of AEDs. See, 2010 *American Heart Association Guidelines for CPR and ECC; Supplement to Circulation*, Vol. 192, Issue 18 (Nov. 12, 2010). *European Resuscitation Council Guidelines for Resuscitation* 2010, *Resuscitation* Volume 81 (October 2010). Despite such control over rescuer interactions with the classically designed AED, little progress has been made in SCA survival, perhaps to the confusion and valuable time loss, such visual, auditory, communicative, and mechanical commands yield.

The electrode pads 17*a-b* must be applied by the rescuer 19 to be in direct contact with the victim's skin. With traditional AED kits, many include a razor to shave any hair off the victim's skin where the electrode pads 24 are to be placed. The intent is to maximize the transit of current through the heart. However, shaving the hair costs valuable time. This is routinely done despite the absence of data to show meaningful improvement in current flow through the thorax by shaving hair. The practice is a legacy of in-hospital experience whereupon pad removal from hairy chests during elective cardioversion are known to be painful. In the case of a cardiac arrest, however, such concerns are trivial compared to saving a life. Even a one-minute loss in shock delivery carries a 10% mortality rate. Later in the resuscitation efforts, such delays are lethal and partly contribute to the poor results in SCA resuscitation. Accordingly, our casing design in this application is informed by such prior time-wasting considerations as will be discussed shortly.

Public access AEDs are designed for use on multiple victims, which leads to a complex and typically over-engineered design that leads to high cost and long-term maintenance obligations and frequent failures, as well as complexity of use by the truly lay user.

The life-saving benefits of AEDs can be efficaciously provided to every person, everywhere, and on a 24/7/365 basis through a disposable, single-use AED that is small enough to be truly portable, for instance by fitting in an average-sized pocket. A single use AED, that is, a device that is available to therapeutically treat one instance of SCA, significantly streamlines and simplifies the design requirements of the AED and accordingly makes it possible to house the AED in a small pocketable form factor. Periodic maintenance is not required, as the disposable nature of the pocket AED implies the device will be discarded before needing to undergo maintenance or other testing prior to use on a patient. As well, the reliability level of the electronic components can be selected to be appropriate to accommodate a single use scenario, rather than repeated uses over an extended service life of many years, limiting complexity and improving durability, such as been shown in military applications. Similarly, the battery can be smaller and lighter, as battery life will not be depleted by long shelf life and telemetry transmissions related to diagnostic routines and maintenance cycles. Further, the use of such simplified electronic components and battery technologies lowers cost and allows disposability to be realized. Finally, to encourage being carried by users at all times, the pocket AED is sized comparably to a large smartphone, for instance, in the range of 2.25 to 3.625 inches wide, 5.25 to 7 inches tall, and 0.25 to 1.875 inches deep, and of similar weight, for example, in the range of 130 to 945 grams.

Figure 2:
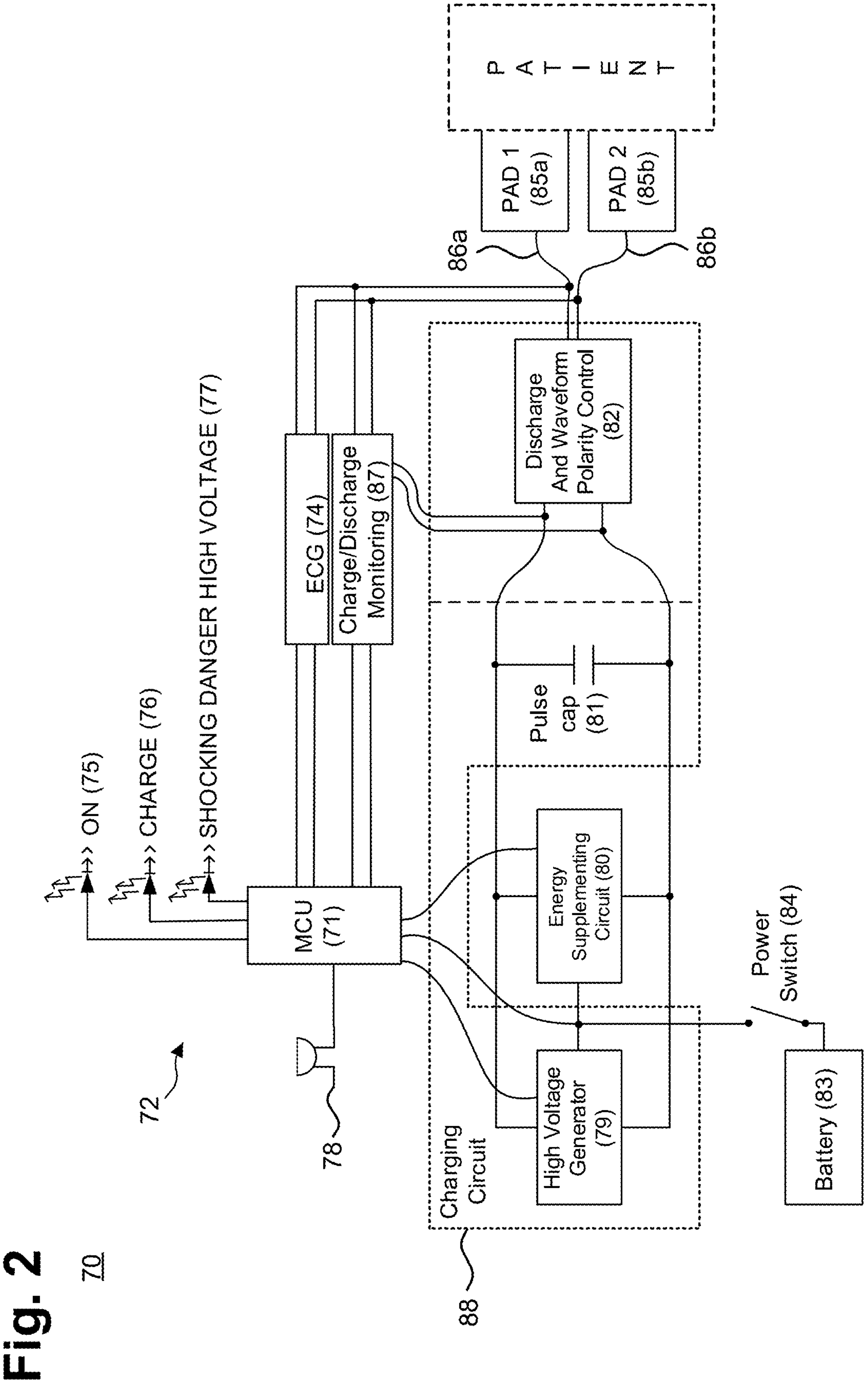
FIG. 2 is a block diagram showing functional components and a user interface for a disposable single use pocketable AED in accordance with one embodiment.

Facilitating the construction of a disposable pocketable AED to fit into a small easy to use form factor, requires the defibrillation circuit to utilize a therapy delivery (shock) methodology that functions off of a low voltage energy storage and supplementation circuit. FIG. 2 is a block diagram showing functional components and a user interface 72 for a disposable pocketable AED. For the sake of subsequent clarity of the casing and pad deployment and use system, the defibrillation circuit 70 will be discussed in detail as both the casing innovation and the circuitry innovation are hand in glove coordinated.

The defibrillation circuit 70 includes components for providing a basic user interface 72 that includes a power switch (84), a "Power On Indicator" 75, a charging indicator 76, and optionally, a warning indicator 77 that indicates defibrillation shock delivery readiness with attendant dangers of exposure to high-voltage, plus an optional buzzer or speaker 78 through which audible instructions can be played. In one embodiment the user interface 72 also includes a visual display (not shown) on which text prompts can be displayed. In one embodiment, an AED incorporating the defibrillation circuit 70 can be semi-automatic and require the rescuer to manually trigger a shock by actuating the push to shock button (not shown); in a further embodiment, an AED incorporating the defibrillation circuit 70 employs a circuit to automatically deliver the defibrillation shock to the victim without user action once the charging circuit is ready, that is, the pulse capacitor is charged, and after the user has been warned to avoid any direct physical contact with the patient during shock delivery.

The defibrillation circuit 70 is controlled by a microcontroller unit (MCU) 71 or system-on-chip controller (SOC) (not shown) that is programmable, which allows updated controller firmware to be downloaded from an external source into a persistent memory store. Sensing circuit 87 is connected in parallel with the inputs and outputs of a discharge and polarity control circuit 82. The sensing circuit 87 determines the high-voltage capacitor charge level and captures the patient shock waveform and transmits it to the MCU 71. The defibrillation energy that is received from the pulse capacitor 81 as an input to the discharge and polarity control circuit 82 and the defibrillation waveform or "pulse" that is output is captured by the sensing circuit 87 and transmitted to the MCU 71. An ECG front end circuit 74 captures the heart rhythm and transmits the rhythm to the MCU 71. The ECG front end circuit 74 is connected in parallel with the leads 86*a-b* of the pair of electrode pads 85*a-b* to sense cardiac signals, while the sensing circuit 87 is connected in parallel with the discharge and polarity control module's input leads to monitor the shock delivery process. In a further embodiment, the MCU 71 interfaces to the sensing circuit 87 to continually measure patient impedance and adjusts parameters in the high-voltage generator module 79 and the low voltage energy supplementing module 80 to alter one or more of energy, voltage, and pulse width in real time, as further discussed infra with reference to FIG. 8. The ECG is transmitted to the MCU 71 where an algorithm makes a shock or no-shock decision. The algorithm is implemented through conventional VF detection algorithm to detect the presence of a shockable rhythm, such as published by A. Fan, et al., Shockable Rhythm Detection Algorithms for Electrocardiogramathm in Automated Defibrillators, AASRI Conf. on Comp. Intel. and Bioinfor. pp. 21-26 (2012). The ECG front end circuit 74 is implemented optionally through conventional ECG analog front-end chips such as the ADS1x9xECG-FE family of integrated analog front-end ECG circuits, available from Texas Instruments, Dallas, TX. Other types and configurations of sensing and ECG front end circuitries are possible.

When a shockable rhythm is detected, based on inputs from the an impedance sensing circuit (not shown), the MCU 71 determines the parameters of a defibrillation waveform in terms of energy, voltage, and pulse width; the defibrillation waveform is algorithmically selected based on the nature of the shockable rhythm to be medically appropriate for restoring normal cardiac rhythm. Up to a maximum of six shocks may be needed if the victim fails to be resuscitated, after which further shocks are generally futile.

In response to the ECG waveform the microcontroller or SoC 158 uses an algorithm to determine if a shockable rhythm is still present after initial shock delivery, that is, defibrillation failed to establish normal cardiac rhythm, the MCU 71 may simply repeat the delivery of the defibrillation pulse or, if appropriate, revise the parameters of the defibrillation waveforms for the subsequent pulses. In an alternative embodiment for such a situation, subsequent defibrillation shocks may need to be escalated in energy output or other waveform characteristics. In a further embodiment, parameters consisting of one or more of energy, voltage and pulse width are adjusted by the MCU 71 in real time, as further discussed infra with reference to FIG. 8.

In one embodiment defibrillation energy is generated through a combination of a modified conventional charging circuit 88 and a low voltage energy supplementing module 80 which are synchronously controlled by the MCU 71. The charging circuit 88 includes a high-voltage generator module 79, which conventionally charges a high-voltage pulse capacitor 81 with energy that is stored for delivery as a defibrillation shock. The charging circuit 88 also includes a discharge and polarity control module 82, optionally in the form of an H-bridge, that switches in response to the sensing circuit 87, or, where the AED is semi-automatic, in response to the pressing of the "Shock" button or similar manual control, to deliver an appropriate defibrillation shock over the electrode pads 85*a-b*. Other configurations of switching elements in lieu of or in addition to an H-bridge are possible.

The discharge and polarity control module 82 interfaces over a pair of leads 86*a-b* to electrode pads 85*a-b* as outputs and to the pulse capacitor 81 as inputs. The H-bridge is formed with two "legs" on the output side containing the leads 86*a-b* for the electrode pads 85*a-b* and the other two "legs" on the input side electrically connected to a pulse capacitor 81. The discharge and polarity control module 82 is switchable to receive the defibrillation energy from the pulse capacitor 81, which is output by the discharge and polarity control module 82 as a defibrillation waveform or "pulse." In a further embodiment, the discharge and polarity control module 82 includes a polarity reversal correction circuit to ensure proper shock delivery in the event that the electrode pads 85*a-b* are improperly reversed. In a yet further embodiment, the polarity could automatically be reversed on the third defibrillation shock, as reversing polarity can aid in defibrillation of difficult cases.

The low voltage energy supplementing module 80 works as an adjunct to the high-voltage generator module 79 and generates supplementary defibrillation energy that is injected into the inputs of the pulse capacitor 81. The low voltage energy supplementing module 80 is electrically connected to the pulse capacitor 81 in line with the high-voltage generator circuit 79 and is constructed using one or more low voltage ultra-capacitors that store supplemental defibrillation energy. By virtue of having the low voltage energy supplementing module 80 effectively "on tap" to augment the defibrillation energy, the load on the pulse capacitor 81 is thereby lower when compared to the load required to charge a pulse capacitor in a conventional AED, which, in turn, enables the high-voltage generator module 79 and pulse capacitor 81 as used herein to be implemented with lower energy components. Furthermore, such lower energy components are well suited for use in an AED that is intended to be disposable and single use, where only a relatively reasonable degree of robustness is needed, and reusability is not required. In addition, these components lower the cost, size, and weight of the AED, enabling the AED to be packaged in a form factor, as described infra, that can readily fit into an average-sized pocket in a fashion analogous to contemporary mobile telephones.

The MCU 71 monitors the defibrillation waveform through the sensing circuit 87 and adjusts the supplemental defibrillation energy stored by enabling and disabling the low voltage ultra-capacitors. A high-voltage step-up transformer is used by the low voltage energy supplementing module 79 to inject the stored supplemental defibrillation energy into the inputs of the pulse capacitor 81. This type of transformer can be packaged in a flat and thin planar design, known as a Planar Laminated High Energy Pulse Transformer, which is optimal for energy conversion efficiency and an ideal shape for a smartphone-like casing design. The low voltage energy supplementing module 80 uses a set of ultra-capacitors (or possible a single ultra-capacitor) in the range of 2.5V-48V and stores an amount of energy needed or to supplement a defibrillation pulse. The amount of supplementation varies depending on the application and target parameters of the device. The energy stored on the low voltage circuit could be as low as 10 J, or as high as 3 times the full defibrillation energy. The low voltage energy supplementing module 80 additively contributes to the energy generated by the high-voltage generator module 79.

Figure 3:
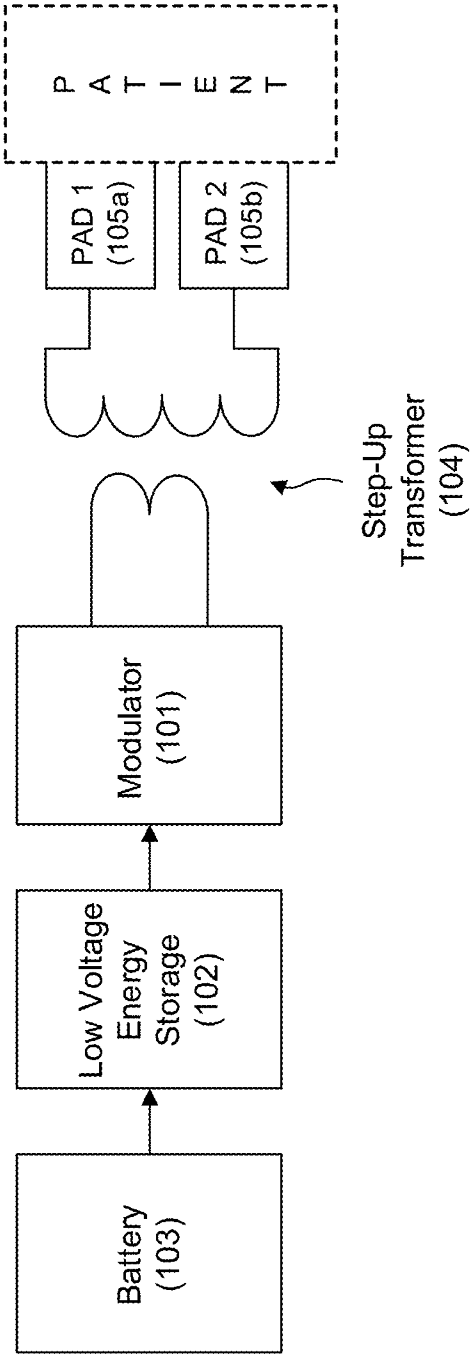
FIG. 3 is a schematic and block diagram showing a low voltage energy storage circuit for generating defibrillation waveforms energy in accordance with a further embodiment.

Low voltage energy storage for generating or supplementing defibrillation waveforms can be achieved through several circuits, as discussed with reference to FIGS. 3-7. While described in the context of use in personal AEDs, these low voltage high-energy storage circuits are adaptable for use in hospital defibrillators and in medic vehicle defibrillators as well as in implantable defibrillators. In its simplest form, energy is stored at a low voltage and switched through a step-up pulse transformer to generate the necessary defibrillation waveform, such as the biphasic waveform 181 (shown in FIG. 8). FIG. 3 is a schematic diagram showing a low voltage energy storage circuit 100 for generating defibrillation energy waveforms in accordance with one embodiment. Except as otherwise noted, the sensing and ECG circuits are omitted for clarity.

Here, the defibrillation circuit 100 includes four basic components, a pulse optimized step-up transformer 104 that feeds the defibrillation energy to a pair of electrodes 105*a-b*. The transformer 104 is driven by a modulator (or load switch) 101 that is fed by a low voltage energy storage module 102 containing one or more low voltage ultra-capacitors. Power is supplied by a battery 103. This circuit is completely open loop and relies upon pre-computed timing control pulses to instantiate the defibrillation waveform. In addition, this circuit is simple and therefore low cost.

Figure 4:
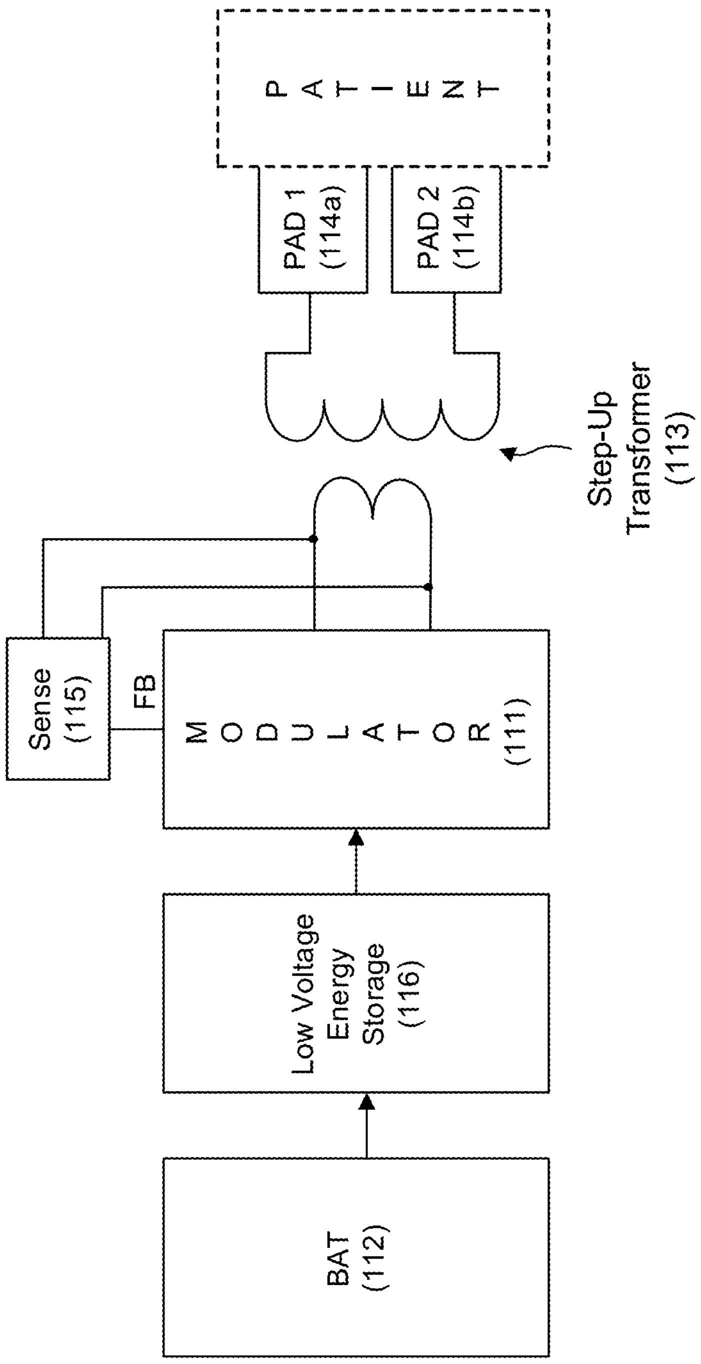
FIG. 4 is a schematic and block diagram showing a low voltage energy storage circuit for generating defibrillation waveforms energy with feedback in accordance with a further embodiment.

In another embodiment the electrical stimulus delivered to the patient can be monitored and inferred through current sensing employed on the primary side of the high-voltage pulse transformer. FIG. 4 is a schematic diagram showing a low voltage energy storage circuit 110 for generating defibrillation energy waveforms with feedback in accordance with a further embodiment. As before, the sensing and ECG circuits are omitted for clarity except as otherwise noted.

Here, the defibrillation circuit 110 includes four basic components, a pulse optimized step-up transformer 113, which serves to convert low-voltage high current energy to a high-voltage defibrillation pulse. A switch or modulator (or load switch) (111) to excite the high-voltage pulse transformer that feeds the defibrillation energy to a pair of electrodes 114*a-b*. The transformer 113 is also driven by low voltage energy storage module 116 that generates supplementary energy through a bank of ultra-capacitors that are fed to the inputs of the transformer 113. Power is supplied by a battery 112. Additionally, a sensing module 115 includes sensing leads through which to monitor the inputs of the transformer 113, which is used by the sensing module 115 as feedback for switching the bank of ultra-capacitors, as required. The feedback is fed into a modulator (or load switch) 111 that controls the stimulus to the high-voltage pulse transformer 113, which results in better control and regulation of the energy delivered to the patient regardless of patient impedance.

Figure 5:
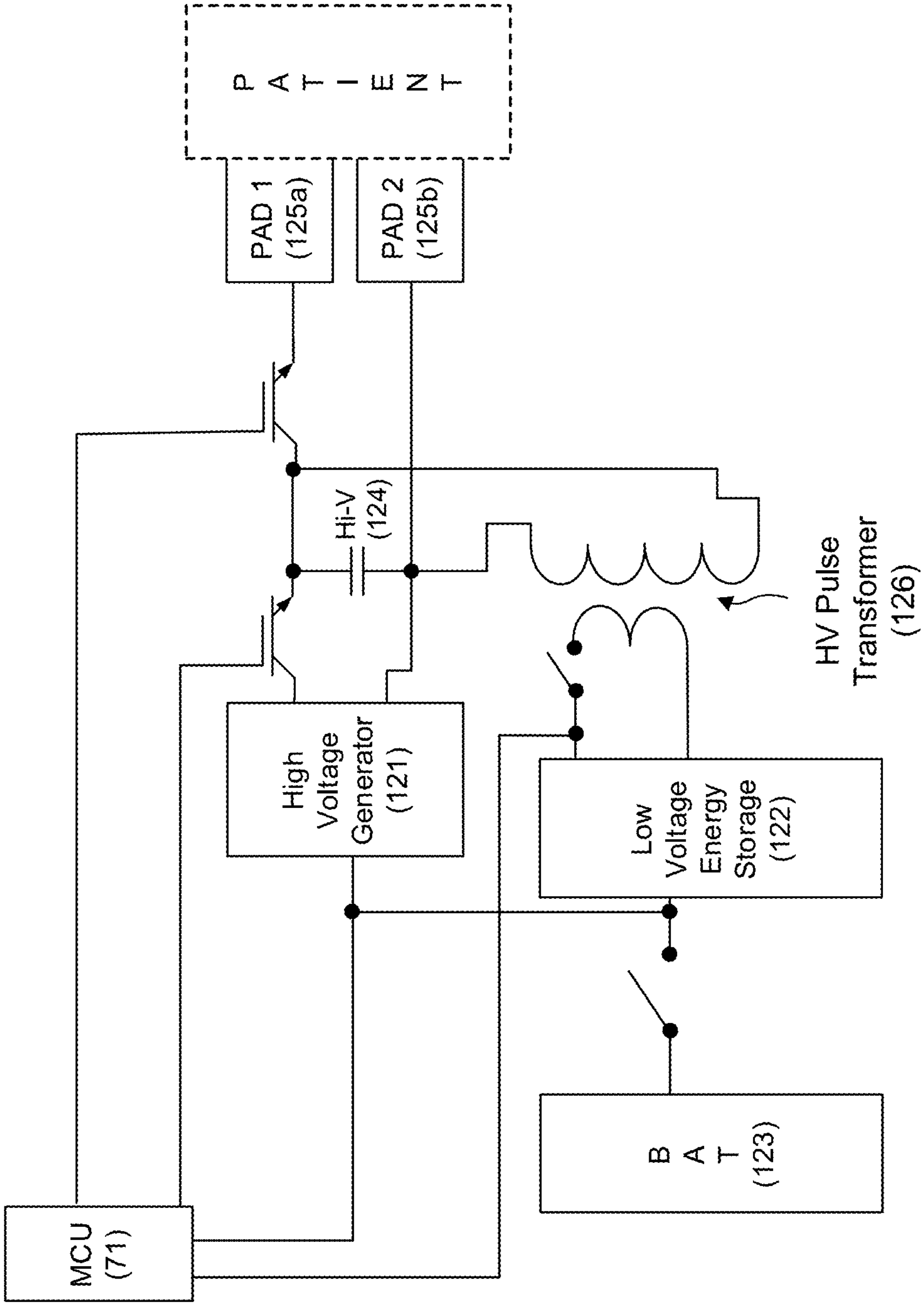
FIG. 5 is a schematic and block diagram showing a hybrid low voltage energy storage circuit for generating defibrillation waveforms energy in accordance with a further embodiment.

A hybrid energy sourcing approach can be taken by pre-charging a high-voltage capacitor in addition to a low-voltage pulse capacitor (or ultra-capacitor with pulse discharge capabilities). FIG. 5 is a schematic diagram showing a hybrid low voltage energy storage circuit 120 for generating defibrillation energy waveforms in accordance with a further embodiment. As before, the sensing and ECG circuits are omitted for clarity except as otherwise noted.

The defibrillation circuit 120 includes three basic components, a high-voltage generator (HVG) circuit 121, which serves the purpose to charge a high-voltage capacitor 124 that feeds the defibrillation energy to a pair of electrodes 125*a-b*. The high-voltage generator boost circuit 121 is supplemented by a low voltage energy storage (LVES) circuit 122 coupled through a high-voltage pulse transformer 126 that generates supplementary energy that is fed to the electrodes 125*a-b*. Power is supplied by a battery 123 through a switch. During discharge, some energy is supplied by the high-voltage capacitor 124 while additional energy is discharged into the patient from the LVES circuit 122 through the high-voltage pulse transformer 126. As the defibrillation energy is supplied by multiple sources, tradeoffs can be made between magnetic pulse transformer size and capacitor size, optimizing for the best available technology at the time. In this implementation, there is no control and feedback in the defibrillation pulse, which is a trade-off favoring simplicity and clinically reasonable efficacy versus complexity in favor of the appearance of perfection, albeit not the reality of it.

Figure 6:
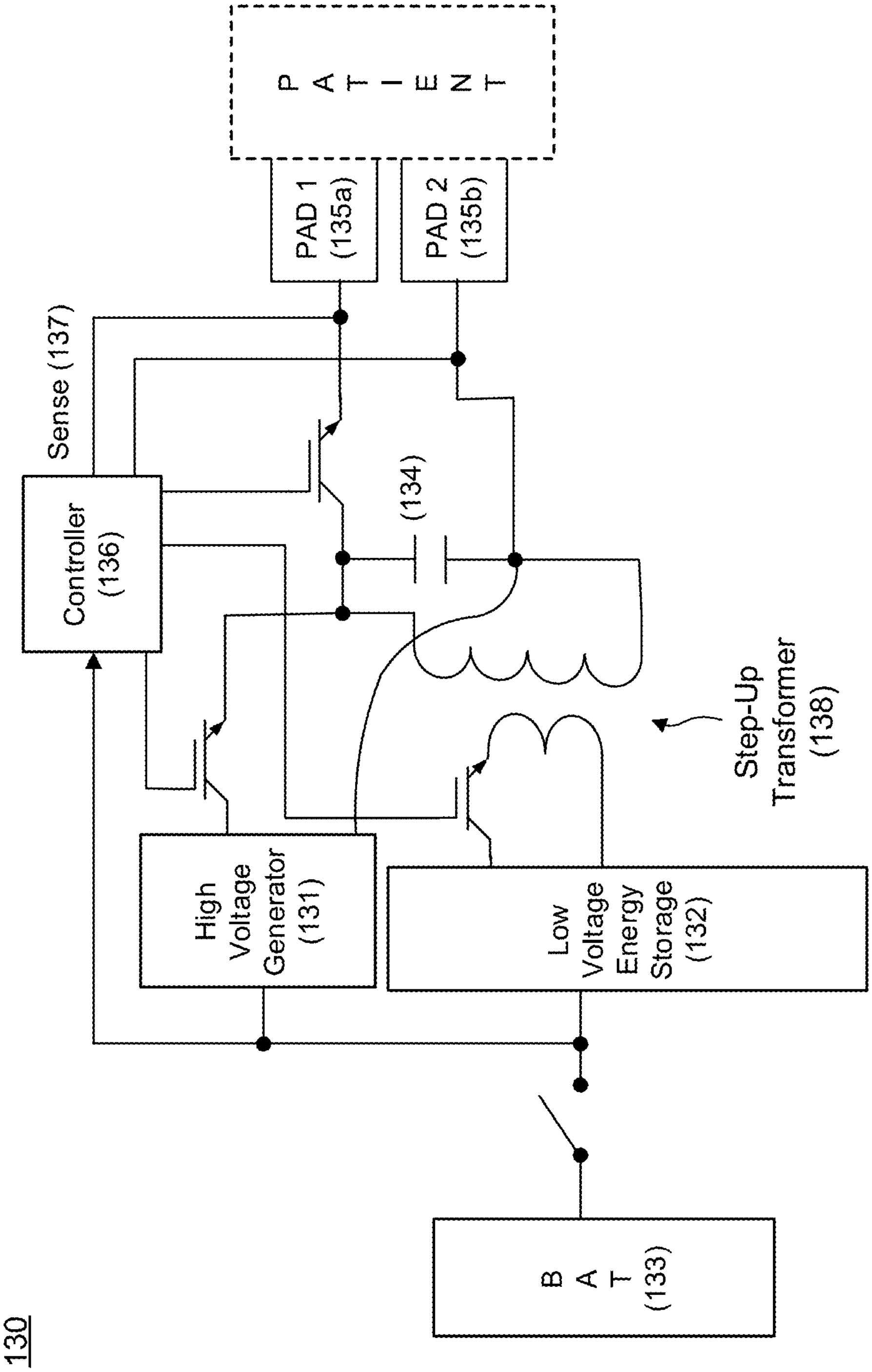
FIG. 6 is a schematic and block diagram showing a hybrid low voltage energy storage circuit for generating defibrillation waveforms energy with feedback in accordance with a further embodiment.

The foregoing hybrid energy delivery approach can be expanded upon with a controller that senses the therapy being delivered to the patient which allows active control and optimization of the defibrillation waveform depending on real-time impedance feedback. FIG. 6 is a schematic diagram showing a hybrid low voltage energy storage circuit 130 for generating defibrillation waveforms energy with feedback in accordance with a further embodiment. As before, the sensing and ECG circuits are omitted for clarity except as otherwise noted.

Here, the defibrillation circuit 130 includes four basic components, a high-voltage generator (HVG) circuit 131, which similarly serves to charge a high-voltage capacitor 134 that feeds the defibrillation energy to a pair of electrodes 135*a-b* when defibrillating. The low voltage energy storage (LVES) circuit 132 is supplemented by a bank of ultra-capacitors connected through a step-up pulse transformer 138 that generates supplementary energy that is fed to the inputs of the H-bridge. Power to the system is supplied by a battery 133. Additionally, a controller 136 includes sensing leads 137 through which to monitor the patient and the energy delivered. This waveform is used by the controller 136 as feedback for switching the bank of ultra-capacitors on and off to deliver supplementary energy as required. The controller 136 can modify the amount of energy being transferred to the patient in real time by shutting off or activating the low voltage storage element delivering additional energy to the patient only when needed resulting in a more accurate and efficacious defibrillation waveform. Long-duration defibrillation pulses, that is, a waveform with a duration much greater than 20 milliseconds (msec), can be counter-productive, as can occur in select patients with high resistance and impedance to current delivery and may in fact impede defibrillation or induce re-fibrillation. Contrarily, ultra-low resistance patients, such as small children, can manifest too brief of a defibrillation waveform, that is, a waveform with a duration of less than 4 msec, perhaps also impeding defibrillation efficiency.

Figure 7:
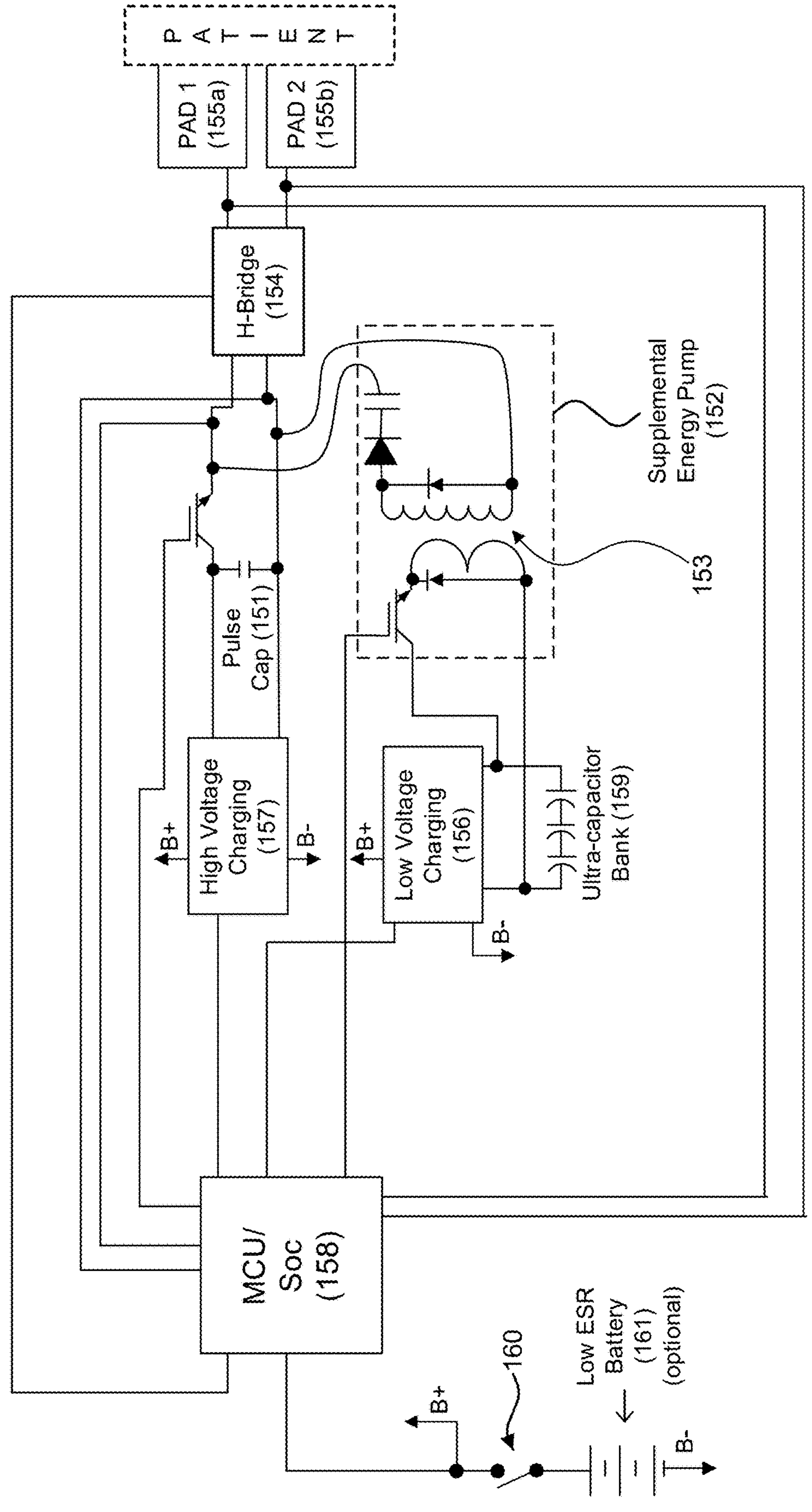
FIG. 7 is a schematic diagram showing a hybrid low voltage energy storage circuit for generating defibrillation waveforms energy with feedback and supplemental energy pump in accordance with a further embodiment.

The foregoing hybrid energy delivery approach with feedback can be improved upon with the addition of a supplemental energy pump. FIG. 7 is a schematic diagram showing a hybrid low voltage energy storage circuit 150 for generating defibrillation waveforms energy with feedback and supplemental energy pump 152 in accordance with a further embodiment. The circuit 150 is controlled by a microcontroller (MCU) or system-on-chip (SOC) 158 (hereafter, simply "MCU").

The supplemental energy pump 152 is able to dynamically couple energy stored in an optional low voltage charging module 156 into the patient through a transformer 153 incorporated into the supplemental energy pump 152 with high-voltage stored in a high-voltage charging module 157. This approach provides superior control of the energy delivery and waveform. The pumping action decreases the dielectric withstand voltage requirements and step-up transformer sizing requirements required by the hybrid low voltage energy storage circuit 150; thus, the respective breakdown voltage and voltage increase can be significantly lower here when compared to a conventional AED intended for long term reusability, that is, non-disposable multiple victim use. In turn, lower voltage and capacitance components can be safely used throughout the hybrid low voltage energy storage circuit 150, including a lower capacity power source. Moreover, given the dynamic nature of the circuit, the circuit 150 is capable of high efficacy on a wide variety of patients and allows additional flexibility for the internal components to be selected to optimize for cost, size, and weight. This approach also features an optional H-bridge 154 coupled output to further simplify the generation of a biphasic pulse or correct for incorrect (reversed) placement of the electrodes 155*a-b*.

As with conventional AEDs, defibrillation energy is stored in a pulse capacitor 151, which can be the largest component and the one requiring specific housing considerations as discussed infra. A high-voltage charging module 157 conventionally increases voltage drawn from a battery 161 with a low equivalent series resistance (ESR) rating, drawn through a rectification circuit (not shown) to convert the energy into DC, which is then stored in the pulse capacitor 151. However, the low voltage charging module 156 is coupled to a bank of ultra-capacitors 159, which only need to be rated to handle modest low voltages in the range of 2.5V-48V with a capacitance range yielding up to 360 J, which would be in the range of 96 Farads (F) for 2.5V and 0.26 F for a voltage of 48V. The bank of ultra-capacitors 159 is preferably arranged in series, series-parallel or parallel configurations to store up to 360 J of energy or more.

The supplemental energy pump 152 is enabled by the MCU 158 when the H-bridge 154, if present, is discharging energy into the patient to maintain the defibrillation shock for several milliseconds; the bank of ultra-capacitors 159 have a high discharge rate that allows the low voltage charging module 156 to additively augment the defibrillation energy during shock delivery. The supplemental energy pump 152 allows the pulse energy to be stepped up during delivery by interfacing with the H-bridge's input leads. The MCU 158 can monitor the supplementing energy being delivered by the low voltage charging module 156 over a pair of sensing connections that interface with the H-bridge's output leads.

With this form of energy supplementation, a lower rated high-voltage pulse capacitor 151 can be used than found in conventional AEDs, and, given the expected disposable single use operation of an AED using the hybrid low voltage energy storage circuit 150, the circuit 150 can be powered using a low cost and lightweight battery 156, rated in the range of 2.5V-48V. In turn, the use of such a small form factor battery allows an AED using the hybrid low voltage energy storage circuit 150, such as discussed with reference to FIGS. 10-18, to be both disposable and carriable in an average pocket presuming innovations in accompanying housing considerations as later described. In a further embodiment, the battery 161 is supplemented with a manual switch 160 to create an open circuit when not in use, which conserves battery and component life and simplifies the design. In a still further embodiment, an AED using the hybrid low voltage energy storage circuit 150 includes a battery charging circuit (not shown) with which to recharge the battery 161. A similar component rating reduction of the pulse capacitor circuit would be applicable where the foregoing circuits are adapted for use in a non-portable clinical-grade defibrillator and in an implantable defibrillator, the latter of which could also benefit from a battery supply rating reduction.

Figure 8:
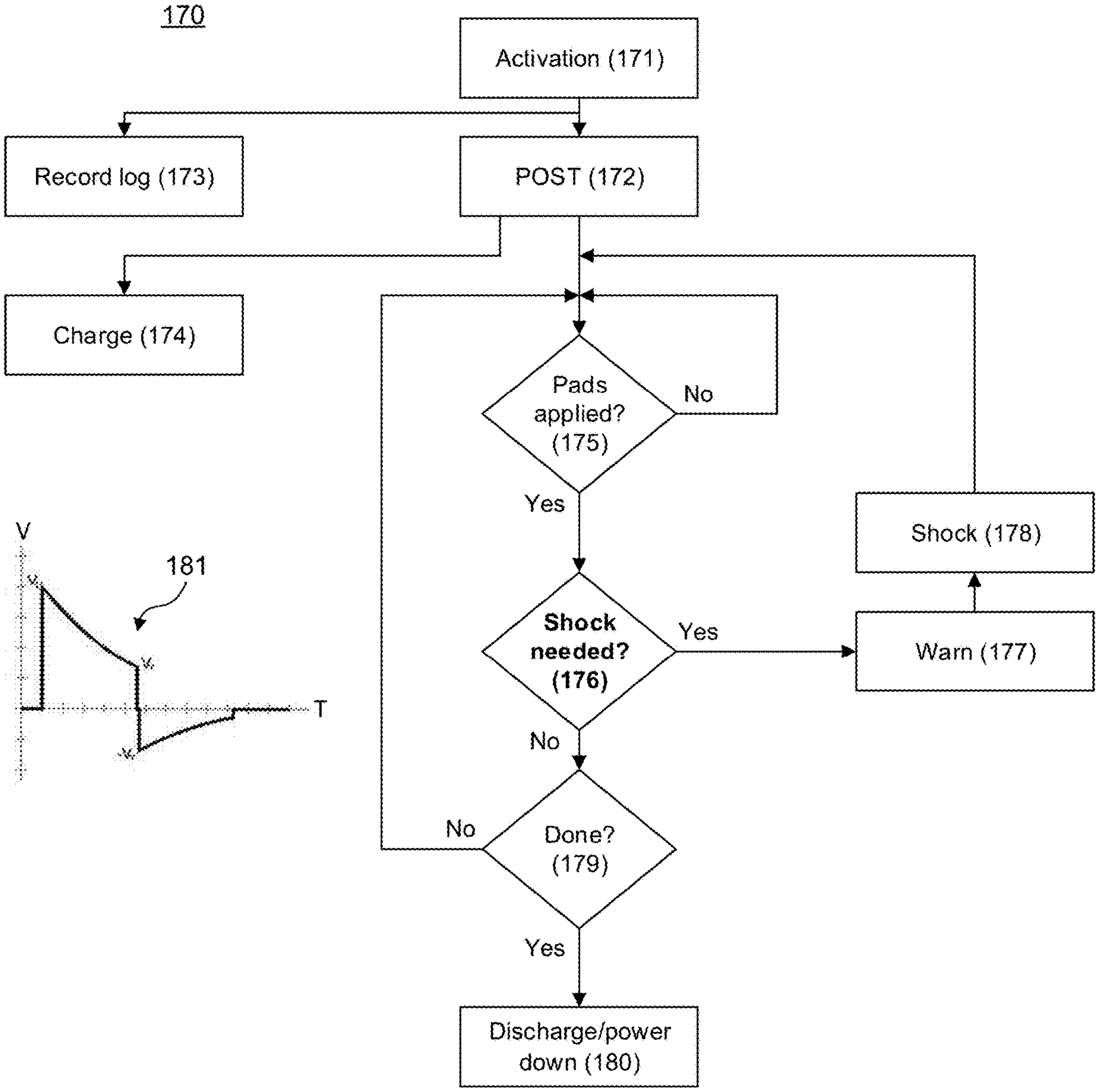
FIG. 8 is a flow chart showing a method for operating a disposable single use pocketable AED in accordance with one embodiment.

A disposable pocketable AED using the hybrid low voltage energy storage circuit 150 is intended to be available 24/7/365 and easy to use with little to no training required. FIG. 8 is a flow chart showing a method 170 for operating a disposable pocketable AED in accordance with one embodiment. To start, the AED is activated (step 171) by the user pressing the "On" switch, or similar control, after which the AED executes a power-on self-test (POST) (step 172).

Figure 9:
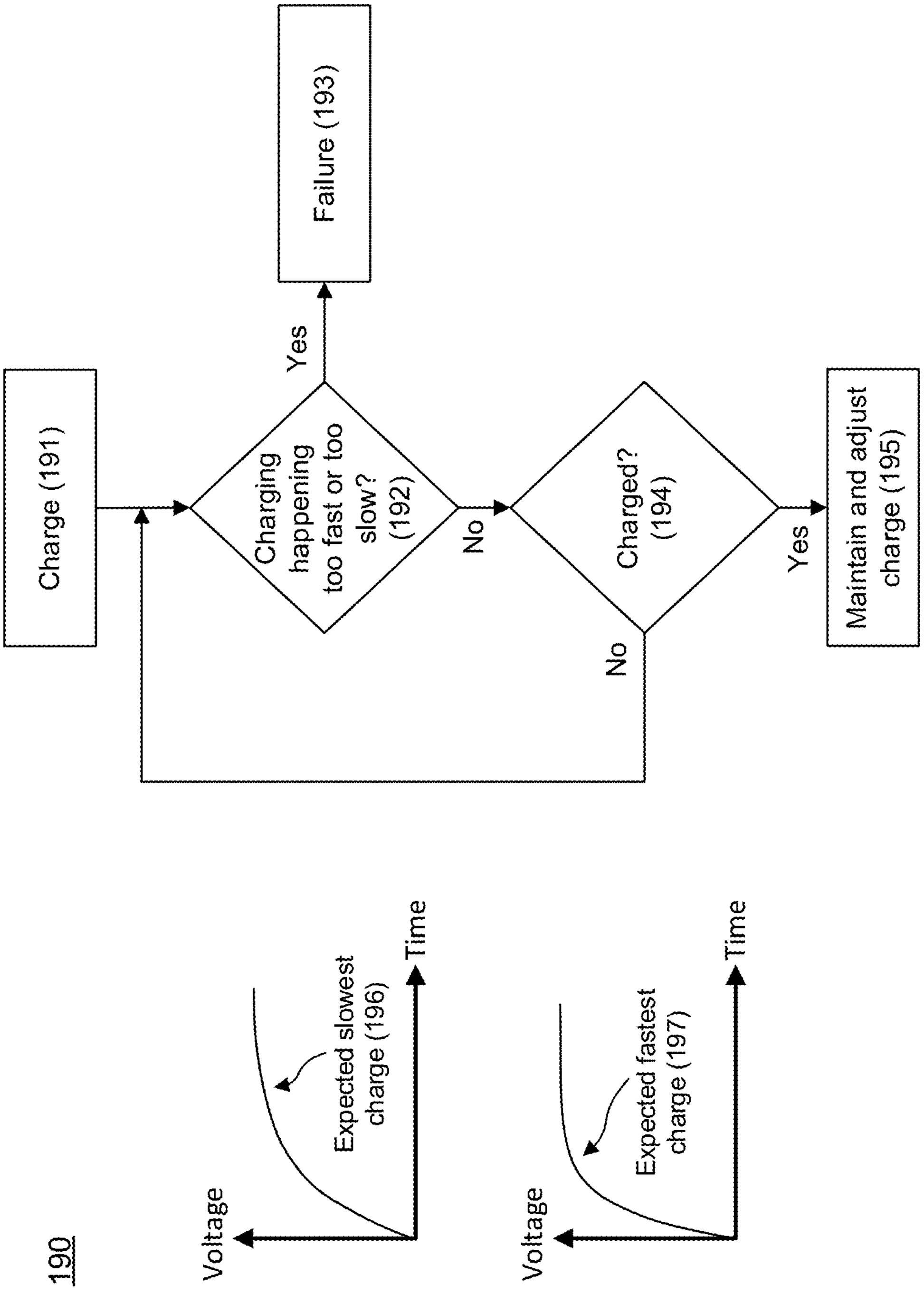
FIG. 9 is a flow chart showing a charging routine with out-of-bounds failure detection for use in the method of FIG. 8.

Following successful POST (power on self test) (step 172), a record of the AED's activation is made in an onboard log (step 173) and the pulse capacitor is pre-charged to a conservative level (step 174) by the high-voltage charger module and the low voltage energy storage circuit, as further described below with reference to FIG. 9. However, in a further embodiment, the record can be generated after the activation (171), while the charge is initiated after POST (172). The state of the electrode pads is determined, and the methodology only proceeds once the pads are applied (step 175) as further defined infra. The AED detection algorithm determines whether a shockable rhythm is present (step 176).

Provided a shockable rhythm is sensed (step 176), the AED issues a warning to the user (step 177) and a defibrillation shock is delivered (step 178). The defibrillation shock is delivered as a high-voltage therapeutic waveform 181, preferably as a biphasic waveform, such as a biphasic truncated exponential (BTE), pulsed biphasic, and rectilinear biphasic waveform, modified biphasic, arbitrary or, alternatively, as a monophasic waveform. Other defibrillation waveforms are possible. Once the shock has been delivered, the device determines whether a normal rhythm has been restored and, if so, the methodology is done (step 179) and the AED will discharge any remaining energy in the pulse capacitor or low energy supplementing circuit and power down (step 180) after up to 30 minutes of a non-VF rhythm. In some cases, several defibrillation shocks are required with the AED delivering biphasic defibrillation shocks. Typically, 150 J biphasic shocks are delivered and may be delivered up to 6 times if needed. In an alternative embodiment, the initial energy level for defibrillation begins at or around 120 J and either repeats or escalates for the second and subsequent defibrillation shocks up to a maximum of at or around 360 J. In the use of escalation, the defibrillation energy is automatically adjusted by the AED with each subsequent defibrillation shock. In a further embodiment, the polarity of the defibrillation shock is reversed on the third shock (or any subsequent shock following the first shock) should no restoration of a non-shockable rhythm occur. In a further embodiment, the AED can automatically limit the number of shock re-attempts permitted, as after three defibrillation shocks, resuscitation of the victim 18 becomes unlikely.

In a further embodiment, as part of the process of delivering the defibrillation shock (step 178), the AED measures patient impedance during application of the defibrillation shock through the sensing circuit and adjusts one or more of the energy, voltage, and pulse width of the defibrillation waveform 181 in real time to generate optimal defibrillation therapy, where the x-axis represents time (T) and the y-axis represents voltage (V). Knowledge of patient impedance is crucial in a traditional design, which is used to determine the energy required to pre-charge the high-voltage pulse capacitor to an appropriate level and to aid in realizing an appropriate energy deliver waveform. In practice, patient impedance changes during the shock, so conventional impedance-based pre-charge circuits have limited usefulness in achieving effective defibrillation. For instance, the impedance of a ten-year-old child is around 20 Ohms, whereas a 200-pound, middle-aged male typically has an impedance of about 75 Ohms. For both individuals, a waveform of 5-15 msec is likely necessary for effective defibrillation but their defibrillation pulse timing, and pre-charge parameters are different. Moreover, impedance on the skin's surface typically decreases as defibrillation therapy progresses. Thus, MCU 71 (shown in FIG. 2) interfaces to the sensing circuit to continually measure impedance in real time and adjusts parameters in the high-voltage energy delivery module 79 and the low voltage energy supplementing module 80 to alter energy, voltage, and pulse width (duration). Other parameters are possible.

For instance, an exemplary biphasic waveform is defined with an asymmetrical 65% tilt from a leading-edge voltage $V_L$ and trailing edge voltage $V_T/-V_T$ with a polarity reversal halfway through the waveform. Patient impedance can affect the duration of the waveform where increased impedance means longer pulse width, lower voltage, or less energy to the heart, and decreased impedance means shorter pulse width, higher voltage, or more energy to the heart (unless patient impedance changes after the impedance is sensed). The most efficacious way to ensure correct energy delivery is to monitor and adjust the therapy in real time. One or more of these parameters can be adjusted by the MCU in real time to alter the amount of primary or supplementary energy contour of the shock to reflect the ideal target therapy represented by the biphasic waveform.

The AED utilizes low voltage energy storage to supplement the defibrillation circuit's pulse capacitor. FIG. 9 is a flow chart showing a charging routine 190 for use in the method 170 of FIG. 8. The primary and supplementary defibrillation energy is based on a high-voltage therapeutic waveform, such as the biphasic waveform shown in FIG. 8, which can be maintained by the microcontroller 71 (shown in FIG. 2) in its memory store. In a further embodiment, the AED measures patient impedance during application of the defibrillation shock and adjusts one or more of the energy, voltage, and pulse width of the defibrillation waveform 181 in real time to generate optimal defibrillation therapy and, in a still further embodiment, the AED can revise the optimal defibrillation therapy during the second and, if needed, third defibrillation pulses in the event that earlier defibrillation attempts have failed to restore normal cardiac rhythm. During charging of the pulse capacitor (step 191), the microcontroller compares the primary defibrillation energy and the supplemental energy to the energy required to deliver the defibrillation waveform 181. If the charging of the pulse capacitor is happening either too fast or too slow (step 192), as based on a plot of an expected slowest charging rate 196 and a plot of an expected fastest charging rate 197, a failure condition exists (step 193). The charging rate can be bounded, for instance, based on a pair of thresholds that respectively define upper and lower bounds of charging rate, such that a charging rate that exceeds the upper bound is considered too fast and a charging rate that falls below the lower bound is considered too slow. A failure condition in the expected charging rate can be useful in identifying potential problems with the charging circuit. An overly fast charging rate could indicate that capacity of pulse capacitor has decreased and may not have enough energy to perform its function when fully charged. An overly slow charging rate falling below the lower bound could indicate an excessive energy leakage in the circuit, which typically ends up being expressed as heat. In both charging rate plots, the x-axes represent time, and the y-axes represent voltage. Otherwise, charging continues until the circuit is charged (step 194), after which the microcontroller maintains and adjusts the charge in the pulse capacitor as needed (step 195).

Figure 10:
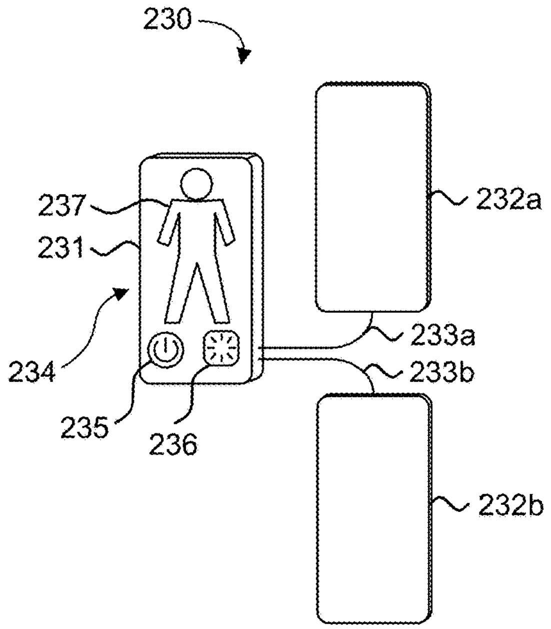
FIG. 10 is a front view showing a disposable single use pocketable AED with dual free-floating electrodes in accordance with one embodiment.

FIG. 10 is a front view showing a disposable single use pocketable AED with dual free-floating electrodes in accordance with one embodiment. The AED 230 combines a highly portable form factor with high and low voltage energy storage circuits that deliver defibrillating energy out of only modest lightweight battery capacity that is isolated from the defibrillation pads. The AED 230 advantageously uses low voltage energy storage, as discussed supra with reference to FIG. 2 et seq., to supplement the high-voltage charger circuit used to charge the pulse capacitor. This innovation allows the circuit to be powered with a low cost and lightweight battery more suitable to the housing or case. Further, the high-voltage charger circuit and pulse capacitor can be down-rated from the high capacitance levels utilized in conventional designs, all of which significantly decreases cost and size, thereby making single-use and device disposability possible and, importantly, a pocket size, AED.

The AED 230 is housed in a small lightweight housing 231, about the size and weight of a mobile telephone, that is, in the range of 2.25 to 3.625 inches wide, 5.25 to 7 inches tall, and 0.25 to 1.875 inches deep and a weight in the range of 130 to 945 grams. Other sizes and form factors are possible. The pair of free-floating electrodes 232*a-b* are connected to the housing 231 by a pair of flexible leads 233*a-b*. A planar laminated high energy pulse transformer is incorporated into each electrode 232*a-b*, as further discussed infra with reference to FIG. 19. Each electrode 232*a-b* is coated with an adhesive hydrogel that ensures proper contact with the victim's skin. The electrodes 232*a-b* are for a single patient use only. The front of the AED 230 can include a user interface 234 designed to optimize user understanding that includes a set of visual instructions 237. Optionally, the AED 230 can be equipped with an alternative embodiment including a speaker (not shown) to generate voice prompts.

The AED 230 includes a streamlined and simple user interface that facilitates understanding and proper use during an emergency by family or friends who may be confused and frightened by the SCA of someone they know. Power can be controlled by a simple power switch 235 that can be unnecessary to push but occurs automatically with pad removal. The status of the AED 230 is intuitively provided by a visual indicator 236 that changes color depending upon the state of the AED, for instance, through a display of "red," "yellow" and "green" to respectively indicate device activated but not attached to the patient, device attached and pulse capacitor charging, and a ready-to-shock condition. Other colors, forms and types of indicators are possible. In a further embodiment, the AED 230 includes mobile communications capabilities by which to automatically summon medical assistance, generally by calling 9-1-1 or the equivalent in most localities, upon the sensing of a shockable rhythm. The mobile communications capabilities integrated into the AED 230 by including appropriate circuits and components or through a special features module providing the mobile communications capabilities to the AED. The AED could also receive mobile communications capabilities through a wireless interface, such as WiFi or Bluetooth, over which the AED can communicate to a mobile phone or wide area network, such as the Internet, and relay a 9-1-1 call. Alternatively, a mobile phone or device could be supplemented with the features of the AED 230.

Figure 11:
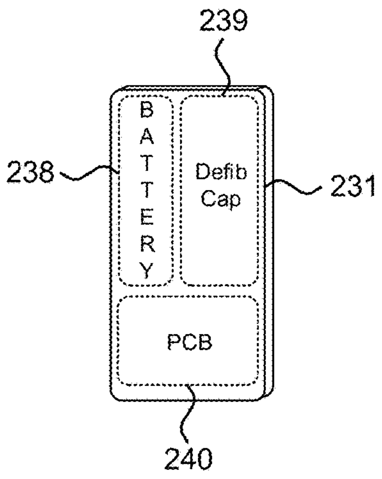
FIG. 11 is a cut-away view showing block component groups contained within the disposable single use pocketable AED of FIG. 10.

FIG. 11 is a cut-away view showing block component groups contained within the disposable single use pocketable AED 230 of FIG. 10. The AED's circuit is provided on a printed circuit board (PCB) 240 contained within the housing 231, which also contains a low-cost, high-energy density battery 238 (optionally, a primary cell) and a pulse capacitor 239.

Figure 12:
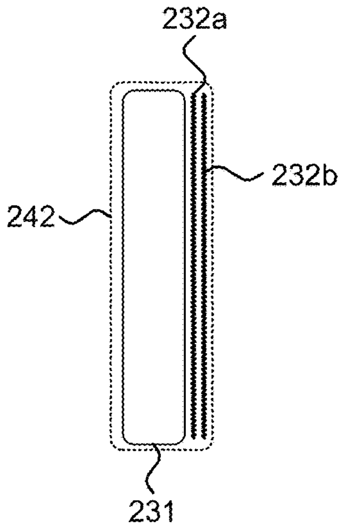
FIG. 12 is a side view showing the disposable single use pocketable AED of FIG. 10 with the housing and dual free-floating electrodes stowed in a carrying case.

FIG. 12 is a side view showing the disposable single use pocketable AED 230 of FIG. 10 with the housing and dual free-floating electrodes stowed in a carrying case 242 whose opening can be of several means, such as described in detail below with respect to FIGS. 12-27. The AED 230 is intended to be easily carried in a pocket and could be carried in a purse, backpack, glovebox, golf bags, and so forth, or on a refrigerator door, so as to enable the AED 230 to be conveniently on-hand in case of an SCA situation in the same manner that most people have their mobile phone on-hand.

Figure 13:
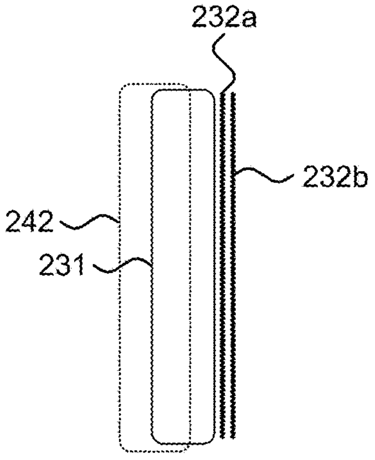
FIG. 13 is a side view showing the disposable single use pocketable AED of FIG. 10 with the housing and dual free-floating electrodes partially deployed from the carrying case.

FIG. 13 is a side view showing the disposable single use pocketable AED 230 of FIG. 10 with the housing and dual free-floating electrodes partially deployed from the carrying case 242. The pair of free-floating electrodes 232*a-b* share a similar front profile with the housing 231. The housing 231 and electrodes 232*a-b* slide out of the carrying case 242 when being deployed.

Figure 14:
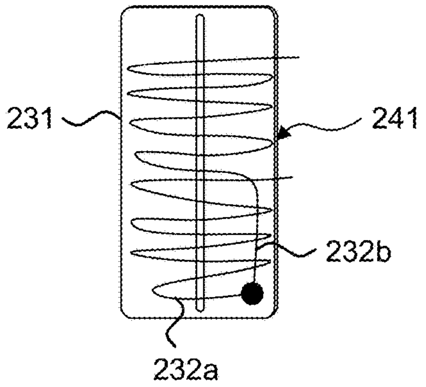
FIG. 14 is a back view showing the cable management system of the disposable single use pocketable AED of FIG. 10.

FIG. 14 is a back view showing the cable management system 241 of the disposable single use pocketable AED 230 of FIG. 10. A cable management system 241 is used to store the leads 232*a-b* inside of the housing 231, where the leads are internally retracted by the smart cable management system 241 until needed.

Figure 15:
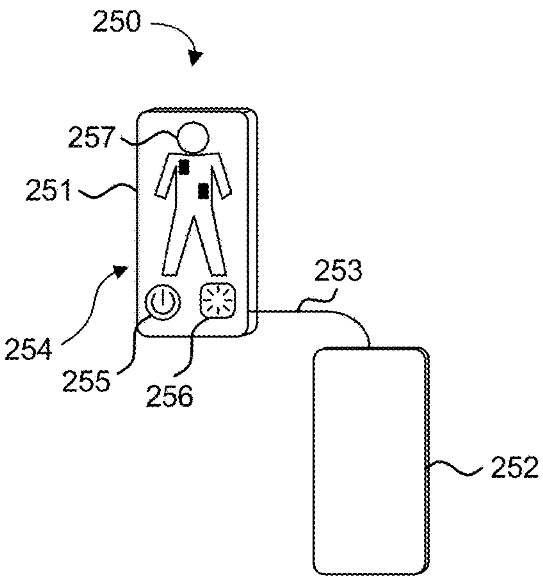
FIG. 15 is a front view showing a disposable single use pocketable AED with a single free-floating electrode in accordance with one embodiment.

One of the dual free-floating leads 232*a-b* can be eliminated by providing an electrode pad surface on the AED's housing. FIG. 15 is a front view showing a disposable single use pocketable AED 250 with a single free-floating electrode 252 in accordance with one embodiment. As before, the AED 250 is housed in a small lightweight housing 251, but only one free-floating electrode 252 is connected to the housing 31 by a single flexible lead 25.

Figure 16:
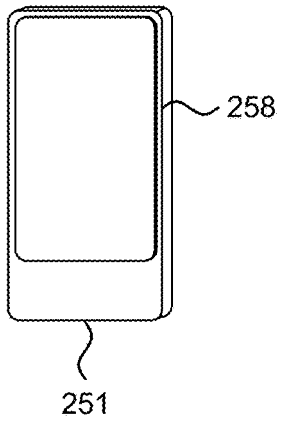
FIG. 16 is a rear view showing the integrated electrode of the disposable single use pocketable AED of FIG. 15.

FIG. 16 is a rear view showing the integrated electrode 258 of the disposable single use pocketable AED 250 of FIG. 15. An integrated electrode pad 258 is provided on a rear-facing surface of the housing 251. A planar laminated high energy pulse transformer is incorporated into each electrode 252, 258, as further discussed infra with reference to FIG. 19. Both the single free-floating electrode 252 and integrated electrode 258 are coated with an adhesive conductive hydrogel that ensures proper contact with the victim's skin. The front of the AED 250 similarly has a user interface 254 designed to optimize user understanding that includes a set of visual instructions 257. Optionally, the AED 250 can be equipped with a speaker (not shown) to generate voice prompts. Power is again controlled by an "On" switch or optionally an activation circuit 255 and the status of the AED 250 is provided by a visual indicator 256. The AED's circuit is provided on a PCB (not shown) contained within the housing 251, which also contains a low-cost, high-energy density battery (not shown) and pulse capacitor (not shown).

Figure 17:
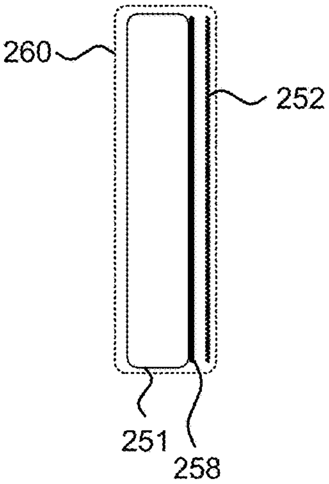
FIG. 17 is a side view showing the disposable single use pocketable AED of FIG. 10 with the housing and single free-floating electrode stowed in a carrying case.

FIG. 17 is a side view showing the disposable single use pocketable AED 250 of FIG. 10 with the housing 251 and single free-floating electrode 252 stowed in a carrying case. The single free-floating electrode 252 shares a similar profile with the housing 251.

Figure 18:
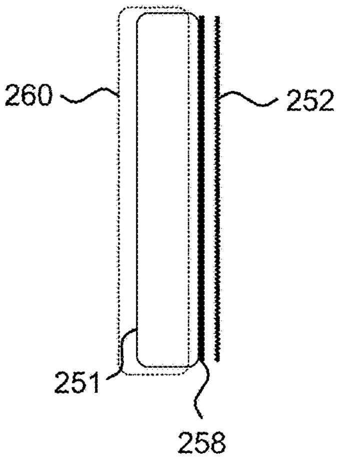
FIG. 18 is a side view showing the disposable single use pocketable AED of FIG. 10 with the housing and single free-floating electrodes partially deployed from the carrying case.

FIG. 18 is a side view showing the disposable single use pocketable AED of FIG. 10 with the housing and single free-floating electrodes partially deployed from the carrying case. The housing 251 and electrode 252 slide out of the carrying case 260 when being deployed. A smart cable management system (not shown) is also used to store the single lead 253 inside of the housing 251, where the lead is internally retracted by a cable management system until needed. The cable management system is further described below in detail with respect to FIGS. 25 and 26.

Figure 19:
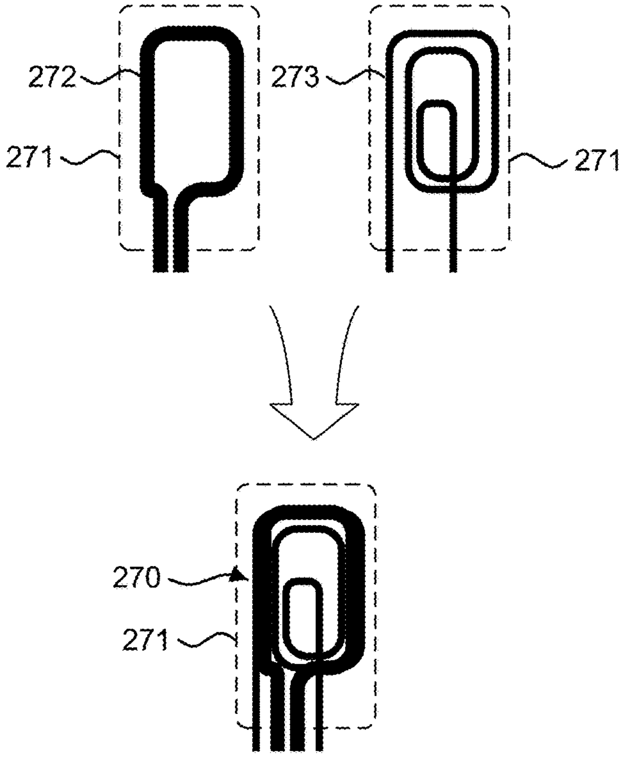
FIG. 19 is a top view diagram showing an electrode pad assembly for use in the disposable single use pocketable AEDs of FIGS. 10 and 15.

FIG. 19 is a top view diagram showing an electrode pad assembly 271 for use in the disposable single use pocketable AEDs 230, 250 of FIGS. 10 and 15. Each electrode contains an embedded planar laminated high energy pulse transformer. This type of transformer exhibits high power density by functioning at high switching frequencies, while packaged in a low profile with larger surface area, thereby preventing overheating. In each electrode assembly 271, a primary winding 272 and a secondary winding 273 are laminated together into a planar transformer 270 with a jumper that is soldered, welded, crimped, or otherwise electrically conducted together.

Figure 20:
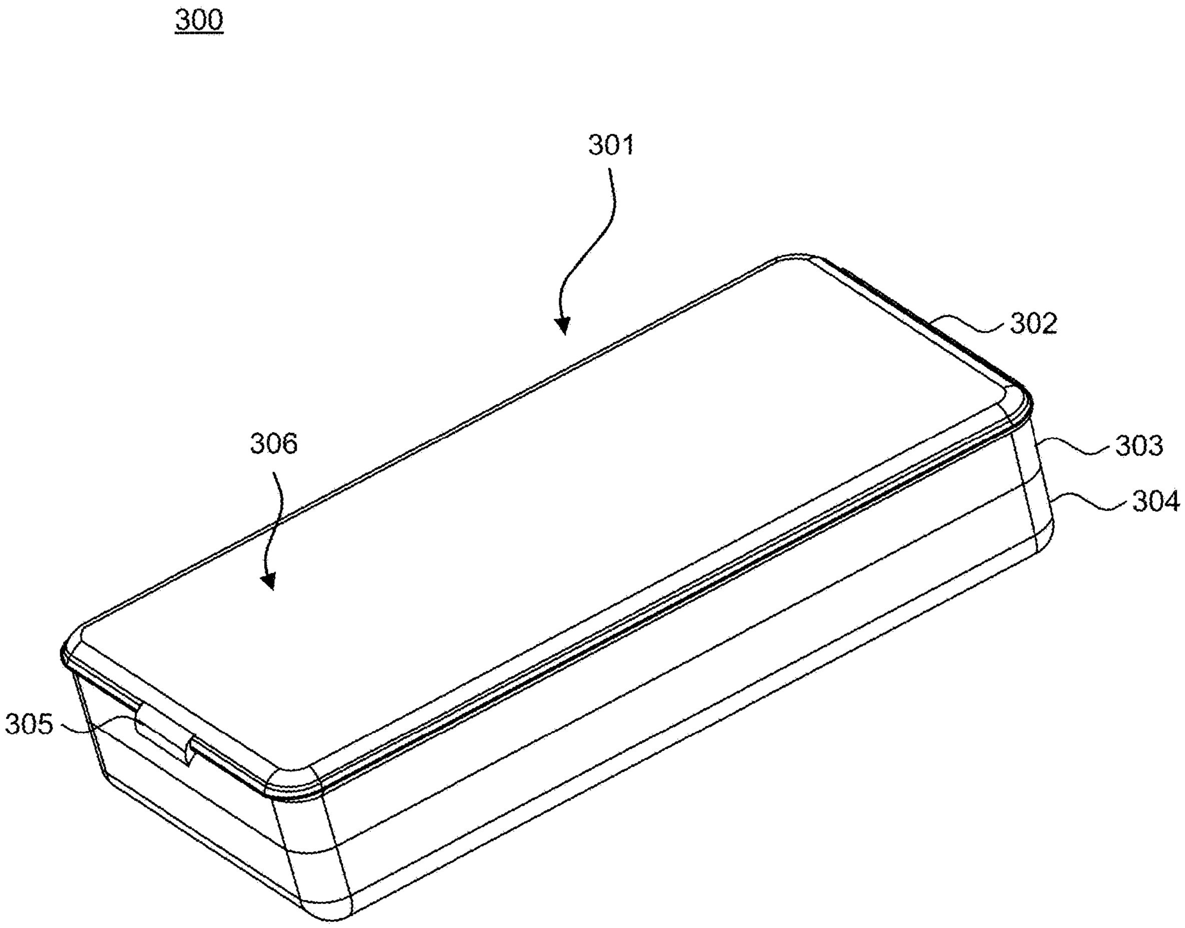
FIG. 20 is a perspective view diagram showing a case for a disposable, single use, pocketable AED.

To ensure the AED is small and light enough to easily carry, in a pocket, the case must also be small and light weight, as well as easy to use. Pads must be able to be effortlessly removed from the casing. Moreover, the case may be designed to trigger charging either upon removal or upon application of the electrode pads that automatically initiates condition or event detection and defibrillation. FIG. 20 is a perspective view 300 diagram showing a case 301 for a disposable, single use, pocketable AED. The case 301 can include a circuit enclosure 304, an electrode enclosure 303, and a cover 302. Each of the circuit enclosure 304, electrode enclosure 303, and cover 302 can have a rectangular shape and be made from metal, rigid plastic, flexible plastic, or another polymer. The case 301 can have a size in the range of 2.25 to 3.625 inches wide, 5.25 to 7 inches tall, and 0.25 to 1.875 inches deep and a weight in the range of 130 to 945 grams. Other shapes, sizes, and materials are possible.

The circuit enclosure 304 can house the energy storage circuit for generating defibrillation waveforms energy. In one embodiment, the circuit can be housed in a receptacle, which can be made from the same or different materials than the case, and affixed to a bottom surface of the electrode enclosure facing the circuit enclosure or a bottom surface of the circuit enclosure. The circuit is further described above with respect to FIGS. 3-7. The electrode enclosure 303 can house the electrode pads for placement on a patient and delivery of the defibrillation waveforms energy. The electrode enclosure can be stacked above the circuit enclosure 304 and can be fused to the circuit enclosure 304 using laser, ultrasonic, or radio frequency welding. Other methods for fusion are possible, such as joining the electrode enclosure and the circuit enclosure via fasteners.

In one example, the circuit enclosure 304 can include a bottom surface with four walls perpendicularly affixed around a perimeter of the bottom surface to form a cavity in which the energy storage circuit is housed, while the electrode enclosure 303 can also include a bottom surface with four walls perpendicularly affixed around a perimeter of the bottom surface to form a cavity in which the electrode pads are stored. The electrode enclosure 303 can be stacked on top of the circuit enclosure 304, and the bottom surface of the electrode enclosure 303 can be fused to a top surface of the circuit enclosure 304 walls, opposite the bottom surface of the circuit enclosure 304, to ensure the circuit enclosure and electrode enclosure are connected. When stacked, fused, fastened, or welded, access to the circuit enclosure is not possible, while still allowing access to the cavity of the electrode enclosure. The circuit enclosure 304 and the electrode enclosure 303 can have the same or different sizes. When different sizes, the circuit enclosure 304 can have a deeper cavity than the electrode enclosure, for example.

In a further embodiment, the electrode enclosure and the circuit enclosure can be stacked and snapped together to prevent separation. In one example, feet can be formed on a bottom surface of the electrode enclosure, such as one in each corner formed by the four walls. The circuit enclosure can include openings for the feet in each of the four corners formed by the walls of the circuit enclosure. When stacked, the feet are snapped into the openings to secure the electrode and circuit enclosures.

The cover 302 can be shaped and sized to fit over the cavity of the electrode enclosure 303 in which the electrode pads are housed and can allow or prevent access to the cavity depending on a position of the cover 302. In one embodiment, the cover 302 can be affixed to one or more walls of the electrode enclosure 303 and can include a fastener 305 on at least one side to keep the cover in a closed position for securing the electrode pads in the cavity of the electrode enclosure. The fastener 305 can include a latch, snap, or button, as well as other types of fasteners, and can be affixed to the cover on a side opposite the side affixed to the electrode enclosure 303. At a minimum, the fastener must prevent opening of the cover 302 when in a "closed" or "locked" position. Upon manual pressure, the fastener 305 is released to allow the cover to open and provide access to an interior of the electrode enclosure.

In a further embodiment, a two-step manual maneuver of any of the above fasteners can be utilized to ensure that accidental opening of the pads compartment does not occur. For example, a snap and a latch can be used to prevent accidental opening and ensure that the opening is intentional.

A magnet (not shown) or manual trigger (not shown) can be placed on or in contact with the cover 302 to power up the device and commence charging of the energy storage circuit for delivery of energy to the pads when the AED is to be used on a patient. Specifically, when the fastener 305 is unlocked, the pads are removed, or the cover 302 is opened, the magnet is triggered and charging of the energy storage circuit is initiated. The magnet can trigger a reed switch. If, for some reason, the cover is unintentionally opened despite the safety precautions of the fasteners, the automatic charging can terminate upon closing of the case.

To improve the usability of the AED by inexperienced, confused or frightened lay users, a top surface of the cover 302 can include a user interface 306 that does not require a screen or buttons. This approach reduces confusion amongst various population groups such as low English literacy or the elderly, as well as those confused over what happens during SCA. The significant upside to this approach is that the simpler the interface, the quicker a shock is delivered and the likelihood of survival increases. The user interface 306 can include simple instructional wording and artwork for utilizing the AED, such as "Open" with an arrow pointing to the location of opening. In one embodiment, the instructions can be provided on the relevant parts of the case by printing the instructions on the case, generating labels or stickers with the instructions for sticking on the case, or by embossing the instructions on the case. Such instructions, which can include one or more words, can be placed on the case itself, pouch, or electrode pads.

Further, the user interface 306 can include lights that signal various instructions and/or alerts to the user. The user interface 306 can also be included on an interior surface of the cover 302, as well as on a back surface of the case 301. Other locations for the user interface are possible. Surfaces 353 or the inside of 303 can also serve as the user interface. In addition to the visual interface, a tonal warning can sound prior to the delivery of shock. The elimination of verbal instructions further reduces confusion amongst various populations such as low English literacy or the elderly. However, in a further embodiment, the user interface can include a display screen or manual buttons (not shown).

Figure 21:
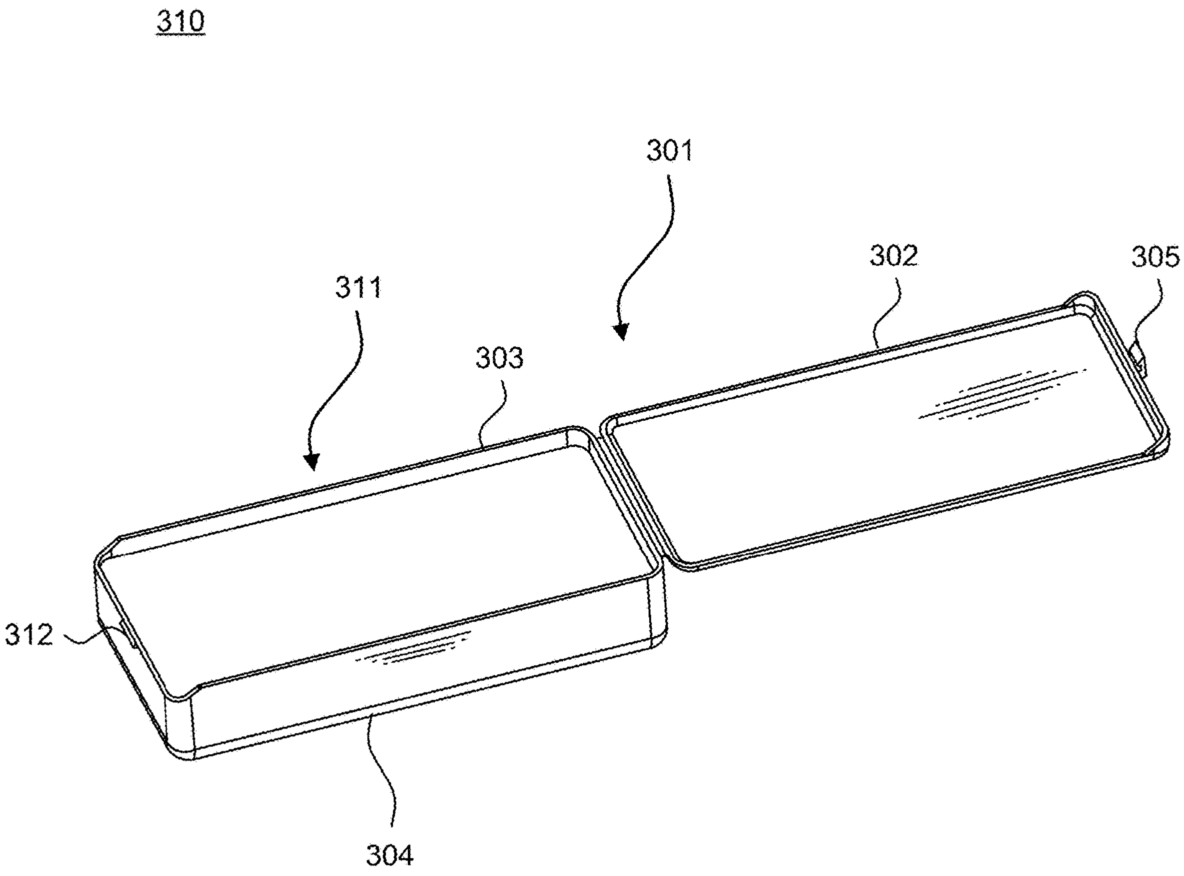
FIG. 21 is a perspective view diagram showing the case of FIG. 20 in an open position.

When the AED is needed, the cover can be opened to access the electrode pads. FIG. 21 is a perspective view 310 diagram showing the case 301 of FIG. 20 in an open position. The cover 302 is attached on one end to a wall of the electrode enclosure 303. The cover 302 can be attached, on one side, via a hinge, living hinge, screw, bracket, or other mechanism that will allow the cover to rotate to open and closed positions to allow and prevent access to the electrode enclosure cavity, respectively. Rotation of the cover can occur on any side of the cover to allow opening of the case lengthwise or widthwise. The cover 302 can also be attached to the wall of the electrode enclosure 303 via a hinge. When the cover 302 is rotated in an open position, access to a cavity 311 of the electrode enclosure is available. A fastening device 305, such as a clasp or latch can be affixed to an end of the cover opposite the end affixed to the electrode enclosure to prevent unintended opening of the cover 302. In one embodiment, the fastening device can include a V-shape or check mark shaped mechanism to fasten over a stopper 312 affixed to an outer surface of the electrode enclosure wall opposite the wall to which the cover is affixed.

Figure 22:
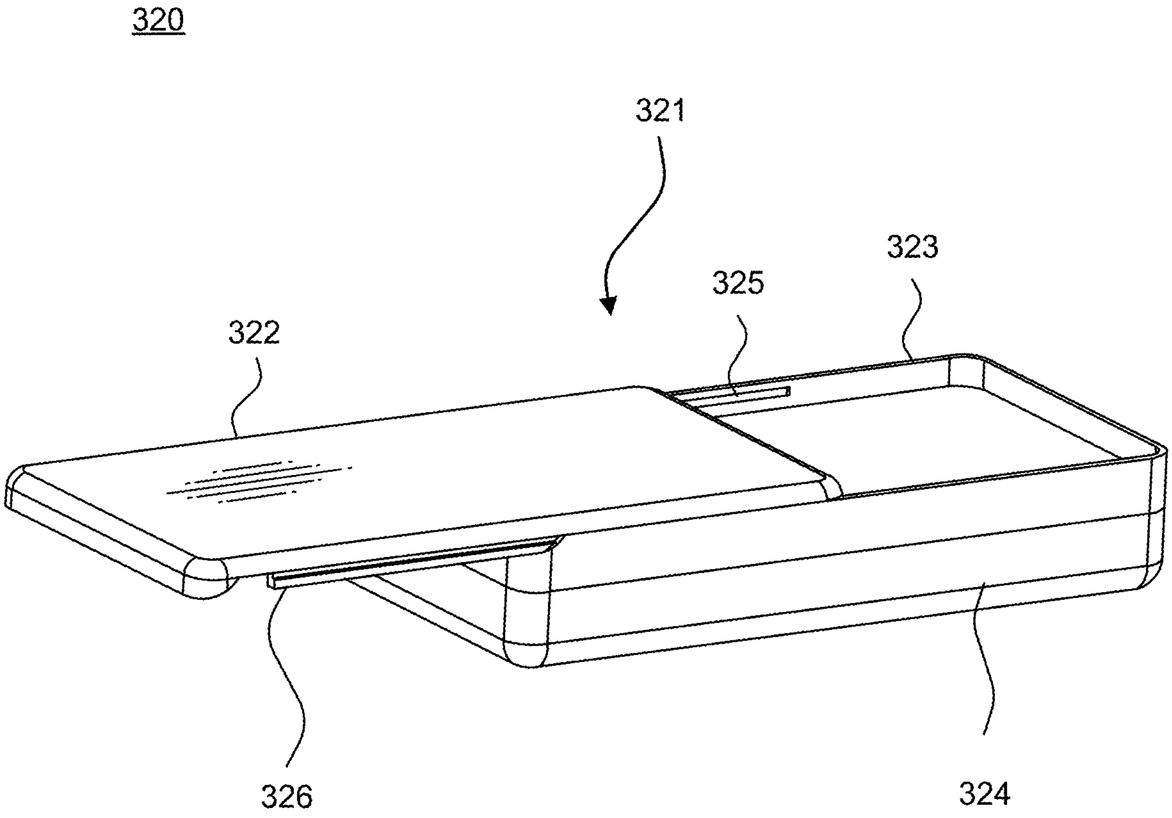
FIG. 22 is a perspective view diagram showing a case for the disposable single use pocketable AED with an alternative opening mechanism.

The cover can also be attached using rails or slides. FIG. 22 is a perspective view 320 diagram showing a case 321 for the disposable single use pocketable AED with an alternative opening mechanism. The case 321 includes a cover 322, an electrode enclosure 323, and a circuit enclosure 324. The cover can control access to an interior of the case, specifically, a cavity of the electrode enclosure, by sliding open and closed.

A pair of slides 326 can be affixed on a bottom surface of the cover, which faces the cavity of the electrode enclosure. Each slide 326 can be affixed on opposite sides of the cover along a length of the case. Tracks 325 are affixed to an interior of the electrode enclosure along opposite walls. The slides 326 of the cover 322 can move back and forth along the tracks 325 to move the cover 322 to open and closed positions. Movement of the cover can occur manually with a user sliding the cover along the tracks. A locking mechanism (not shown) can be included, such as a fastener or hook to prevent unintentional movement of the cover. Additionally, the two-step manual maneuver and process to prevent unintentional opening can also be utilized.

Figure 23:
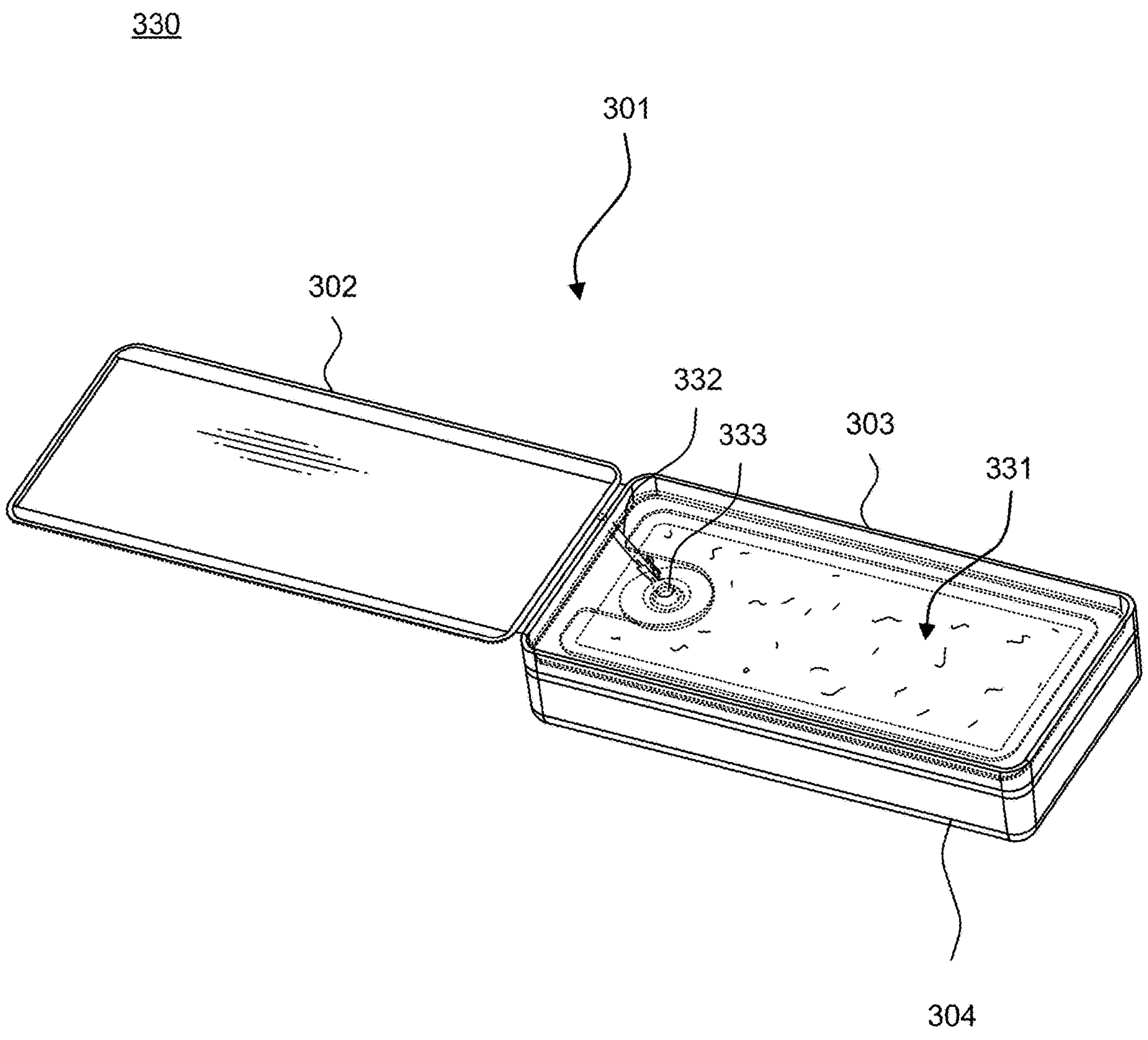
FIG. 23 is a perspective view diagram showing the case of FIG. 20 in an open position with electrode pads.

The cavity or interior of the electrode enclosure can be shaped and sized to house the electrode pads, which can lay flat or folded in some manner in the electrode enclosure. FIG. 23 is a perspective view 330 diagram showing the case 301 of FIG. 20 in an open position with electrode pads 331. A pair of the electrode pads 331 can lay directly on a bottom surface of the electrode enclosure with one electrode pad stacked on top of another electrode pad. In a further embodiment, the electrode pads can lay on a boss provided in the electrode enclosure, as described in detail below with reference to FIG. 25.

In the embodiment that the pads are placed directly inside the cavity of the electrode enclosure 303, then the Moisture Vapor Transmission Rate (MVTR) of the electrode enclosure can be improved by use of coatings, lamination, or vapor deposition of MVTR-reducing materials. A decreased MVTR is beneficial as it increases the time the electrodes remain at the ideal hydration range. An increased duration of storage at the ideal hydration range can equate to longer shelf life.

In another embodiment the pads are placed inside a hygienic pouch or container that is placed inside the cavity of the electrode enclosure 303 to prevent contamination or damage to the pads. The pouch can be poly foil or other type of hygienic material. To reduce size of the overall AED, the wires inside the pouch may be managed with various cable management techniques, such as disposable wraps. An electrode pouch often has excess size beyond the size of the electrode it contains. This excess area often includes air gaps around the electrode to prevent heat sealing from damaging the electrodes, as well as includes the heat seal locations. To additionally reduce the size of the AED, the excess areas of the pouch can be folded to increase the compactness of the pad assembly that is placed inside the cavity. When needed, the electrode pads can be removed from the pouch by unsealing, tearing open, or unfolding the pouch.

The electrode pads 331 can each include a wire 332 affixed via a connector 333 on the pad. The wires 332 can extend from the electrode pads 331 and connect to the energy storage circuit (not shown) housed in the circuit enclosure 304. When placed in a pouch, the wires can extend from the pads outside the patch and to the circuit.

The wires can connect the electrode pads and circuit via a metal or plastic feedthrough mechanism, such as a tube, through the electrode enclosure. In a further embodiment, the feedthrough mechanism can be formed in a bottom surface of the electrode enclosure as a hole in the shape of a circle, rectangle, square, or other shape to allow the wires in the electrode enclosure to access the circuit in the circuit enclosure. In one embodiment, the wires can be hardwired to the circuit to prevent displacement of the wires from the circuit. A strain relief can also be used with the feedthrough to prevent pulling of the wires from the circuit. For example, the wires can be glued in or to the feedthrough.

The wires can be longer than a length of the case and must be wrapped or folded to fit to reach the victim's chest from the AEDs position to the side of their chest. In one example, the wires are at least 3 ft. long and can be wrapped around an interior of the electrode enclosure, in the cavity. In a further example, the wires can lay on top of the top electrode pad, and in yet a further example, the wires can be wrapped around a boss as further described in detail below with respect to FIG. 25.

Each electrode pad can include an adhesive on at least a portion of one side to affix to a chest of a patient. The adhesive is protected by a liner (not shown) that can be removed prior to placement of the pad on the patient.

Figure 24:
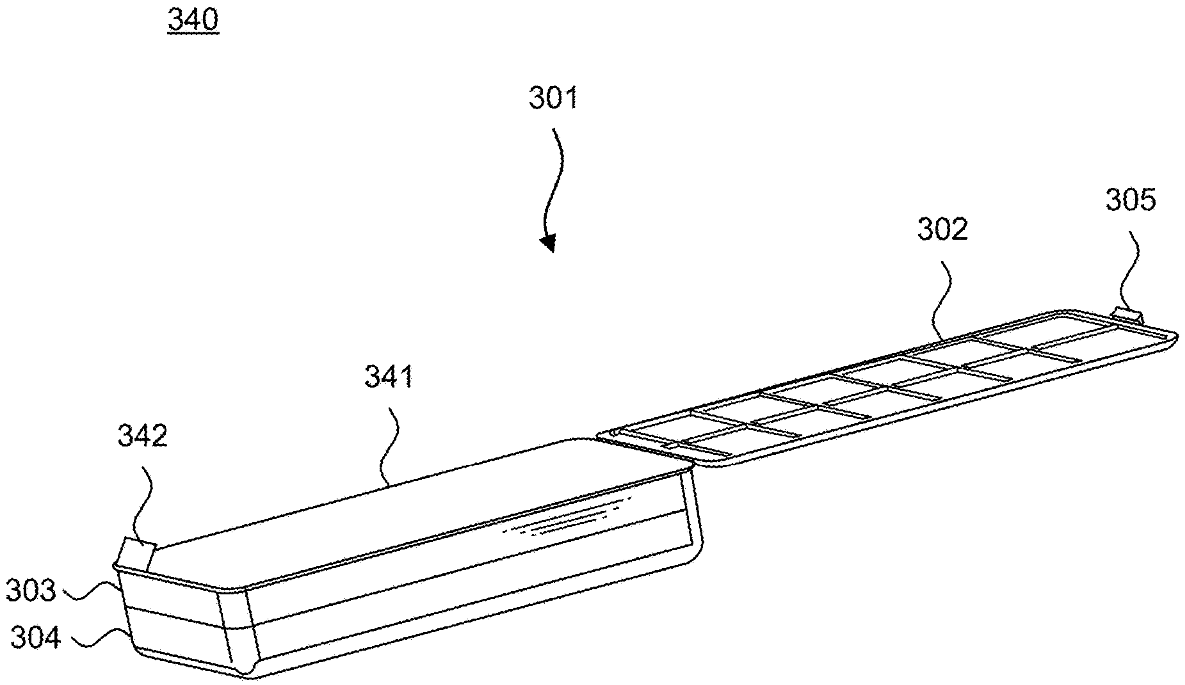
FIG. 24 is a perspective view diagram showing the case of FIG. 20 in an open position with a seal.

When a pouch is not used, a seal can be used to protect the electrode pads and ensure the pads are hygienic and operable when needed. FIG. 24 is a perspective view 340 diagram showing the case 301 of FIG. 20 in an open position with a seal. The cover 302 of the case is in an open position, which can provide access to an interior of the case, including the electrode enclosure 303. A seal 341 is secured over the cavity of the electrode enclosure 303 and electrode pads (not shown). The seal can be made of a layer of nylon, foil, or polypropylene. However, other types of material for the seal are possible. At a minimum, the material should have a moisture vapor transmission rate equal or less than 0.0005 $g/in^2/24$ hrs. The seal 341 can be sized to fit over the electrode enclosure cavity and attach to a top surface of the walls of the electrode enclosure 303. The seal 341 can include a tab 342 on one side, or multiple sides, so that a user can pull the tab to remove the seal. When the electrode pads are placed in a pouch, the seal is not necessary, but can be used.

Figure 25:
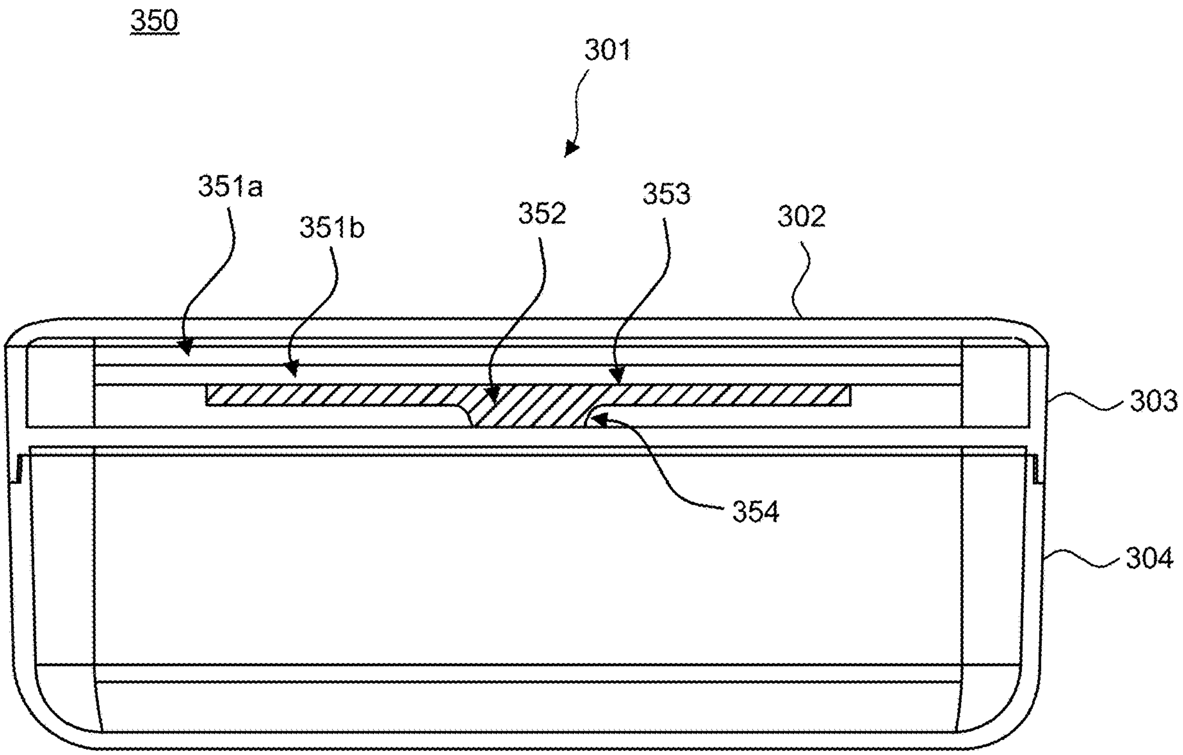
FIG. 25 is a side view cross section showing the case of FIG. 20 with a boss in the electrode enclosure.

A magnet or mechanical trigger can be affixed to the electrode pads, pouch in which the electrode pads are stored, or the seal to initiate charging of the electrical pads. For example, when the seal is removed from the electrode enclosure, the energy storage circuit can begin charging. In a further example, charging can be initiated when the pouch is opened, or the electrode pads are removed from the electrode enclosure. Whether the electrode pads are directly placed in the electrode enclosure or placed in a pouch, the electrode pads can lay on a bottom surface of the electrode enclosure or on a boss above the bottom surface of the electrode enclosure. FIG. 25 is a side view cross section 350 showing the case 301 of FIG. 20 with a boss 352 in the electrode enclosure. A boss 352 can be placed in the cavity of the electrode enclosure 303 of the case 301 to hold the electrode pads 351*a, b* and organize the wires (not shown), while simultaneously providing space for the circuit underneath. The pads can rest on top of the boss, above where the wires are wrapped, thus making more compact the form factor of the electrode enclosure. It will likewise provide more space for the energy storage circuit.

The boss 352 can be made of a single piece of material and comprise a three-dimensional shape, such as an oval or rectangle, as well as other shapes. Alternatively, the boss 352 can include a stand 354 affixed to a bottom surface of the electrode enclosure 303 and can be shaped as a circle, rectangle, square, or other shapes. A flat surface 353 that is the same size as or smaller than the electrode pads is affixed to the stand 354. The flat surface holds the electrode pads 351*a, b* above the bottom surface of the electrode enclosure 303, while the wires attached to the electrode pads wrap around the stand. Other configurations for storing the wires are possible. The electrode pads 351*a, b* can be stored on top of one another. When the pads are non-flat, the flat surface of the bottom surface of the electrode enclosure or the boss helps the non-flat pads to lay flat.

Figure 26:
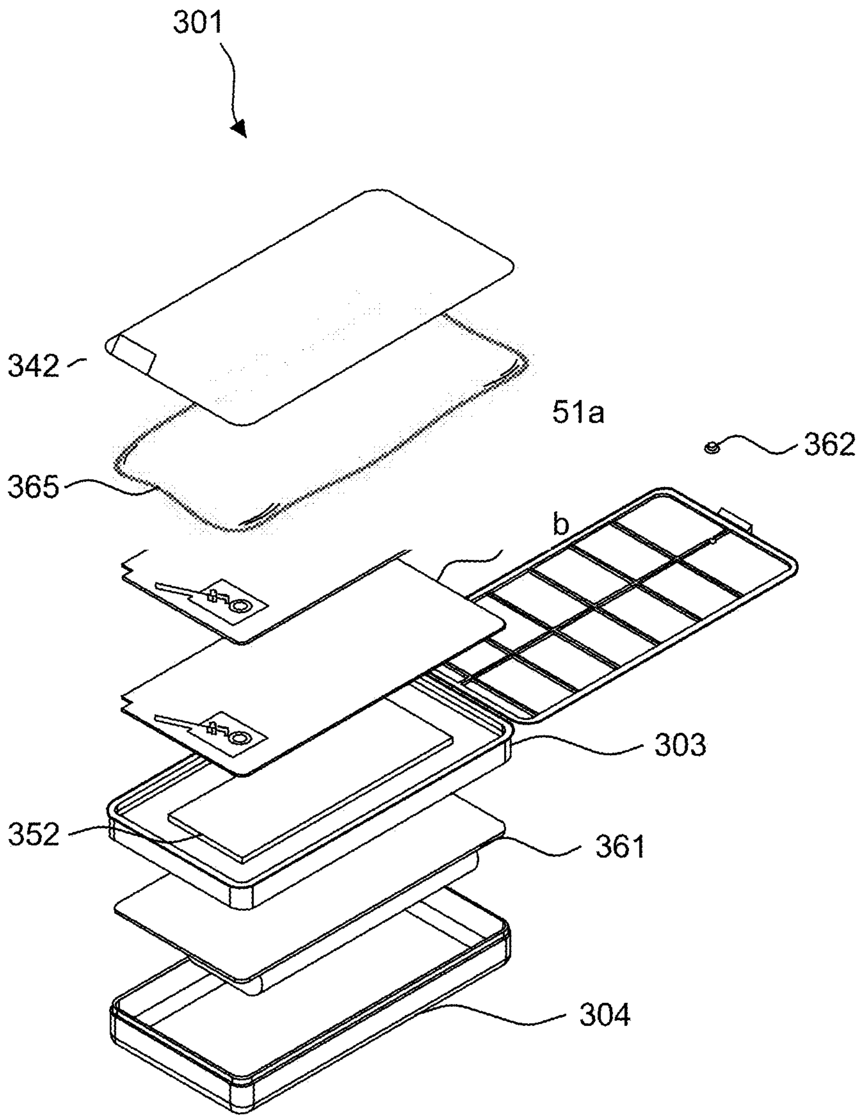
FIG. 26 is an exploded view showing the case of FIG. 20.

The AED case is specialized and specifically configured for secure storage of the AED circuit, as well as quick deployment of the AED, such as affixing the pads to the patient and initiating energy to the pads for delivery to the patient. FIG. 26 is an exploded view 360 showing the case 301 of FIG. 20. The bottom of the case includes the circuit enclosure 304 in which the energy storage circuit 361 for the AED is housed. The electrode enclosure 303 with boss 352 is located over or above the circuit enclosure 304. The electrode pads 351*a, b* are placed on a top surface of the boss 352 and a seal 341 with a tab 342 covers the electrode pads 351*a, b*. The boss provides more space for the energy storage circuit; however, the electrode pads 351 *a, b* can also be placed directly in the electrode enclosure 303 without the boss 352. In one embodiment, the electrode pads 351 *a, b* can be placed in a pouch 365 prior to placement on the boss 352 or directly in the electrode enclosure 303. If necessary to fit within the case, the pouch 365 can be folded. A magnet or mechanical trigger 362 is placed on one or more of the cover 302, electrode pads 351*a, b*, pouch 365 in which the electrode pads 351*a, b* are stored, or electrode enclosure 303 to initiate charging of the AED upon trigger of the magnet or manual trigger.

Figure 27:
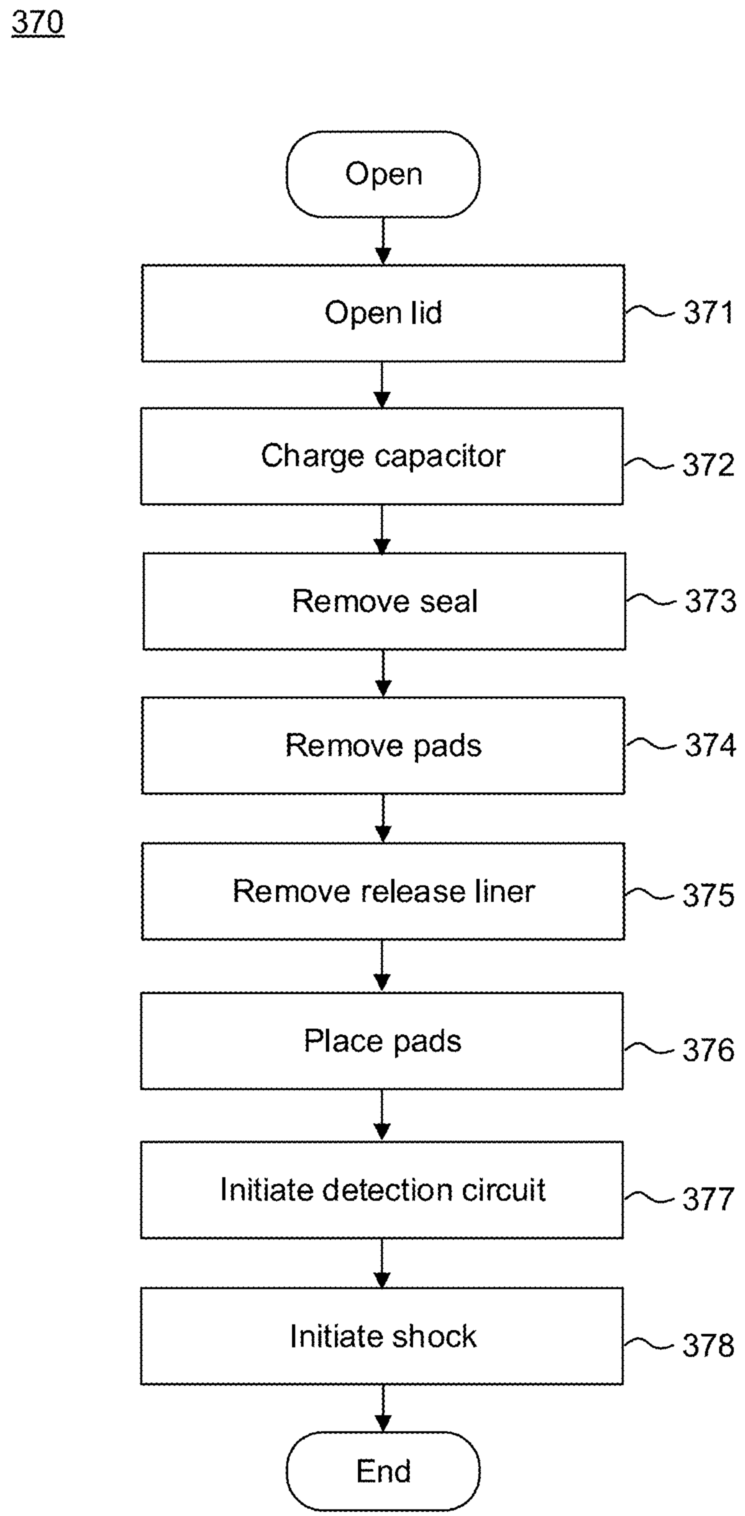
FIG. 27 is a flow diagram showing a process for using the AED housed in the case.

In addition to ensuring the case is easily accessible and always available, the case must also be easy to open and facilitate easy use of the AED. FIG. 27 is a flow diagram showing a process 370 for using the AED housed in the case. When a person is in need of defibrillation, the case can be pulled out of a pocket, purse, or carrying case of a user or from another location. The cover of the case is opened (step 371), such as by sliding the cover to an open position or releasing a fastener on the cover. Once opened, charging (step 372) of the capacitor can begin. A user can remove (step 373) the seal over the electrode enclosure or tear open a pouch contained inside of electrode enclosure 303 to access the electrode pads. The electrode pads are removed (step 374) from the case or pouch, and the user removes (step 375) the liners from the pads to stick (step 376) the pads to a patient's chest. Based upon a trigger or manual action, an activity detection circuit (step 377) is initiated to detect whether a shockable event of the patient, such as ventricular fibrillation, is detected. The trigger can include application of the pads to the patient's chest or removal of the pads from the case, while a manual action can include a button press to initiate charging and detection analysis for a shockable event. The charging and activity detection can occur simultaneously or sequentially. When performed sequentially, charging of the capacitor can begin upon pad application to the patient and before the detection algorithm is satisfied.

If a shockable event is detected, one or more shocks are provided (step 378) to the patient. In one embodiment, up to six shocks can be administered to the patient. When multiple shocks are necessary, activity detection can be applied after each shock to determine whether an additional shock is needed.

Figure 28:
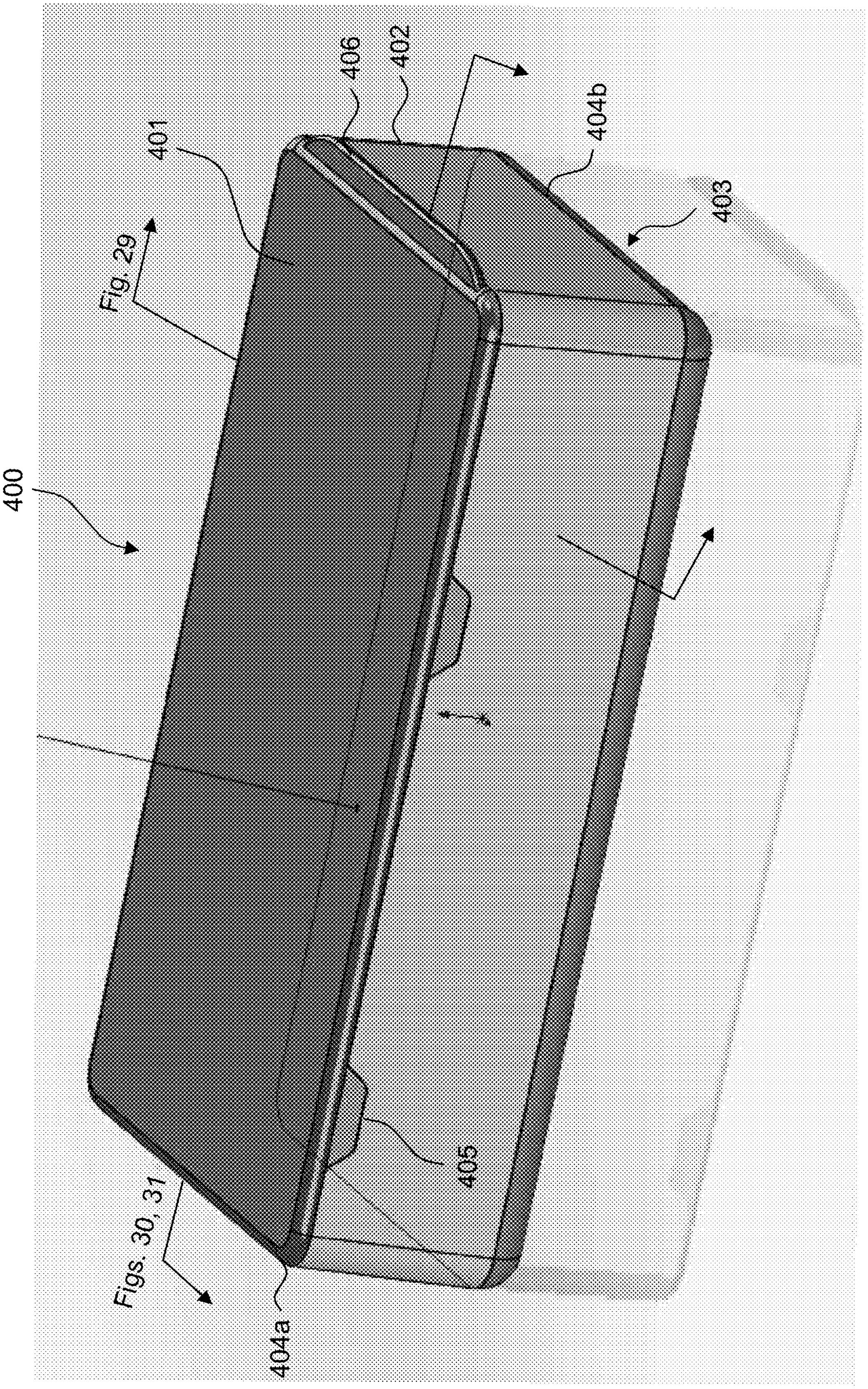
FIG. 28 is a block diagram showing, by way of example, housing 400 of a disposable, single use, pocketable AED with a secure wire assembly.

To confidently and accurately administer the shocks when necessary, care must be taken to ensure the pads are not disconnected from the circuit. Additionally, it is best practice to protect the wires that connect the pads to the circuit, from sharp bends or other damage, otherwise, the pads may not be able to deliver a shock to the user when needed. The wires and connections between the circuit and pads must also be protected from ingress of water and debris, and to maintain a stable environment. FIG. 28 is a block diagram showing, by way of example, housing 400 of a disposable, single use, pocketable AED with a secure wire assembly. The housing 400 includes four walls 402, a bottom surface 403, and a cover 401. The terms "housing" and "case" can be used to refer to a receptacle for holding components, all of which, together, form an AED for administering an electrical shock to a patient. The user can be the patient himself or a third party as the AED is fully automatic once pads are applied.

At least a portion of the cover 401 and bottom surface 403 are covered with a material 404*a-b* that can absorb physical shock due to unintended movement, such as moving around in a bag or being dropped. The physical shock-absorbing material can include a polymer that is integrated or molded onto a surface of the cover and bottom surface. The physical shock is distinct from the AEDs delivery of an electrical shock, which is therapeutic and applied to a patient. The physical shock-absorbing material allows impact on the housing to be absorbed, such as when the housing is shuffled around in a backpack or pocket of a user, or the housing is dropped. In one embodiment, the physical shock-absorbing material 404*a-b* can be placed around the outer edges of the cover and the bottom surface. However, other configurations of the shock-absorbing material are possible, such as covering all external surfaces or a portion of the outward facing surfaces of the cover and bottom surface.

Figure 31:
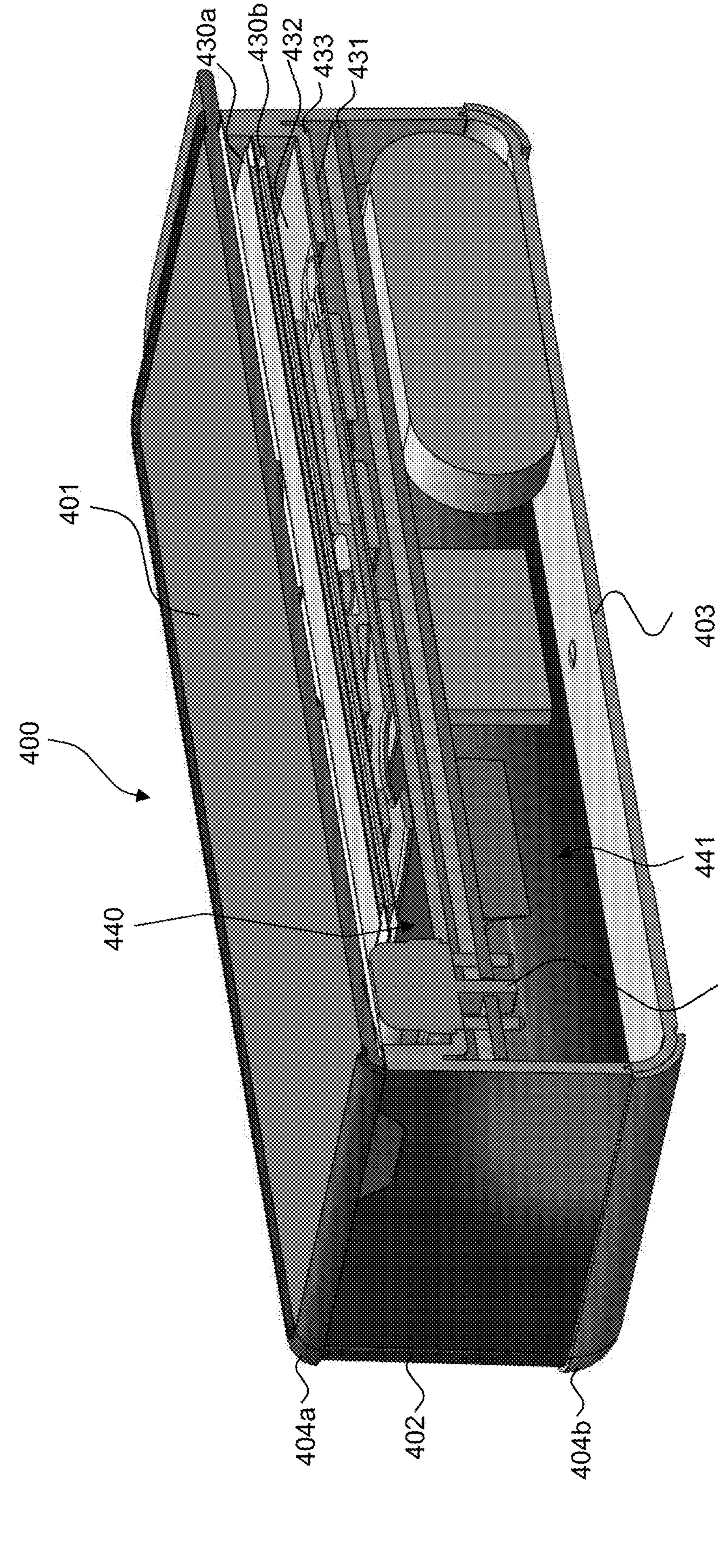
FIG. 31 is a block diagram showing, by way of example, a longitudinal cross section of the housing of FIG. 28 with interior components.

A dividing layer (not shown), described in detail below with respect to FIG. 31, can divide the space formed in the interior of the housing to create two compartments, such as the electrode enclosure and circuit enclosure shown in FIG. 20. Specifically, the dividing layer can prevent access to the circuit enclosure, which sits below the electrode enclosure, while the electrode enclosure remains accessible by the user once the cover is removed.

The cover 401 can include an overhang 406 that extends from one end. A user can press upward on the overhang 406 to initiate opening of the cover. The cover 401 can also include one or more tabs 405 formed along one or more sides of the cover 401. Each tab 405 can each be perpendicularly positioned along an outer edge of the cover 401 to extend over one of the walls 402 of the housing 400. The tabs 405 help prevent the cover from unintentionally opening and exposing the pads (not shown) stored in the housing 400. In one embodiment, the tabs 405 can be placed in a zipper fashion along the longitudinal sides of the housing, as further described in detail below with respect to FIG. 32. However, other configurations of the tabs are possible, such as placed directly across from each other with the same number of tabs on the same side or with different numbers of tabs on each of the longitudinal sides.

Figure 29:
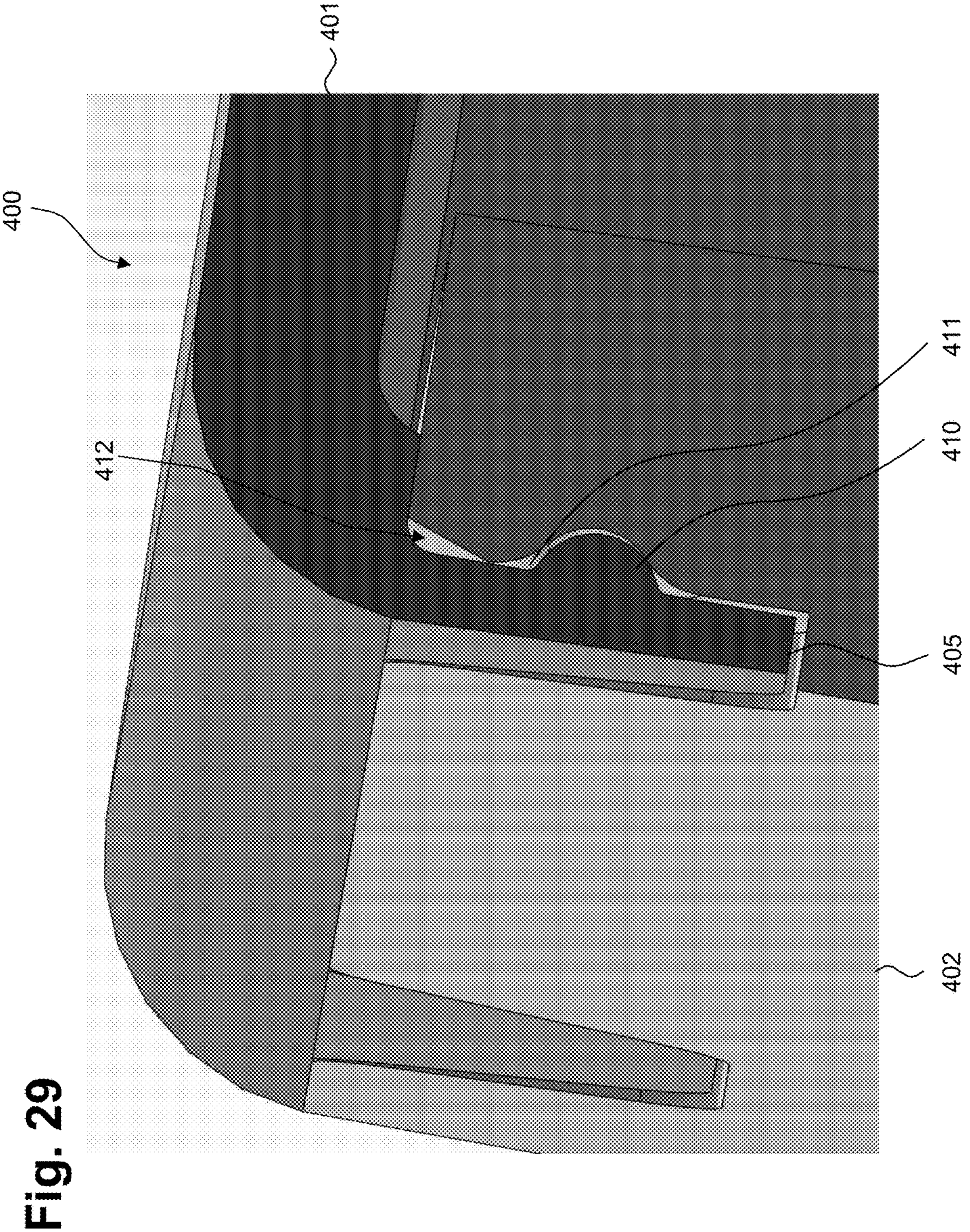
FIG. 29 is a block diagram showing, by way of example, a latitudinal cross section of the housing of FIG. 28.

The cover can protect the peelable tray lid from damage or unintentional opening. To ensure the cover is securely closed and yet still able to be opened with reasonable force expected of users, grooves (not shown) can be formed along a top end of one or more of the housing walls. The grooves are shaped to removably receive the tabs. FIG. 29 is a block diagram showing, by way of example, a latitudinal cross section of the housing of FIG. 28. A groove 411 is formed in an outer surface of one or more walls 402 of the housing 400. Specifically, the groove 411 forms a void, in the wall 402 of the housing 400, in which a protrusion 410 of the tab 405 on the cover 401 of the housing 400 fits. When force is applied to the cover 401, such as in an upward motion, the protrusion 410 of the tab 405, slides out of the groove 411. In one embodiment, a bump 412 is formed on a top side of the groove, such that the top edge of the wall 401 appears to slope downward towards the bump 412. The bump helps prevent accidental release of the protrusion 410 out of the groove 411. Simultaneously, the bump serves as a ramp to facilitate manufacturing assembly of the lid to the housing by reducing the forces required to mate the lid to the housing. However, when the opening force of the cover is applied, the protrusion 410 slides out of the groove 411 and over the bump 412.

Figure 30:
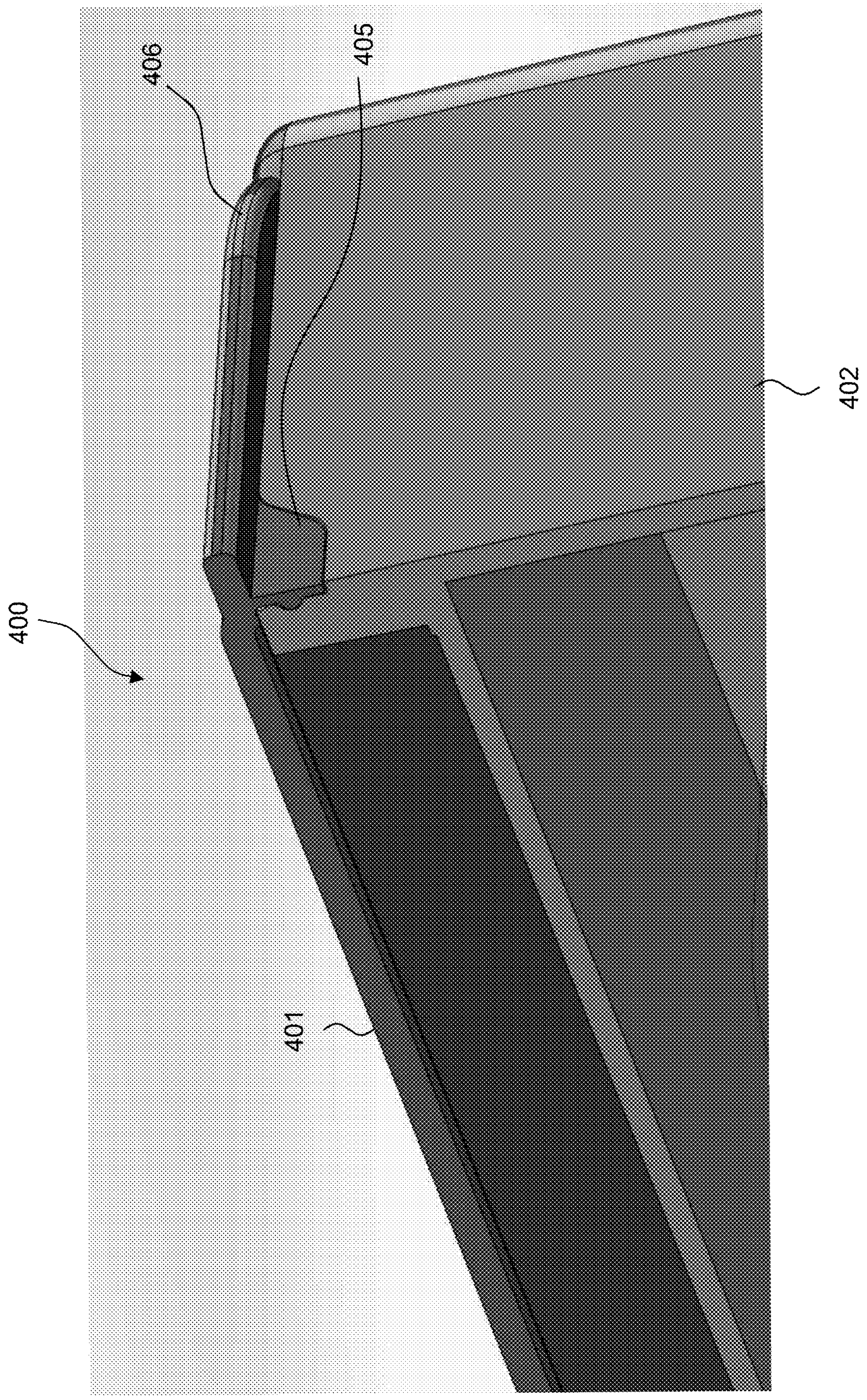
FIG. 30 is a block diagram showing, by way of example, a longitudinal cross section of the housing of FIG. 28 with an overhang.

Opening of the cover can be initiated via an overhang. FIG. 30 is a block diagram showing, by way of example, a longitudinal cross section of the housing of FIG. 28 with an overhang. The overhang 406 can be formed on a latitudinal side of the cover, between the two longitudinal sides, and extends beyond the wall 402 below, which is perpendicular to the overhang 406. The overhang 406 can have texture to enhance grip. The overhang 406 can be an extension of the cover or can be a separate piece that is attached to an edge of the cover to extend over the wall. A user can open the housing 400 of the AED, to access the pads (not shown), by pushing the overhang 406 in an upward motion or by pushing the overhang towards the opposite end of the housing 400, depending on whether the cover lifts off or slides open.

A tab 405 can be located below the overhang 406 and a corresponding groove can be formed in the wall below to receive the tab. As described above with reference to FIG. 29, once the user applies pressure to the overhang 406, the protrusion (not shown) of the tab can move out of the groove in the wall, which allows the cover to move away from the walls, providing access to the peelable tray lid, which can then be removed, providing access to the interior of the electrode enclosure. As the overhang is continuously pushed upward and away from the housing, other tabs pop out of the grooves until all the tabs are removed from the grooves and the cover is removed from the housing. In one embodiment, the last tab to be removed from the groove is located on a side of the cover opposite the overhang.

Once opened, the peelable tray lid and the components therein can be accessed, while the circuit board in the circuit enclosure is inaccessible without breaking the housing. FIG. 31 is a block diagram showing, by way of example, a longitudinal cross section of the housing of FIG. 28 with interior components. The housing 400 includes various interior components, which together form the AED. As described above, the AED can be pocket sized for carrying convenience and programmed to determine when shock is necessary for applying to a patient. The housing 400 includes a top cover 401, four side walls 402 and a bottom surface 403. Edges of the cover 401 and bottom surface 403 can be covered with physical-shock absorbing material 404*a-b* to prevent damage to the interior components when the housing 400 is dropped or jostled. In another embodiment, the cover can be connected to the peelable tray lid. Upon opening the cover, the peclable tray lid is automatically removed by the action of removing the cover.

A dividing, middle layer 433 separates an interior of the housing into two compartments, the electrode enclosure 440 and the circuit enclosure 441. The dividing layer 433 can be made from the same or different material than the walls. Also, the dividing layer can be a separate piece of material that is affixed to each of the four side walls or can be formed from the same piece of material as the side walls. In one embodiment, the middle layer 433 can be positioned at a 90 degree angle to each of the walls. In another embodiment, a portion of at least two of the side walls 402 can be thicker on a top end, such as in the electrode enclosure 440. The thicker wall of the electrode enclosure then splits by a portion of the thicker wall extending downward into the circuit enclosure and another portion curving in towards an interior of the walls to form the middle layer 433.

In a further embodiment, the circuit board 431 enclosure can act as a bottom surface for the electrode enclosure. In such embodiment, the middle layer 433 becomes part of the electrode enclosure. The middle layer 433 can be made of plastic, film, metal, laminate, epoxy, potting material, or foam, as well as other types of material.

The electrode enclosure 440 holds electrode pads 430*a-b*, a spool 432, and wires (not shown) for the electrode pads, which are wrapped around the spool 432. The circuit enclosure 441 holds a circuit board 431 to power the shock when needed. The electrode pads 430*a-b* can each include one or more of an electrode, hydrogel, release liner and backing, and can rest upon the spool for easy access by a user. The wires are each connected on one end to one of the electrode pads and on another end to a plug 434, which connects to the circuit board 431 in the circuit enclosure 441.

Figure 32:
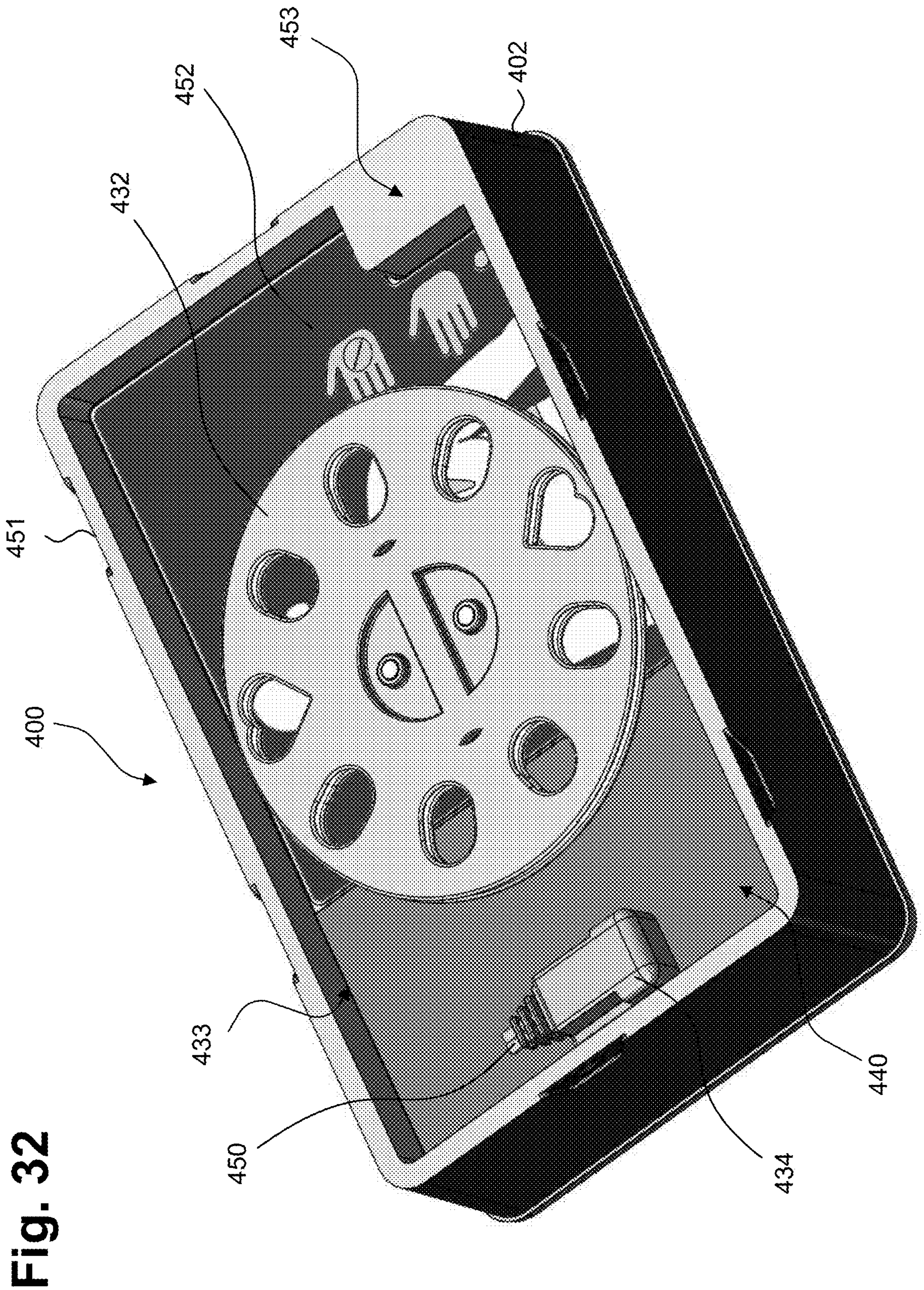
FIG. 32 is a block diagram showing, by way of example, a top perspective view of an interior of the housing of FIG. 28.

The spool 432 helps keep the wires organized to prevent tangling or kinking, which can cause damage to the wires. FIG. 32 is a block diagram showing, by way of example, a top perspective view of an interior of the housing of FIG. 28. An upper edge of the housing walls include cutouts 451, which include the grooves of FIG. 29. Single cutouts 451 can be included on the latitudinal walls, one of which is below the overhang of FIGS. 28 and 30. The cutouts 451 are configured to receive the tabs of FIG. 29, which are affixed to the cover of the housing.

In this example, the cutouts on the longitudinal sides of the housing are placed in a zipper configuration with the cutouts placed in a zig zag manner. For example, one cutout is placed on a left side wall near the overhang, then the next cutout is placed on the right side wall, further away from the overhang. The next cutout is placed on the left side way, further from the overhang than the cutout on the right side wall, and so on. As the overhang is pushed upward, the tab under the overhang is removed first from the cutout. Subsequently, the next tab nearest the overhang is removed, such as on the left side wall, and then the next tab nearest the overhang is removed, such as on the right side wall. The tabs will continue to pop out of the grooves in a left to right manner, like a zipper, until all the tabs have been removed from the grooves and access to the peelable tray lid and the electrode enclosure is possible.

The interior of the electrode enclosure 440 can include a chamber 453 with a switch (not shown), relay (not shown), and buzzer (not shown). The switch is activated or deactivated in the presence of magnetic field such as that generated by a permanent magnet, placed in the cover of the housing. In one embodiment it is used to trigger a relay which connects the battery through dry contacts to provide power to the circuit board upon one or more conditions, such as opening of the case. The buzzer can make a noise based on the trigger to provide notice of the power-on. In one example, when the cover is closed and the magnet is close to the switch, no power is provided to the circuitry. However, once the cover opens and the magnet is moved further than a predetermined distance from the switch, the switch changes position to initiate a start-up, including power flow from the battery to the circuitry to provide defibrillation waveforms to the pads, if necessary. The switch and magnet are described in further detail in commonly-owned U.S. patent application Ser. No. 18/401,199, titled “De-energizable Defibrillation Assembly,” filed on Dec. 29, 2023, which is hereby incorporated by references in its entirety.

A spool 432 can freely rest on a top surface of the middle or dividing layer 433. In a further embodiment, the spool can be secured to the walls of the housing or the dividing layer. The top surface of the dividing layer can include a user interface 453, which provides a status of the AED and is further described below with reference to FIG. 34. The spool can rest upon the user interface, if one is present. Wires 450, connected to the electrode pads, can be wrapped around the spool and terminate at a plug 434. The plug 434 is connected to the circuit board (not shown), which is located below the dividing layer 433, to receive power for the pads via the wires.

Figure 33:
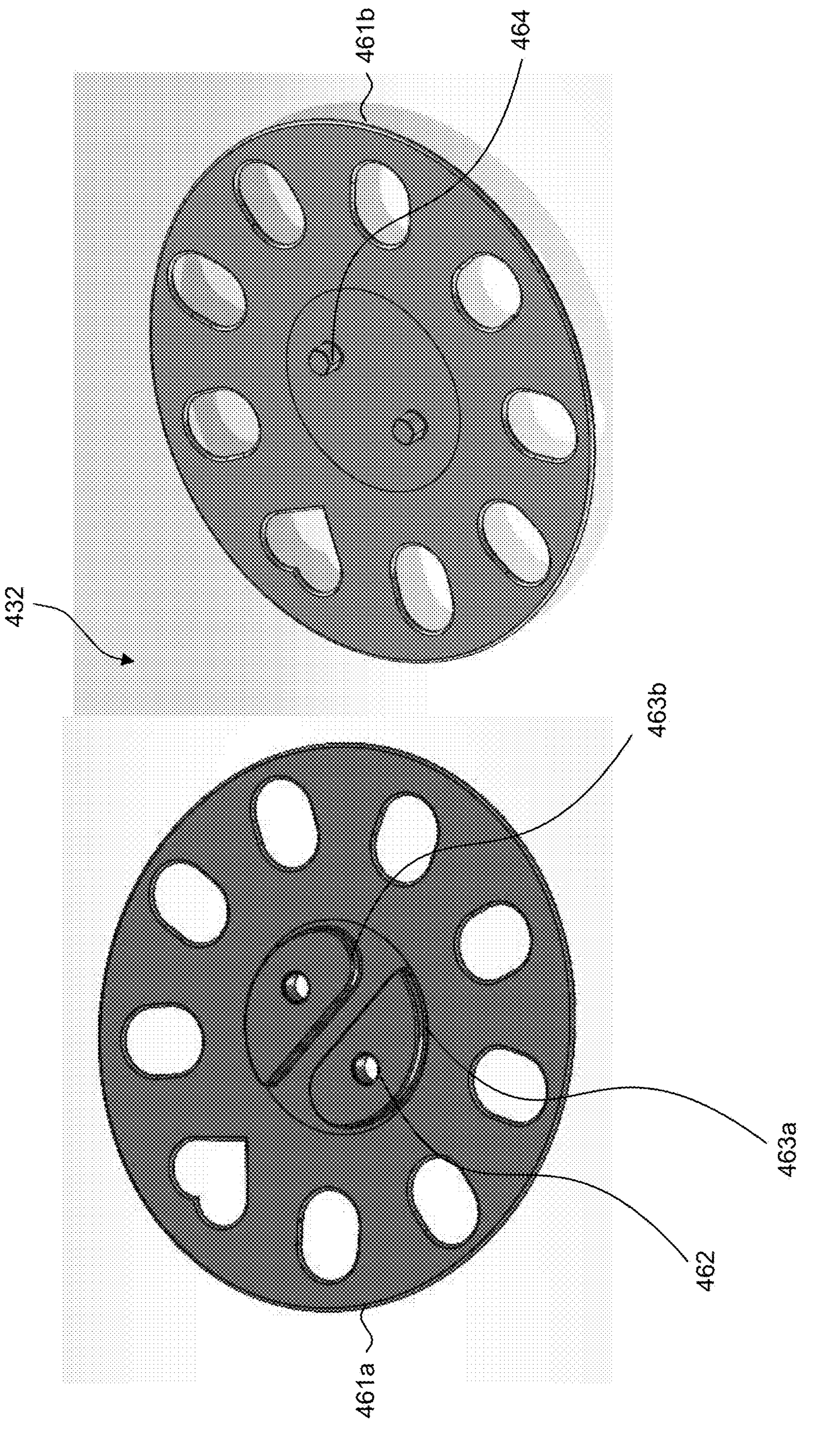
FIG. 33 is a block diagram showing, by way of example, a deconstructed view of a spool.

The wires can be wrapped around a barrel of the spool or secured in the barrel of the spool and then wound around. FIG. 33 is a block diagram showing, by way of example, a deconstructed view of a spool. The spool 432 can include a barrel 463*a-b* and a flange 461*a-b* on each end of the barrel 463*a-b*. One flange 461*a* includes the barrel, which is made of two pieces located across from one another. In one example, the barrel can include two half circles 463*a-b* that are positioned with the flat side facing one another at a predetermined distance to create a channel for the wires. The barrel can also include two complimentary shapes, such as yinyang or curved tear drop shapes. Other shapes are possible. Such shapes can function as a strain relief for the wires to prevent unintended forces, such as pulling or twisting of the wires, which can cause damage. A portion of each wire from the two pads can be placed in the space to secure the wires to the spool 432 and then wound around the rounded ends of the barrel 463*a-b*. The spools can include pockets and holes that facilitate automation of the winding of the spool. These pockets and holes can receive fixturing attached to robots, cobots, servos, or other electromechanical equipment, to automate winding of the leadwires around the spool, thereby removing the need for costly human operator involvement. Alternatively, the wires are merely wrapped around the rounded edges of the barrel 463*a-b*, rather than placed through the channel formed by the two flat sides of the barrel 463*a-b*.

Each half circle barrel 463*a-b* includes a hole 462 through which a prong 464 located on the other flange 461*b* is inserted. The flange 461*a* with the barrel 463*a-b* can also include one or more guides (not shown), which help guide the wire as it unwinds from the barrel. Voids (now shown) can also be formed on the other flange 461*b* to fit over the guides to secure the flanges 461*a-b* together.

Once the cover (not shown) is opened and the peclable tray lid is removed, a user can remove the electrode pads (not shown), which rest upon the spool 432. As the electrode pads are removed, the spool spins to release the wire, allowing the pads to be moved away from the housing for placement on a patient. As the wires unwind, the spool 432 may be removed from the electrode enclosure. For instance, when the pads are moved out of the housing, the wires unwind and the spool remains attached to the wire. In contrast, if the wires are merely wound around the barrel, the spool will be released from the wires once the wires are fully extended.

Figure 34:
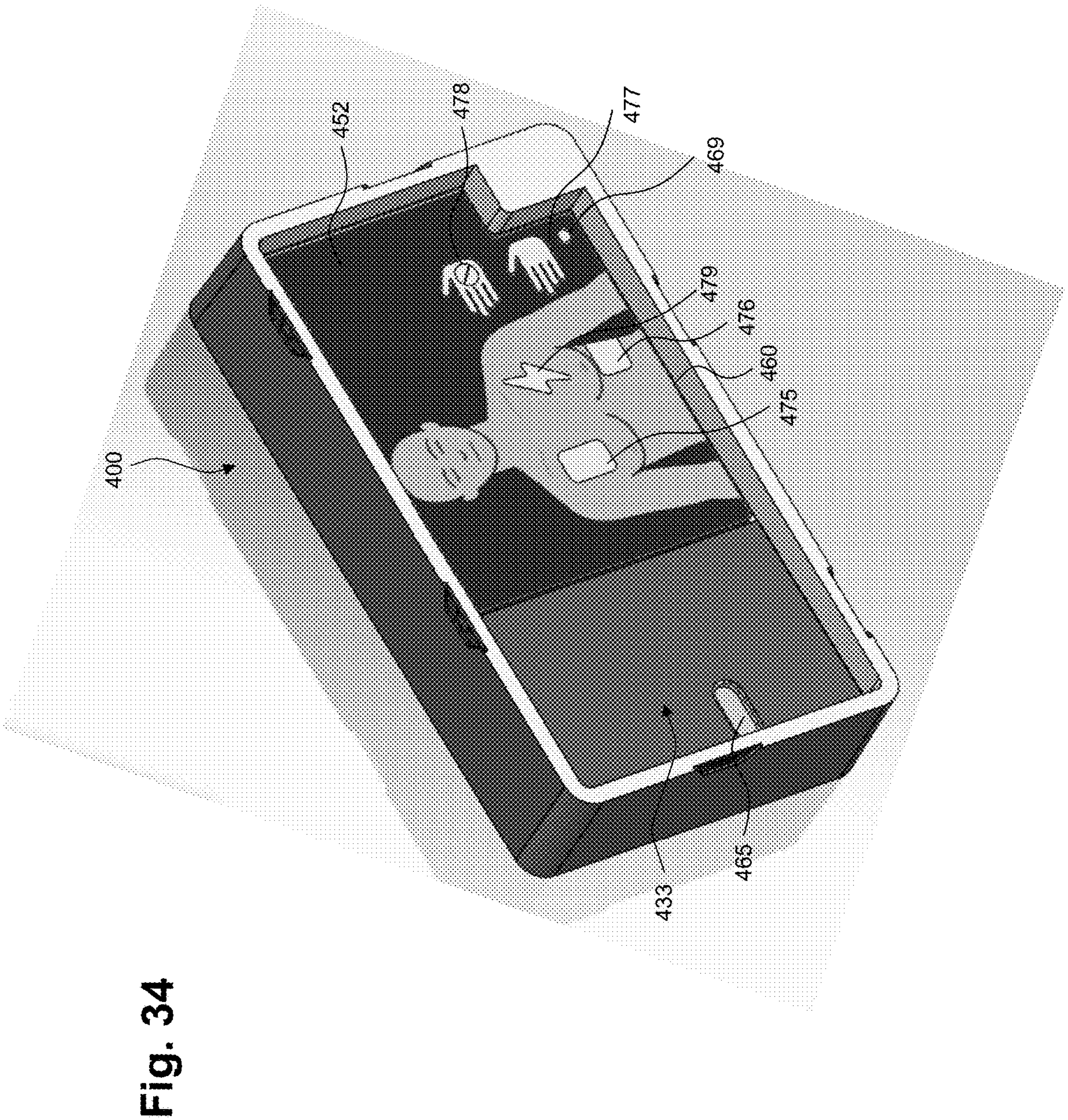
FIG. 34 is a block diagram showing, by way of example, an open housing with a user interface.

Once the spool is removed from the housing, the user can view a user interface, which is provided on the dividing layer. The user interface provides a status of the AED and displays instructions for use to the user. FIG. 34 is a block diagram showing, by way of example, an open housing with a user interface. The user interface 452 can be located on at least a portion of the top surface of the dividing layer 433, and can include progress and status of the AED. For instance, in one example, the user interface can include a display, such as a card, of a human body 460 with cutouts or windows for status indicators 475-479. The windows can be clear, colored, or diffuse. In one example, the interface can be a sheet, or an adhesive-backed sheet, printed with the body 460 with cutouts or windows for the status indicators.

A light emitting device can be located in the dividing layer 433, in the cutout or window, of each status indicator 475-479, to identify whether that status has been met. The lights are powered via the circuit board, which is located below the dividing layer 433. The lights can be located on the circuit board. The status indicators 475-479 can include representations of the pads 475, 476 placed on the body 460, as well as a hand 477 that indicates the patient is safe to touch and another hand 478 that indicates the patient is not safe to touch, such as when shock is about to be provided to the patient. A thunderbolt 479 indicator can indicate whether the AED is in a state of preparing for or providing shock to the patient. A status 469 indicator can indicate whether the AED is functioning properly or in a state of error. In another embodiment, a light based communication system, such as that utilizing infrared wavelengths, is located in the dividing layer to facilitate programming, manufacturing, diagnostics, waveform downloading, and live viewing of data. One or more of the status indicators can be displayed on a sticker or in mold label, which also includes a corresponding window through which the light connected to the circuit board can shine to indicate a status associated with that indicator. The window can be clear, diffuse, or different colors.

The lights below each status indicator can be turned on or off to indicate a different status. For instance, when the pads 475, 476 are correctly placed on the patient, the lights can turn on to indicate the pads are in position. However, when the lights are off or are blinking, the pads are determined to be not on the patient. The lights for the hands 477, 478 can turn on to indicate whether a user can touch the patient or not. Also, when the light associated with the thunderbolt indicator is on, the user is informed that shock is being applied or about to be applied to the pads on the patient.

Figure 35:
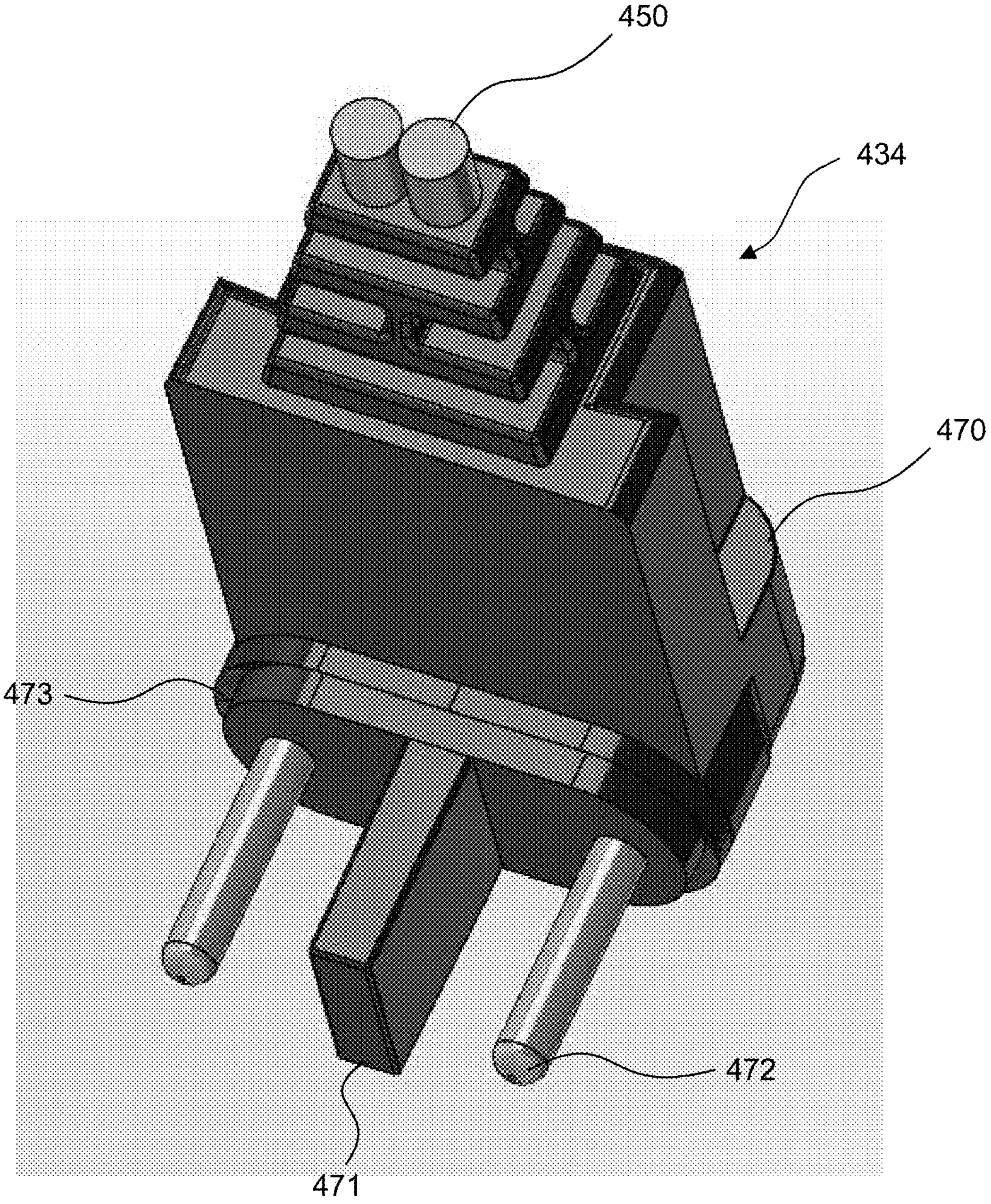
FIG. 35 is a block diagram showing, by way of example, a perspective view of a plug.

In addition to the user interface, the dividing layer 433 also supports a plug (not shown) that connects the wires of the pads to the circuit board. A cutout 465 is formed in the dividing layer 433 to prevent the plug from moving around on a surface of the dividing layer 433. The cutout 465 is shaped to correspond with a base on the plug. FIG. 35 is a block diagram showing, by way of example, a perspective view of a plug. The plug 434 is connected to the pad wires and a portion of the plug rests on the dividing layer, while another portion of the plug extends through the dividing layer to connect to the circuit board.

The plug 434 includes a body 470 that rests upon the dividing layer (not shown). The pad wires 450 are connected to one end of the body 470, while an ultrasonic weld joint 473 is positioned on the other end of the body, on a bottom surface. The ultrasonic weld joint 473 is shaped and sized to fit within the cutout of the dividing layer to ensure, after ultrasonically welding, that the plug is stable and does not disconnect from either the circuit board, or the dividing layer. Ultrasonically welding the plug to the dividing layer further creates a hermetic seal between the electrode enclosure and the circuit enclosure, which minimizes moisture content change of the electrodes and thus prolongs shelf life of the device. Ultrasonically welding the plug 434 to the housing further provides outstanding mechanical strength to the electromechanical connection of the plug to the circuitry, as well as exceptional resilience to any form of pulling on the lead wires by the user. This increases the reliability of a connection that is commonly prone to fail by being yanked on or jostled loose. Two pins 472 extend from the base and are positioned perpendicular to the body 470 to extend through the dividing layer to plug into the circuit board. An insulating fin 471 can be positioned in between the pins 472 or adjacent to one of the pins 472, and prevents the pins 472 or corresponding sockets (not shown) on the circuit board from arcing to one another during high voltage discharge of the AED. In another embodiment, the plug can be attached to the middle layer or other parts of the housing by glue, epoxy, laser welding, radio frequency welding, or a combination of methods.

Figure 36:
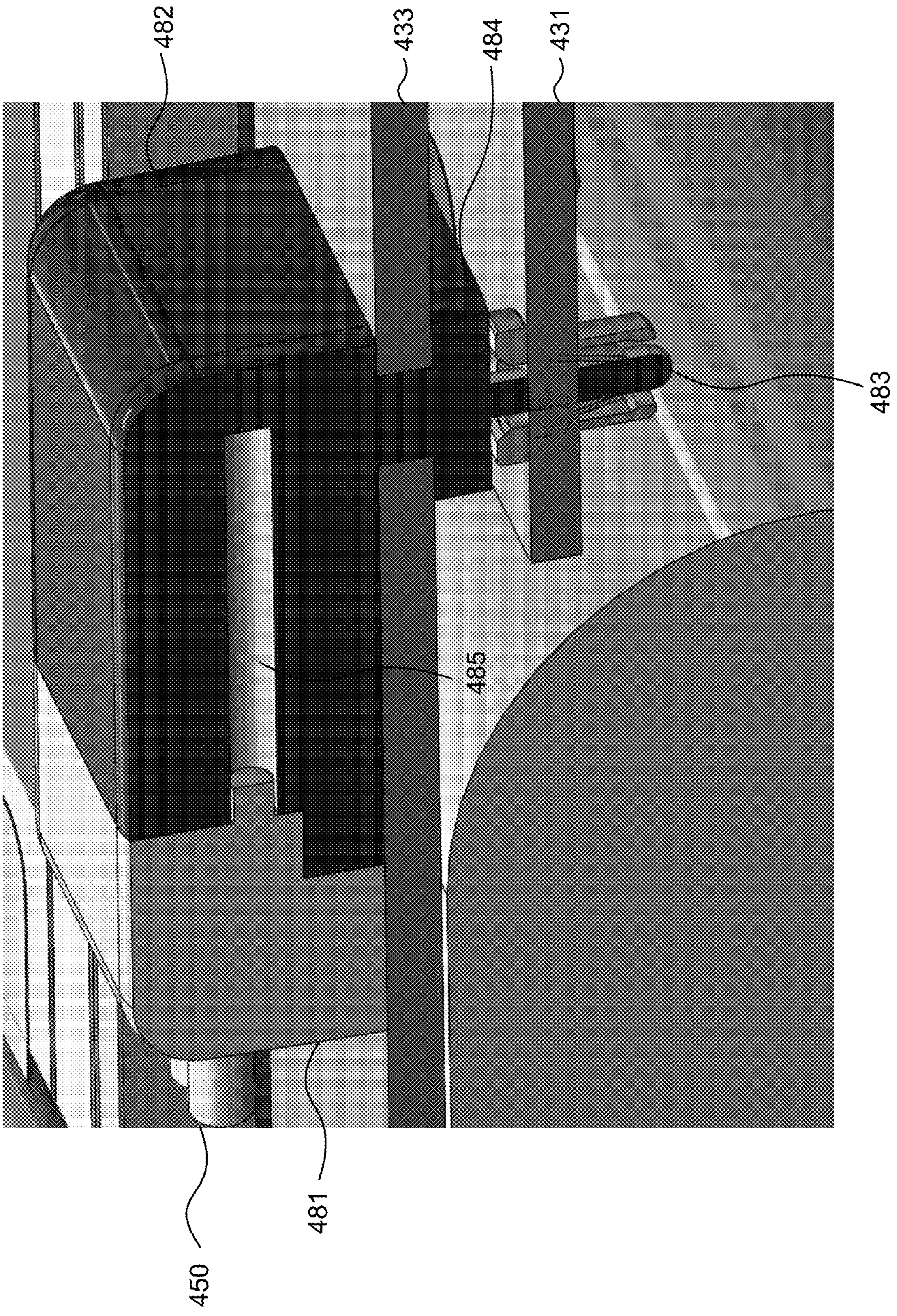
FIG. 36 is a block diagram showing, by way of example, a cross section of an AED housing with a feedthrough mechanism.

Instead of a single plug, a further wire assembly can also include a feedthrough mechanism. FIG. 36 is a block diagram showing, by way of example, a cross section of an AED housing with a feedthrough mechanism. The pad wires 450 are connected to a plug 481, which is plugged into one end of a feedthrough mechanism 482 that connects with the circuit board. One or more pins 483 extend perpendicularly from the feedthrough mechanism, on a side opposite the wires. The pins can extend through the dividing layer 433 and plug into the circuit board 431. A stopper 484 that extends from a bottom surface of the feedthrough mechanism 482 can be positioned on a bottom surface of the dividing layer 433 to secure the feedthrough mechanism to the dividing layer. The pins can extend through the stopper to reach the circuit board.

Figure 37:
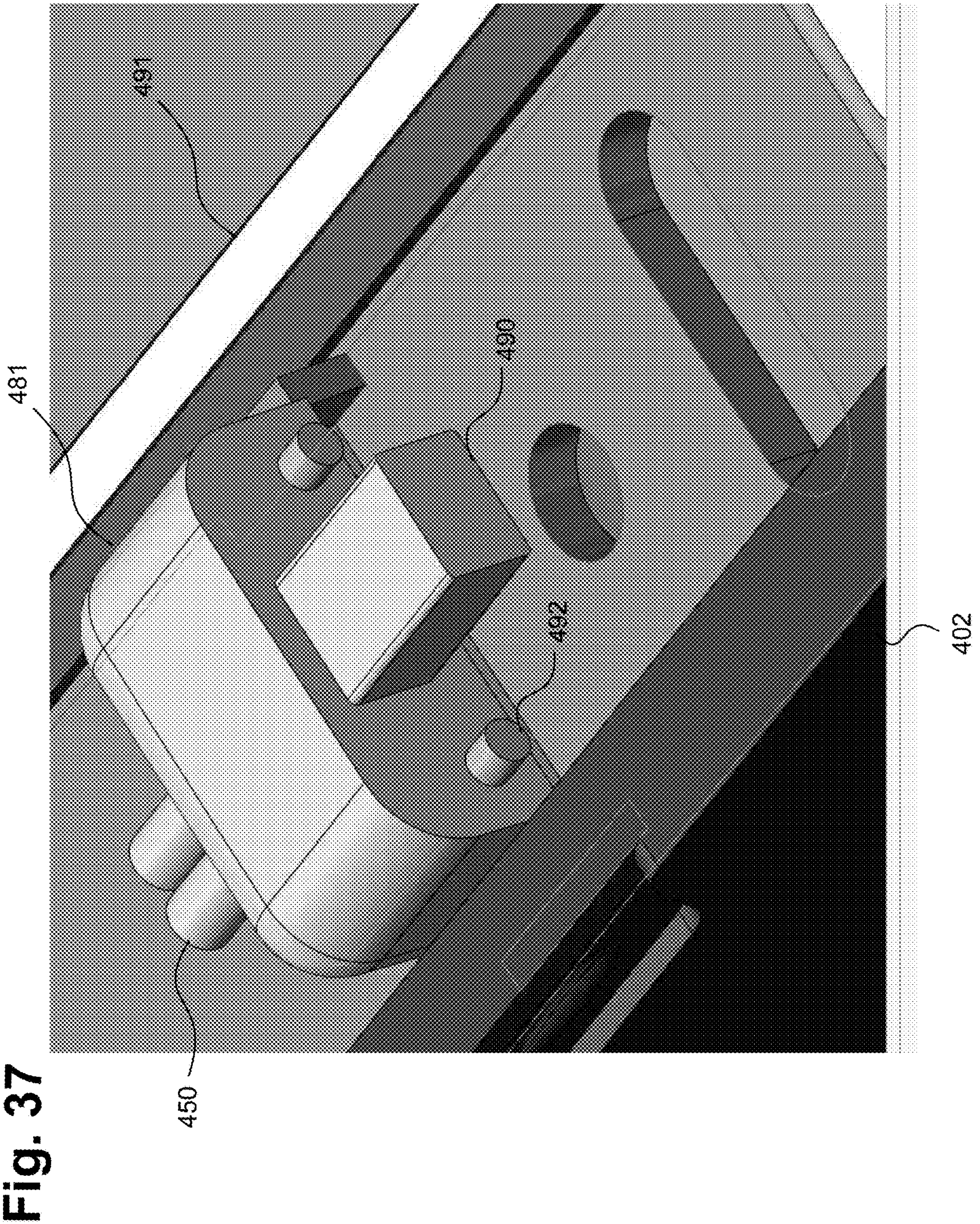
FIG. 37 is a perspective view of the plug of FIG. 36.

The plug can be connected to the feedthrough mechanism via an interlocking support member and connecting pins. FIG. 37 is a perspective view of the plug of FIG. 36. Pad wires 450 are affixed to one end of the plug 481. The opposite end of the plug 481 can include one or more connecting pins 492 that are received by one or more sockets 485 in the feedthrough mechanism, shown in FIG. 36. Defibrillation wave forms travel from the circuit board to the electrode pads via the connecting pins. One or more interlocking support members 490 can be affixed adjacent to the connecting pins 492. The interlocking support member 490 can help prevent the plug from becoming removed from the feedthrough mechanism. Further, a guide 491 can surround one or more sides of the plug and feedthrough mechanism, which are not adjacent to the wall 402 of the housing. The guide helps prevent the plug from unplugging from the feedthrough mechanism. The guide also helps increase creepage distance to the user, a key factor in electrical safety.

Figure 38:
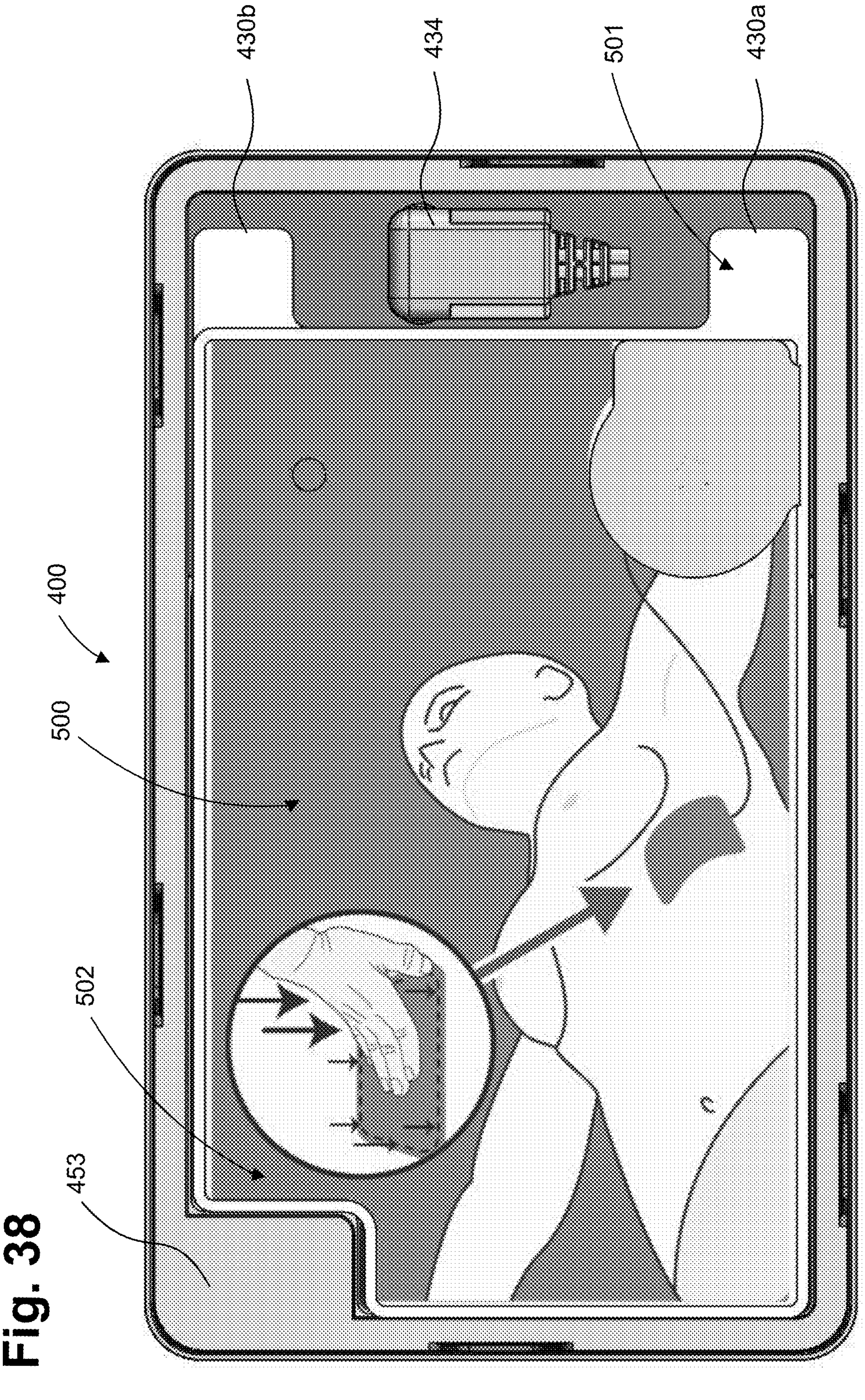
FIG. 38 is a block diagram showing, by example, electrodes pads placed in the housing.

Since the electrode pads are in the electrode enclosure with the plug, the pads can be shaped and sized to accommodate the plug and feedthrough mechanism, if present. FIG. 38 is a block diagram showing, by example, electrodes pads placed in the housing. When the cover is removed, the interior of the electrode enclosure is accessible after removal of the peelable tray lid. As described above with respect to FIG. 32, a spool rests on a dividing layer in the electrode enclosure and the electrode pads 430*a-b* rest on top of the spool. A release liner 501 can cover one side of each pad 430*a-b* and can have a tab 501 that extends beyond the pad and fits around the plug 434. The tab 501 can be used to assist a user in peeling off the protective cover for adhering the pad to a patient.

The wires (not shown) can extend from the pads on the same or different side as the tabs 501. A cutout 502 can exist on an opposite end of the pad as the wire and tab. The cutout is shaped to fit around the chamber 453 that stores the buzzer, relay, and switch. A side of each pad 430*a-b*, opposite the release liner, 501 can include illustrated or written instructions 500 on where and how to place each of the pads.

Figure 39:
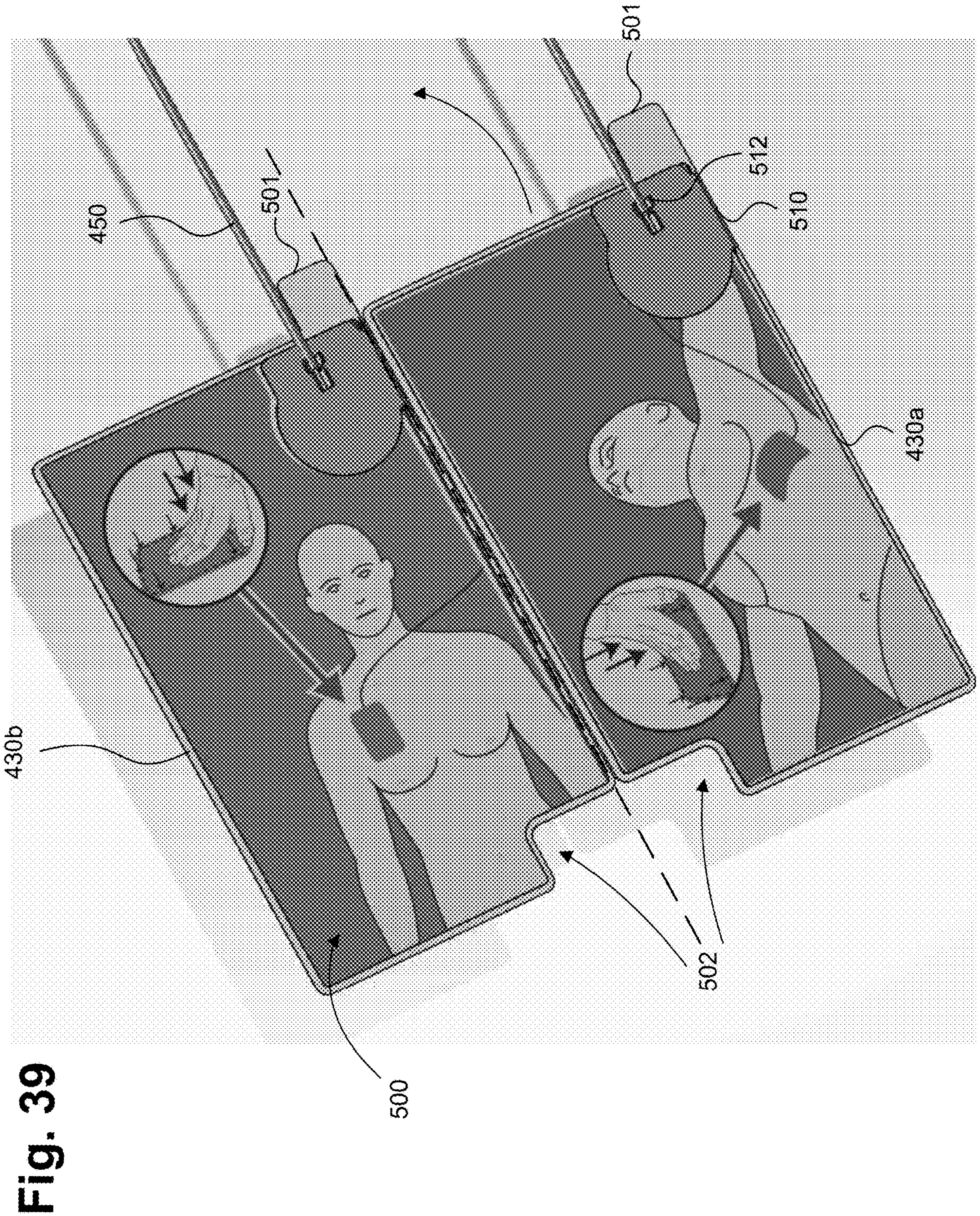
FIG. 39 is a block diagram showing, by way of example, a top view of two pads placed next to one another.

The pads can be placed back-to-back when stored in the housing 400 to make the assembly more compact and thus more pocketable as it can prevent, dependent on configuration, the thicker metal components on the pads from stacking on top of each other. If the thick metal portions were stacked on top of each other, a thicker electrode enclosure would be required. FIG. 39 is a block diagram showing, by way of example, a top view of two pads placed next to one another. Each pad 430*a-b* includes a wire 450 affixed to a top or back side, and a release liner 501 that covers a back side (not shown) of the pads to prevent hydrogel on a back surface of the pads from drying out. The release liner is removed prior to applying the pads to the patient. In one embodiment, the release liners can have a larger size than the pads to allow easy removal. Also, to improve the usability of the AED device under extremely stressful situations and to reduce confusion, the excess release liner, that exceeds the size of the pads, can be marked to distinguish the liner as an object that needs to be removed from the pads prior to placement on a patient. Without such markings, in stressful situations and under extreme pressure, some users may leave the release liner on the pads reducing the effectiveness of the shocks.

The tabs of the release liner 501 can be located on the same end of the pads as the wires. Each wire 450 can be secured to one of the pads via a wire bracket or ring terminal 512. The ring terminal can include metal. An insulating material optionally bonded with adhesive 510 can be applied over the ring terminal 512 to protect the user and patient from inappropriate shock during defibrillation.

At least a portion of the top side of the pads 430*a-b* can include instructions 500, such as by illustration or text, regarding how to place the pads. A cutout 502 is formed in a corner of each pad on an end opposite the wire. The cutout is formed on different sides of the opposite ends, such that the pads form a mirror image when the front or back sides are facing one another. The pads 430*a-b* can be placed in the electrode enclosure of the housing with their back sides facing one another to optimize the compactness of the assembly and reduce thickness by preventing thicker metal components, such as the ring terminals 512 from stacking up on top of one another.

Figure 40:
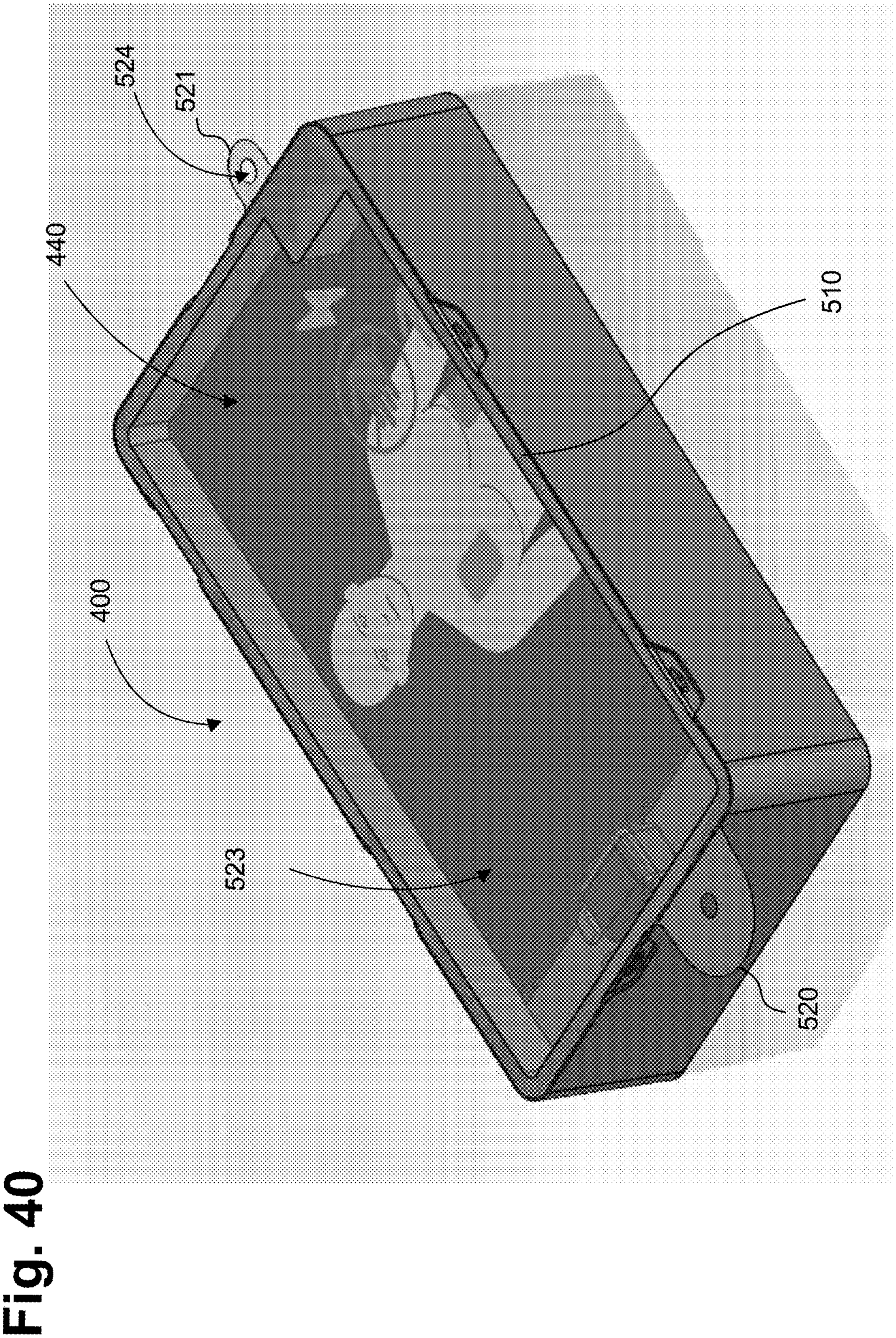
FIG. 40 is a block diagram showing, by way example, a housing with a peelable tray lid.

Once all the necessary components are provided in the electrode enclosure of the housing, a peelable tray lid can be applied to top edges of the housing walls. FIG. 40 is a block diagram showing, by way example, a housing with a peelable tray lid. The peelable tray lid 523 is affixed to the top edges of the housing walls and covers the components, such as the pad and spool, located in the electrode enclosure. The cover of the housing is placed over the peelable tray lid, which protects moisture from entering the electrode enclosure and affecting the components inside. The peelable tray lid 523 can include two tabs 520, 521. The tabs 520, 521 can be positioned on opposite sides of the peelable tray lid and include holes 524. In one embodiment, the tabs are off set from the center of the peelable tray lid. Also, the tabs can be different sizes to prevent using the wrong side of the peelable tray lid.

The tabs and holes can be used to position the peelable tray lid over the electrode enclosure to ensure accurate placement during manufacturing sealing of the peelable tray lid to the housing. Specifically, the holes of the peelable tray lid can be placed over two poles. The housing can sit between the two poles and aligned with the peelable tray lid for sealing of the peelable tray lid to the housing. To further improve the manufacturability of the device, the holes and tabs can be keyed or offset to ensure operators place the peelable tray lid right-side up. The tabs 520, 521 can also be useful for a user to remove the lid for obtaining access to the electrode enclosure.

Figure 41:
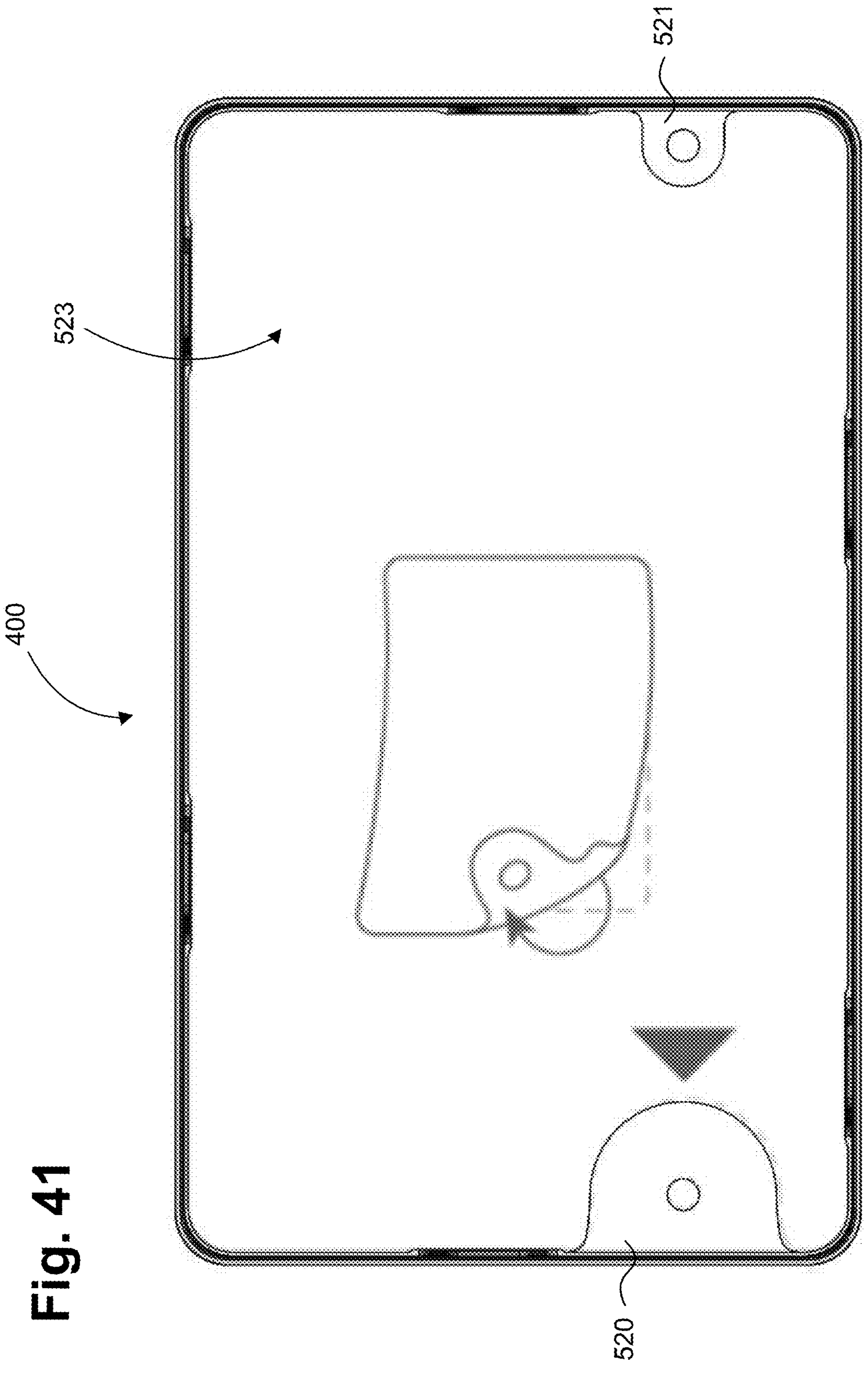
FIG. 41 is a block diagram showing, by way of example, a housing with a peelable tray lid with instructions.

Instructions for removing the peelable tray lid can be provided on a top surface. FIG. 41 is a block diagram showing, by way of example, a housing with a peelable tray lid with instructions. The peelable tray lid 523 is affixed to top edges of the housing. Illustrated or text instructions 530 can be provided on the top surface of the peelable tray lid 523. The tabs 520, 521 extending from the peelable tray lid 523 can be folded in, over the lid so they don't stick outside the housing when the cover is placed on top.

While components of the AED, such as the case and pads can be single use and disposable, the circuit can be reusable. For example, after the AED has been used, the circuit can be removed from the used case and placed into a new case with new pads and wires. However, in a further embodiment, the AED case can also be reusable. After use, the circuit and pads can be removed. The pads can be disposed of, while the circuit can be cleaned and replaced in the case with new pads.

Regardless of whether the case is to be reused, the case must be opened to access the circuit for reuse. Opening of the case is dependent on how the electrode enclosure and the circuit enclosure were joined. For example, if the two enclosures were welded together, laser cutting or ultrasonic cutting can be used to separate the two enclosures. Alternatively, if the two enclosures are screwed together, a torque controlled screwdriver can be used to separate the enclosures. Once opened, the battery can be removed from the circuit board, the circuit board can be washed and cleaned, and a new battery can be placed on the circuit board for use in another housing or case, along with new pads. The circuit board can only be reused once the patient data and logs from the previous use are offloaded.

The circuit described herein provides for the delivery of a high-voltage, high energy pulse for use in external defibrillation through a design that decreases overall device cost, size, and weight by meaningfully innovating alternatives to capacitor charging through the use of low voltage, high current supplementary defibrillation energy storage and delivery. The circuit enables high energy densities with low cost, weight, and size.

In addition, the circuit provides the basis for external defibrillators that are easy to carry, low cost and lightweight, while delivering a high-voltage, high-energy biphasic shock suitable for cardiac defibrillation and victim resuscitation. External defibrillators utilizing this circuit can help to facilitate the widespread adoption of the portable defibrillation technology and thereby meaningfully help to decrease the number of deaths from sudden cardiac arrest. Moreover, such circuits could also aid in reducing size and cost of implantable defibrillators. Additionally, the casing design contributes to size reduction, usability improvement, simplicity enhancements, and cost reduction of the AED.

While the invention has been particularly shown and described as referenced to the embodiments thereof, those skilled in the art will understand that the foregoing and other changes in form and detail may be made therein without departing from the spirit and scope of the invention.

What is claimed is:

1. A defibrillator with a non-captive wire assembly, comprising:

four walls each affixed on one side of a bottom surface;

a dividing layer affixed to each of the four walls creating an electrode enclosure configured to hold a pair of pads and a circuit enclosure configured to hold circuitry, wherein access to the circuitry is restricted by the bottom surface and dividing layer;

a pair of wires each connected on one end to one of the pads in the electrode enclosure and connected on another end to the circuitry in the circuit enclosure; and a spool comprising a barrel having two center pieces through which the pair of wires is secured and two flanges arranged with one flange on each end of the barrel with the center pieces positioned between the two flanges, wherein the wires are wound around an outer surface of the center pieces of the spool, between the two flanges, and are unwound when the pads are removed from the electrode enclosure and further wherein the two flanges are flat on an outer surface, opposite the barrel, and the flat surface of one flange rests on an interior bottom surface of the electrode enclosure.

2. A defibrillator with a non-captive wire assembly according to claim 1, wherein the spool is movable within the electrode enclosure.

3. A defibrillator with a non-captive wire assembly according to claim 1, wherein the center pieces are positioned opposite one another to form a passage in which the wires are positioned and secured prior to winding around an outer surface of the center pieces.

4. A defibrillator with a non-captive wire assembly according to claim 3, wherein the center pieces of the barrel comprise features that act as a strain relief to prevent kinking or breaking of the wires.

5. A defibrillator with a non-captive wire assembly according to claim 1, further comprising:

a peelable tray lid shaped to cover the electrode enclosure on a side opposite the circuit enclosure.

6. A defibrillator with a non-captive wire assembly according to claim 5, further comprising:

two or more tabs positioned opposite or adjacent to one another on the peelable tray lid, wherein each tab is solid or comprises holes, and each tab is shaped to have one of the same or different size than the other tab.

7. A defibrillator with a non-captive wire assembly according to claim 1, further comprising at least one of:

one or more lights positioned in the circuit enclosure and visible in the electrode enclosure through the dividing layer; and one or more status markers associated with the lights and displayed on one or more of a sticker or in-mold labeling positioned on a surface of the dividing layer facing the electrode enclosure.

8. A defibrillator with a non-captive wire assembly according to claim 1, further comprising:

a protective liner affixed to a side of each pad intended to contact skin of a patient.

9. A defibrillator with a non-captive wire assembly according to claim 8, further comprising:

wherein the pads are stacked in the electrode enclosure with the protective liner of one pad facing the protective liner of the other pad.

10. A defibrillator with a non-captive wire assembly according to claim 8, wherein the protective liners are larger than the pads and comprise markings along an outer edge.

11. A defibrillator with a non-captive wire assembly, comprising:

an electrode enclosure configured to hold a pair of pads;

a circuit enclosure configured to hold circuitry;

a pair of wires each connected on one end to one of the pads in the electrode enclosure and connected on another end to the circuity in the circuit enclosure; and a spool comprising two center pieces through which the pair of wires is secured and two flanges arranged with one flange covering the two center pieces on one end and the other flange covering the two center pieces on an opposite end, wherein the wires are wound around the center pieces of the spool, between the flanges, and are unwound when the pads are removed from the electrode enclosure and further wherein the two flanges are flat on an outer surface, opposite the two center pieces, and the flat surface of one flange rests on an interior bottom surface of the electrode enclosure.

12. A defibrillator with a non-captive wire assembly according to claim 11, wherein the spool is movable within the electrode enclosure.

13. A defibrillator with a non-captive wire assembly according to claim 11, wherein the center pieces are positioned opposite one another to form a passage in which the wires are secured prior to winding around an outer surface of the center pieces.

14. A defibrillator with a non-captive wire assembly according to claim 13, wherein the center pieces act as a strain relief to prevent kinking or breaking of the wires.

15. A defibrillator with a non-captive wire assembly according to claim 11, further comprising:

a peelable tray lid shaped to cover the electrode enclosure on a side opposite the circuit enclosure.

16. A defibrillator with a non-captive wire assembly according to claim 15, further comprising:

two or more tabs positioned opposite or adjacent to one another on the peelable tray lid, wherein each tab is solid or comprises holes, and each tab is shaped to have one of the same or different size than the other tab.

17. A defibrillator with a non-captive wire assembly according to claim 11, further comprising at least one of:

one or more lights positioned in the circuit enclosure and visible in the electrode enclosure through the dividing layer; and one or more status markers associated with the lights and displayed on one or more of a sticker or in-mold labeling positioned on a surface of the dividing layer facing the electrode enclosure.

18. A defibrillator with a non-captive wire assembly according to claim 11, further comprising:

a protective liner affixed to a side of each pad intended to contact skin of a patient.

19. A defibrillator with a non-captive wire assembly according to claim 18, further comprising:

wherein the pads are stacked in the electrode enclosure with the protective liner of one pad facing the protective liner of the other pad.

20. A defibrillator with a non-captive wire assembly according to claim 18, wherein the protective liners are larger than the pads and comprise markings along an outer edge.

* * * * *